United States Patent
Janabi-Sharifi et al.

(10) Patent No.: US 10,564,057 B2
(45) Date of Patent: Feb. 18, 2020

(54) TEMPERATURE INVARIANT FORCE AND TORQUE SENSOR ASSEMBLIES

(71) Applicants: Farrokh Janabi-Sharifi, North York (CA); Asim Cheema, Mississauga (CA); Ata Taghipour, Toronto (CA)

(72) Inventors: Farrokh Janabi-Sharifi, North York (CA); Asim Cheema, Mississauga (CA); Ata Taghipour, Toronto (CA)

( * ) Notice: Subject to any disclaimer, the term of this patent is extended or adjusted under 35 U.S.C. 154(b) by 100 days.

(21) Appl. No.: 15/560,804

(22) PCT Filed: Mar. 22, 2016

(86) PCT No.: PCT/CA2016/050331
§ 371 (c)(1),
(2) Date: Sep. 22, 2017

(87) PCT Pub. No.: WO2016/149819
PCT Pub. Date: Sep. 29, 2016

(65) Prior Publication Data
US 2018/0113038 A1    Apr. 26, 2018

Related U.S. Application Data

(60) Provisional application No. 62/136,817, filed on Mar. 23, 2015.

(51) Int. Cl.
*G01L 1/24* (2006.01)
*G01L 1/26* (2006.01)
(Continued)

(52) U.S. Cl.
CPC ........ *G01L 1/246* (2013.01); *A61B 17/00234* (2013.01); *G01B 11/165* (2013.01);
(Continued)

(58) Field of Classification Search
CPC ... G01L 1/246; G01L 5/16; G01L 1/26; G01L 5/0028; G01L 3/108; G01B 11/165;
(Continued)

(56) References Cited

U.S. PATENT DOCUMENTS 6,276,215 B1    8/2001   Berg
6,584,248 B2    6/2003   Franzen et al.
(Continued)

FOREIGN PATENT DOCUMENTS

WO    2013/012870 A1    1/2013
WO    2013/150019 A1    10/2013

OTHER PUBLICATIONS

International Search Report and Written Opinion dated Jun. 21, 2016 in corresponding International Patent Application No. PCT/CA2016/050331.
(Continued)

*Primary Examiner* — Tony Ko
(74) *Attorney, Agent, or Firm* — Bereskin & Parr LLP/S.E.N.C.R.L., s.r.l.; Tony Orsi

(57) ABSTRACT

Various sensor assemblies are described herein that can measure axial and lateral forces and/or axial and lateral torques acting on an instrument independent of steady state temperature variations. In one embodiment, the sensor assembly has a sensor body for coupling to the instrument such that a shaft and tip of the instrument extend from opposing ends of the sensor body. The sensor body has first and second strain sensing regions. The sensor assembly further includes first and second strain sensors coupled to and configured to measure axial strain of the first and second regions, respectively. During use, when the sensor body is coupled to the instrument, each of the first and second regions experience an opposite one of a tensile axial strain
(Continued)

and a compressive axial strain in response to an axial force or an axial torque acting on the tip of the instrument.

47 Claims, 30 Drawing Sheets

(51) Int. Cl.
*A61B 17/00* (2006.01)
*G01B 11/16* (2006.01)
*G01L 5/16* (2020.01)
*A61B 90/00* (2016.01)

(52) U.S. Cl.
CPC .............. *G01L 1/26* (2013.01); *G01L 5/16* (2013.01); *A61B 2090/066* (2016.02); *A61B 2562/0266* (2013.01)

(58) Field of Classification Search
CPC ...... A61B 17/00234; A61B 2562/0266; A61B 2090/066
See application file for complete search history.

(56) References Cited

U.S. PATENT DOCUMENTS

| | | | |
|---|---|---|---|
| 6,695,808 B2 | 2/2004 | Tom | |
| 8,048,063 B2 | 11/2011 | Aeby et al. | |
| 8,075,498 B2 | 12/2011 | Leo et al. | |
| 8,157,789 B2 | 4/2012 | Leo et al. | |
| 8,281,670 B2 | 10/2012 | Larkin et al. | |
| 8,298,227 B2 | 10/2012 | Leo et al. | |
| 8,491,574 B2 | 7/2013 | Blumenkranz | |
| 8,567,265 B2 | 10/2013 | Aeby et al. | |
| 8,613,230 B2 | 12/2013 | Blumenkranz et al. | |
| 8,622,935 B1 | 1/2014 | Leo | |
| 2007/0151390 A1 | 7/2007 | Blumenkranz et al. | |
| 2009/0177095 A1 | 7/2009 | Aeby et al. | |
| 2009/0248038 A1* | 10/2009 | Blumenkranz | B25J 13/085 606/130 |
| 2010/0168620 A1 | 7/2010 | Klimovitch et al. | |
| 2012/0220879 A1 | 8/2012 | Fandrey et al. | |
| 2012/0265102 A1 | 10/2012 | Leo et al. | |
| 2012/0316432 A1 | 12/2012 | Younge et al. | |
| 2013/0018400 A1 | 1/2013 | Milton et al. | |
| 2013/0190734 A1 | 7/2013 | Taylor et al. | |
| 2014/0024970 A1 | 1/2014 | Govari | |
| 2014/0081264 A1 | 3/2014 | Fandrey et al. | |
| 2014/0088614 A1 | 3/2014 | Blumenkranz | |
| 2014/0107627 A1 | 4/2014 | Blumenkranz et al. | |
| 2014/0137667 A1 | 5/2014 | Blumenkranz et al. | |

OTHER PUBLICATIONS

Peirs, et al., "A micro optical force sensor for force feedback during minimally invasive robotic surgery", Sensors and Actuators A, 2004, 115: 447-455.

Polygerinos, et al., "Triaxial Catheter-Tip Force Sensor for MRI-Guided Cardiac Procedures", IEEE/ASME Transactions on Mechatronics, 2013, 18(1): 386-396.

Rosen, et al., "Surgeon-Tool Force/Torque Signatures—Evaluation of Surgical Skills in Minimally Invasive Surgery", Stud Health Technol Inform., 1999, 62: 290-296.

Kanagaratnam, et al., "Experience of robotic catheter ablation in humans using a novel remotely steerable catheter sheath", J Interv Card Electrophysiol., 2008, 21(1): 19-26.

Polygerinos, et al., "Novel Miniature MRI-Compatible Fiber-Optic Force Sensor for Cardiac Catheterization Procedures", 2010 IEEE International Conference on Robotics and Automation (ICRA), Anchorage, Alaska, 2010, pp. 2598-2603.

Sieber, et al., "A novel haptic platform for real time bilateral biomanipulation with a MEMS sensor for triaxial force feedback", Sensors and Actuators A, 2008, 142: 19-27.

Arata, et al., "Fiber optic force sensor for medical applications within a backbone-shape structure", Procedia CIRP, 2013, 5: 66-69.

Iordachita, et al., "A sub-millimetric, 0.25 mN resolution fully integrated fiber-optic force-sensing tool for retinal microsurgery", Int J CARS, 2009, 4(4): 383-390.

Perna, et al., "Assessment of Catheter Tip Contact Force Resulting in Cardiac Perforation in Swine Atria Using Force Sensing Technology", Journal of Circ Arrhythm Electrophysiol., 2011, 4(2): 218-224.

Eick, "Temperature controlled radiofrequency ablation", Indian Pacing Electrophysiol J., 2002, 2(3): 66-73.

Boyer, et al., eds., "Materials Properties Handbook: Titanium Alloys", Ohio: ASM International, 1994, p. 484.

Henry, et al., eds., Ch. 27, In "Fatigue Data Book: Light Structural Alloys", Ohio: ASM International, 1995, p. 189.

Saravanan, et al., Ch. 1.6.2, In "Metal and Alloy Bonding: An Experimental Analysis", Berlin: Springer-Verlag London Limited, 2012, p. 15.

Berlin et al., In DISEGI et al., eds., "Cobalt-Base Alloys for Biomedical Applications", West Conshohocken, Pennsylvania: ASTM International, 1999, pp. 89-90.

Koike, et al., "Evaluation of Titanium Alloys Fabricated Using Rapid Prototyping Technologies—Electron Beam Melting and Laser Beam Melting", Materials, 2011, 4(10): 1776-1792.

Davis, et al., ed., Ch. 4, In "Handbook of Materials for Medical Devices", Ohio: ASM International, 2003, p. 66.

Website, Objective Technologies, Inc., 2008 <http://www.object.com>.

Hodgson et al., Ch. 13, In Totten et al., eds., "Mechanical Tribology: Materials, Characterization, and Applications", New York: Marcel Dekker, 2004, pp. 429-438.

International Preliminary Report on Patentability dated Oct. 5, 2017 in corresponding International Patent Application No. PCT/CA2016/050331.

* cited by examiner

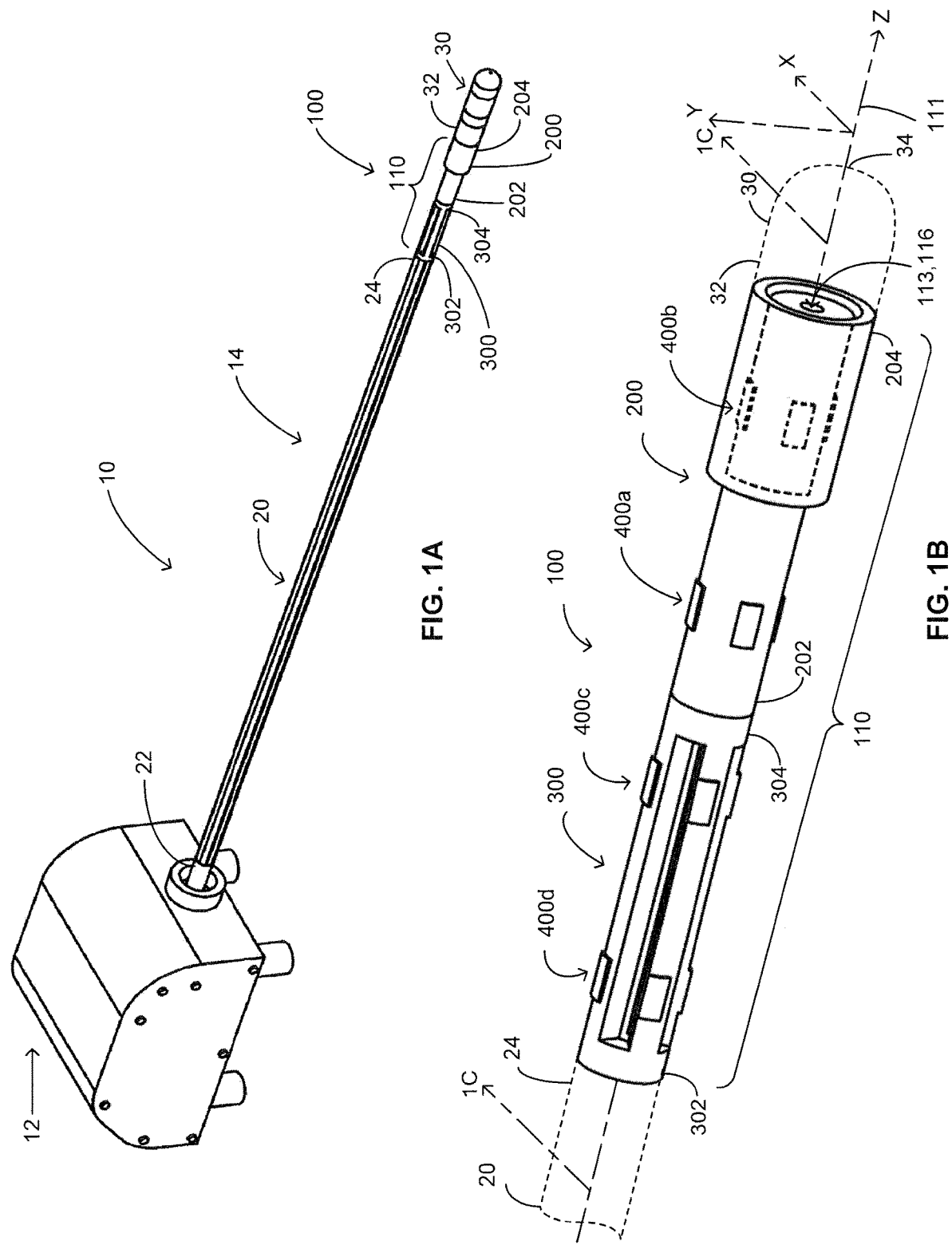

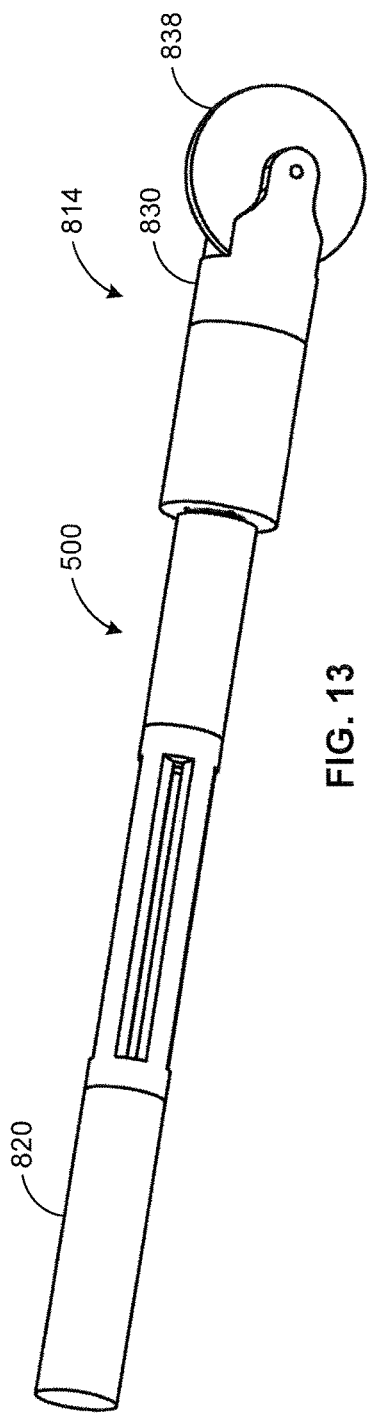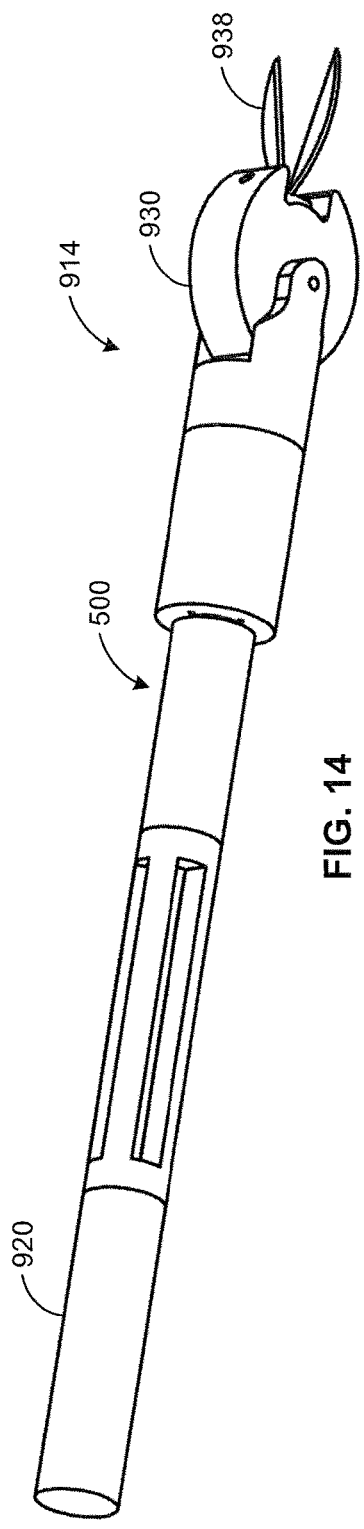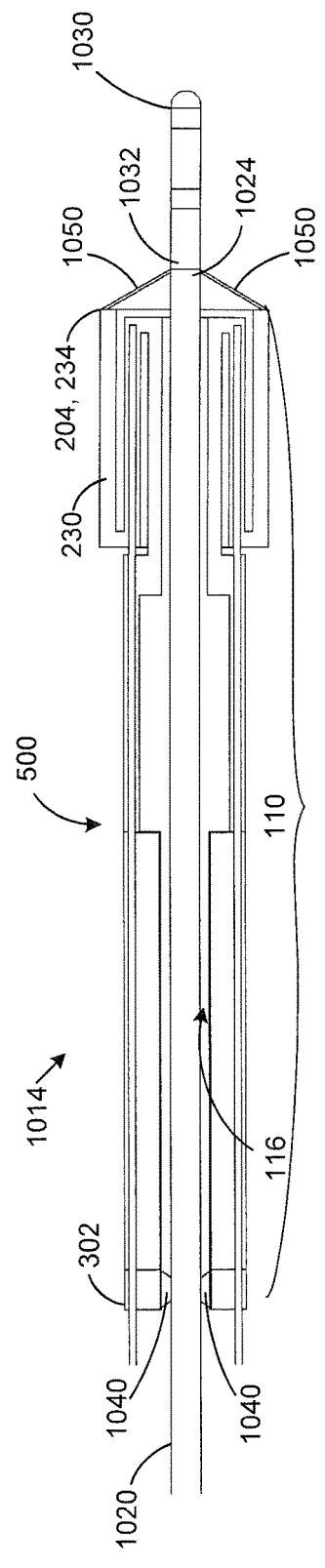
FIG. 13
FIG. 14
FIG. 15

TEMPERATURE INVARIANT FORCE AND TORQUE SENSOR ASSEMBLIES

CROSS-REFERENCE TO RELATED APPLICATION

This application claims the benefit of U.S. Provisional Patent Application No. 62/136,817 filed Mar. 23, 2015; the entire contents of Patent Application No. 62/136,817 are hereby incorporated by reference.

FIELD

The disclosure relates to sensor assemblies. More specifically, the disclosure relates to temperature insensitive sensor assemblies for sensing at least one of forces, torques, and moments acting on a portion of an instrument.

BACKGROUND

Sensor assemblies can be used to measure forces or torques acting on a mechanical instrument as a result of its interaction with an object. Many sensor assemblies include strain sensors configured to measure strains experienced by a sensor body of the sensor assembly as a result of such forces or torques. The measured strains can be used to resolve one or more components of such forces or torques.

However, many existing sensor assemblies are incapable of distinguishing between thermal strains resulting from temperature variations and mechanical strains resulting from forces or torques acting on the instrument. In such sensor assemblies, thermal strains may introduce significant error when measurements form strain sensors are used to determine components of forces or torques acting on the instrument.

In recent years some sensor assemblies have been developed that are capable of compensating for thermal strains resulting from steady state temperature variations. However, these sensor assemblies are often highly complex and require many components, resulting in a high cost of production. Furthermore, some of these sensors assemblies are limited to resolving only a subset of axial and lateral forces and axial torque independent of steady state temperature variations.

SUMMARY

Various embodiments for temperature invariant sensor assemblies are provided according to the teachings herein.

In general, in at least one aspect, disclosed herein is an axial force sensor assembly for an instrument having a shaft and a tip. The sensor assembly may comprise an axial force sensor body for coupling to the instrument such that the shaft and the tip of the instrument extend from respective opposing ends of the sensor body. The sensor body may have a central longitudinal axis extending between the opposing ends and first and second regions extending about the central longitudinal axis. The sensor assembly may further comprise a first strain sensor coupled to the first region and configured to measure axial strain of the first region, and a second strain sensor coupled to the second region and configured to measure axial strain of the second region. In some example embodiments, when the sensor body is coupled to the shaft and the tip and is in use, each of the first and second regions of the sensor body experiences an opposite one of a tensile axial strain and a compressive axial strain in response to an axial force acting on the tip of the instrument along the central longitudinal axis.

In some example embodiments, the sensor body may comprise first and second axially overlapping tubular members affixed to one another at respective distal ends and free to deform relative to one another along the central longitudinal axis. Respective proximal ends of the first and second tubular members may be used to couple the sensor body to a respective one of the tip and the shaft of the instrument. In some example embodiments, the first tubular member may comprise the first region of the sensor body and the second tubular member may comprise the second region of the sensor body.

In some example embodiments, the second tubular member may axially overlap the first tubular member, and the sensor body may further comprise a third tubular member for coupling the proximal end of the second tubular member to the respective opposite one of the tip and the shaft of the instrument. In some example embodiments, the third tubular member may have a proximal end affixed to the proximal end of the second tubular member, may axially overlap the second tubular member, and may be free to deform relative to the second tubular member along the central longitudinal axis of the sensor body.

In some example embodiments, the first tubular member may comprise a proximal section and a distal section disposed between proximal and distal ends of the first tubular member. The proximal section of the first tubular member may comprise the first region and the second tubular member may axially overlap the distal section of the first tubular member.

In some example embodiments, the first tubular member may have a first cross sectional area in the first region and the second tubular member may have a second cross sectional area in the second region. The first cross sectional area may be substantially equal to the second cross sectional area.

In some example embodiments, the first cross sectional area may be defined by a first inner radius and a first outer radius, and the second cross sectional area may be defined by a second inner radius substantially equal to the first inner radius and a second outer radius substantially equal to the first outer radius.

In some example embodiments, the first strain sensor may comprise a first fiber Bragg grating on a first section of an optical fiber and the second strain sensor comprises a second fiber Bragg grating on a second section of the optical fiber.

In some example embodiments, the sensor assembly may further comprise a first plurality of strain sensors including the first strain sensor. The first plurality of strain sensors may be coupled to the first region and spaced equidistantly about the central longitudinal axis of the sensor body. The first plurality of strain sensors may be configured to measure axial strain of the first region. The sensor assembly may further comprise a second plurality of strain sensors including the second strain sensor. The second plurality of strain sensors may be coupled to the second region and spaced equidistantly about the central longitudinal axis of the sensor body. The second plurality of strain sensors may be configured to measure axial strain of the second region.

In some example embodiments, each of the first and second plurality of strain sensors may include an equal number of strain sensors.

In some example embodiments, each of the first and second plurality of strain sensors may include 4 strain sensors.

In some example embodiments, the first and second strain sensors may be oriented about the central longitudinal axis at a same angle.

In some example embodiments, the first and second strain sensors may be configured to generate first and second strain signals, respectively. The first and second strain signals may correspond to the axial strain of the first region and the axial strain of the second region, respectively. The first and second strain sensors may be further configured to provide the first and second strain signals to a processing unit for determining the axial force based on a combination of the first and second strain signals. The axial force may be invariant to steady state temperature variations.

In some example embodiments, the instrument may be a minimally invasive surgical instrument.

In another aspect, also disclosed herein is an axial torque sensor assembly for an instrument having a shaft and a tip. The sensor assembly may comprise an axial torque sensor body having a proximal end and a distal end for coupling to the shaft and the tip of the instrument, respectively. The sensor body may define a central longitudinal axis extending therethrough between the proximal and distal ends, and may have a first region and a second region. The sensor assembly may further comprise a first strain sensor coupled to the first region and configured to measure axial strain of the first region, and a second strain sensor coupled to the second region and configured to measure axial strain of the second region. In some example embodiments, when the sensor body is coupled to the shaft and the tip and is in use, each of the first and second regions of the sensor body may experience an opposite one of a tensile axial strain and a compressive axial strain in response to an axial torque acting on the tip of the instrument about the axis.

In some example embodiments, the sensor body is tubular and may comprise a proximal portion extending inwardly from a proximal end of the sensor body; a distal portion extending inwardly from a distal end of the sensor body; a central side wall extending about the central longitudinal axis between the proximal portion and the distal portion; and a first slit extending through the central side wall and between the proximal portion and the distal portion. The central side wall may comprise the first and second regions.

In some example embodiments, the first slit may be defined by first and second opposing longitudinal side faces extending between the proximal portion and the distal portion of the sensor body, and the first region and the second region may be located near the first longitudinal side face of the slit.

In some example embodiments, the first region may be located near the proximal portion of the sensor body and the second region may be located near the distal portion of the sensor body.

In some example embodiments, the first slit may be defined by first and second opposing longitudinal side faces extending between the proximal portion and the distal portion of the sensor body. The first region may be located near the first longitudinal side face of the slit and the second region may be located near the second longitudinal side face of the slit.

In some example embodiments, the first region and the second region may be located near the distal portion of the sensor body.

In some example embodiments, the first region and the second region may be located near the proximal portion of the sensor body.

In some example embodiments, the sensor body may further comprise a second slit extending through the central side wall and between the proximal portion and the distal portion of the sensor body.

In some example embodiments, the first and second slits may be spaced equidistantly about the central longitudinal axis of the sensor body.

In some example embodiments, the sensor assembly may further comprise a plurality of slits including the first slit. Each of the slits may be spaced equidistantly about the central longitudinal axis of the sensor body, and may extend through the central side wall and between the proximal portion and the distal portion of the sensor body. The sensor assembly may further comprise a first plurality of strain sensors including the first strain sensor. Each strain sensor of the first plurality of strain sensors may be coupled to and configured to measure axial strain of a respective first region of the sensor body. The sensor assembly may further comprise a second plurality of strain sensors including the second strain sensor. Each strain sensor of the second plurality of strain sensors may be coupled to and configured to measure axial strain of a respective second region of the sensor body. The central side wall may comprise the respective first and second regions. In some example embodiments, when the sensor body is coupled to the shaft and the tip and is in use, each of the respective first regions may experience one of a compressive axial strain and a tensile axial strain while each of the respective second regions experiences the other one of a compressive axial strain and a tensile axial strain in response to the torque acting on the tip of the instrument about the central longitudinal axis.

In some example embodiments, each slit may be defined by first and second opposing longitudinal side faces extending between the proximal portion and the distal portion of the sensor body, and each first region and each second region may be located near a respective first longitudinal side face of a respective slit.

In some example embodiments, each first region may be located near the proximal portion of the sensor body and each second region may be located near the distal portion of the sensor body.

In some example embodiments, each slit may be defined by first and second opposing longitudinal side faces extending between the proximal portion and the distal portion of the sensor body, each first region may be located near a respective first longitudinal side face of a respective slit, and each second region may be located near a respective second longitudinal side face of a respective slit.

In some example embodiments, each first region and each second region may be located near the distal portion of the sensor body.

In some example embodiments, each first region and each second region may be located near the proximal portion of the sensor body.

In some example embodiments, each of the first plurality of strain sensors and the second plurality of strain sensors may include an equal number of strain sensors.

In some example embodiments, the number of strain sensors in each of the first and second plurality of strain sensors may be equal to a number of slits in the plurality of slits.

In some example embodiments, the number of slits in the plurality of slits and the number of strain sensors in each of the first and second plurality of strain sensors may be 4.

In some example embodiments, the strain sensors in each of the first and second plurality of strain sensors may be spaced equidistantly about the central longitudinal axis.

In some example embodiments, each slit may extend substantially parallel to the central longitudinal axis of the sensor body.

In some example embodiments, the first strain sensor and the second strain sensor may be oriented about the central longitudinal axis at a same angle.

In some example embodiments, the first and second strain sensors may be configured to generate first and second strain signals, respectively. The first and second strain signals may correspond to the axial strain of the first region and the axial strain of the second region, respectively. The first and second strain sensors may be further configured to provide the first and second strain signals to a processing unit for determining the axial torque based on a combination of the first and second strain signals. The axial torque may be invariant to steady state temperature variations.

In some example embodiments, the first strain sensor may comprise a first fiber Bragg grating on a first section of an optical fiber and the second strain sensor may comprise a second fiber Bragg grating on a second section of the optical fiber.

In some example embodiments, the instrument may be a minimally invasive surgical instrument.

Also disclosed herein is an axial force and torque sensor assembly having a first portion and a second portion. The first portion may include the axial force sensor body described above. The second portion may include the axial torque sensor body described above. The sensor assembly may be configured to measure signals indicative of at least one of an axial force and an axial torque acting on the tip of the instrument during use.

In another aspect, also disclosed herein is a method of sensing an axial force acting on a tip of an instrument having a sensor body of a sensor assembly coupled to a shaft and the tip of the instrument. In some example embodiments, the method may comprise receiving at a processing unit a first set of strain signals corresponding to axial strain of a first region of the sensor body resulting from the axial force. The axial strain of the first region may correspond to one of (1) tensile axial strain and (2) compressive axial strain. The method may further comprise receiving at the processing unit a second set of strain signals corresponding to axial strain of a second region of the sensor body resulting from the axial force. The axial strain of the second region may correspond to the other one of (1) tensile axial strain and (2) compressive axial strain. The method may further comprise determining the axial force based on a combination of the first set of strain signals and the second set of strain signals using the processing unit. The axial force may be invariant to steady state temperature variations. The method may further comprise transmitting a signal corresponding to the determined axial force to a user.

In some example embodiments, the axial force may be calculated by $F_z=\alpha(\epsilon_B-\epsilon_A)$. $\alpha$ may be a function of a geometry and material characteristics of the sensor body at the first and second regions and a number of respective strain signals in the first and second set of strain signals. $\epsilon_A$ may be one or more strain signals from the first set of strain signals. $\epsilon_B$ may be one or more strain signals from the second set of strain signals.

In some example embodiments, $\epsilon_A$ and $\epsilon_B$ may include an equal number of strain signals.

In some example embodiments, there may be 4 strain sensors at the first region and 4 strain sensors at the second region. The first region may be defined by a first cross sectional area of the body and the second region may be defined by a second cross sectional area of the body substantially equal to the first cross sectional area. $\alpha$ may be equal to $$\frac{EA}{8},$$

where t may De a modulus of elasticity in an axial direction of a material of the first and second regions and A may be one of the first cross sectional area and the second cross sectional area. $\epsilon_A$ may be equal to $\epsilon_5+\epsilon_6+\epsilon_7+\epsilon_8$, where $\epsilon_5$, $\epsilon_6$, $\epsilon_7$, $\epsilon_8$ may be respective strain signals of the first set of strain signals. $\epsilon_B$ may be equal to $\epsilon_1+\epsilon_2+\epsilon_3+\epsilon_4$, where $\epsilon_1$, $\epsilon_2$, $\epsilon_3$, $\epsilon_4$ may be respective strain signals of the second set of strain signals.

In some example embodiments, the method may further comprise providing a graphical display of the determined axial force to the user.

In some example embodiments, the method may further comprise providing haptic feedback corresponding to the determined axial force to the user.

In another aspect, also disclosed herein is a method of sensing an axial torque acting on a tip of an instrument having a sensor body of a sensor assembly coupled to a shaft and the tip of the instrument. The method may comprise receiving at a processing unit a first set of strain signals corresponding to axial strain of one or more first regions of the body resulting from the axial torque. The axial strain of the one or more first regions may correspond to one of (1) tensile axial strain and (2) compressive axial strain. The method may further comprise receiving at the processing unit a second set of strain signals corresponding to axial strain of a corresponding number of second regions of the body resulting from the axial torque. The axial strain of the corresponding number of second regions may correspond to the other one of (1) tensile axial strain and (2) compressive axial strain. The method may further comprise determining the axial torque based on a combination of the first set of strain signals and the second set of strain signals using the processing unit. The determined axial torque may be invariant to steady state temperature variations. The method may further comprise transmitting a signal corresponding to the determined axial torque to a user.

In some example embodiments, the axial torque may be calculated by $T_z=\tau(\epsilon_D-\epsilon_C)$. $\tau$ may be a function of a geometry and material characteristics of the body at the one or more first and second regions and a number of strain signals in the first and second set of strain signals. $\epsilon_C$ may be one or more strain signals from the first set of strain signals. $\epsilon_D$ may be one or more strain signals from the second set of strain signals.

In some example embodiments, $\epsilon_C$ and $\epsilon_D$ may include an equal number of strain signals.

In some example embodiments, there may be 4 strain sensors at the one or more first regions and 4 strain sensors at the one or more second regions. $\epsilon_C$ may be equal to $\epsilon_9+\epsilon_{10}+\epsilon_{11}+\epsilon_{12}$, where $\epsilon_9$, $\epsilon_{10}$, $\epsilon_{11}$, $\epsilon_{12}$ may be respective strain signals of the first set of strain signals. $\epsilon_D$ may be equal to $\epsilon_{13}+\epsilon_{14}+\epsilon_{15}+\epsilon_{16}$, where $\epsilon_{13}$, $\epsilon_{14}$, $\epsilon_{15}$, $\epsilon_{16}$ may be respective strain signals of the second set of strain signals.

In some example embodiments, the method may further comprise providing a graphical display of the determined axial torque to the user.

In some example embodiments, the method may further comprise providing haptic feedback corresponding to the determined axial torque to the user.

In some example embodiments, the sensor assembly of any of the methods described above may comprise the axial-force sensor assembly described above, the axial-torque sensor assembly described above, or the axial force and torque sensor assembly described above.

In another aspect, also disclosed herein is a computer readable medium comprising a plurality of instructions that are executable on a processing unit of a device for configuring the device to implement any of the methods described above.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how they may be carried into effect, reference will be made, by way of example, to the accompanying drawings which show at least one example embodiment, and which are now described. The drawings are not intended to limit the scope of the teachings described herein.

FIG. 1A is a perspective view of a catheter ablation system having an example embodiment of a sensor assembly.

FIG. 1B is a perspective view of the sensor assembly of FIG. 1A.

FIG. 13 is a perspective view of the sensor assembly of FIG. 9 attached to another MIS instrument.

FIG. 14 is a perspective view of the sensor assembly of FIG. 9 attached to another MIS instrument.

FIG. 15 is a cross-sectional view of the sensor assembly of FIG. 9 attached to another MIS instrument.

Figure 1C:
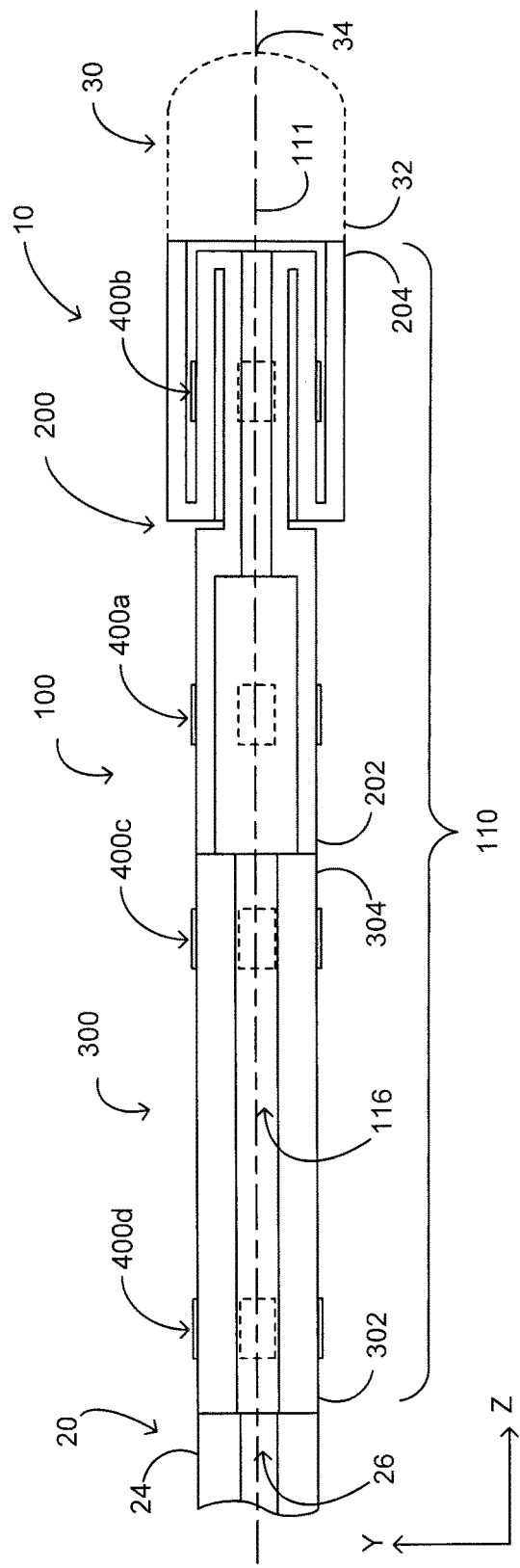
FIG. 1C is a cross section taken along line 1C-1C in FIG. 1B.

Further aspects and features of the embodiments described herein will appear from the following description taken together with the accompanying drawings.

DETAILED DESCRIPTION

Various apparatuses or processes will be described below to provide an example of at least one embodiment of the claimed subject matter. No embodiment described below limits any claimed subject matter and any claimed subject matter may cover processes or apparatuses that differ from those described below. The claimed subject matter is not limited to processes or apparatuses having all of the features of any one process or device described below or to features common to multiple or all of the processes or apparatuses described below. It is possible that a process or apparatus described below is not an embodiment of any claimed subject matter. Any subject matter that is disclosed in a process or device described below that is not claimed in this document may be the subject matter of another protective instrument, for example, a continuing patent application, and the applicants, inventors, or owners do not intend to abandon, disclaim, or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical element or electrical signal (either wired or wireless) or a mechanical element depending on the particular context.

It should be noted that terms of degree such as "substantially", "about" and "approximately" as used herein mean a reasonable amount of deviation of the modified term such that the end result is not significantly changed. These terms of degree may be construed as including a certain deviation of the modified term if this deviation would not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Various sensor assemblies are described herein. The sensor assemblies may generally provide for sensing at least one of forces, torques, or moments acting on a portion of an instrument. For example, a sensor assembly may be configured to sense axial and lateral forces, axial torque, or bending moments acting on the tip of the instrument. Notably, the sensor assemblies described herein are temperature invariant, in that the forces, torques, or moments may be resolved independent of steady state temperature variations. This may allow for the sensor assemblies to be used with instruments in applications or environments that are subject to temperature variations without causing measurement errors resulting from the temperature variations.

For example, the sensor assemblies may be used for surgical applications, such as minimally invasive surgery (MIS). During MIS, depending on the surgical procedure, a surgeon may employ a variety of MIS instruments, such as graspers, needles, cautery probes, and other similar instruments, to perform various functions within a patient's body. A sensor assembly as described herein may be coupled between a shaft and the tip of the MIS instrument, and used to sense at least one of forces, torques, or moments acting on the instrument. Based on signals received from the sensor assembly, the surgeon can be provided with visual or haptic feedback during surgery of the forces, torques, and/or moments, to assist the surgeon in properly manipulating the instrument within the patient's body.

As a result of being temperature invariant, steady state temperature variations within the patient's body may not affect the sensor assembly's measurement of the forces, torques, or moments acting on the instrument. Such temperature invariance may be particularly useful for MIS instruments such as ablation catheters, as an end portion of an ablation catheter may reach temperatures of 50° C. or more when generating RF signals to ablate heart tissue.

Although the sensor assemblies described herein are generally directed to surgical applications and MIS instruments such as ablation catheters, the sensor assemblies may be used with other instruments, as will be described in further detail below. For example, the sensor assemblies may be used in instruments for applications in fields such as prosthetics, robotics, automotive, aerospace, mining, oil and gas, etc.

Referring now to FIG. 1A, an example embodiment of a catheter ablation system 10 is shown. The system 10 includes a console 12 and a catheter ablation instrument 14 having a flexible catheter shaft 20, an electrode tip 30, and a sensor assembly 100 having a body 110 with a front portion 200 and a rear portion 300. In the illustrated example embodiment, a proximal end 22 of the shaft 20 is coupled to the console 12. Different views of the sensor assembly 100 and/or the catheter ablation system 10 are shown in FIGS. 1B-8.

Referring now to FIGS. 1A to 1C, a distal end 24 of the shaft 20 can be rigidly affixed to a proximal end 302 of the rear portion 300 of the sensor body 110, and a proximal end 32 of the tip 30 can be rigidly affixed to a distal end 204 of the front portion 200 of the sensor body 110. The shaft 20 and the tip 30 can be affixed to the sensor body 110 such that the shaft 20 and the tip 30 extend from respective opposing ends 204, 302 of the sensor body 110 and any force or torque acting on the tip 30 is transferred to the sensor body 110.

The shaft 20 and the tip 30 can be affixed to the respective opposite ends 302, 204 of the sensor body 110 using, for example, micro screws, micro springs, micro clamps, swelling materials, adhesives, or through any other suitable means that allows for force and torque to be transferred from the tip 30 to the sensor body 110. In some embodiments, the shaft 20 and the tip 30 can be permanently affixed to the sensor body 110. In other embodiments, the shaft 20 and the tip 30 may be temporarily affixed to the sensor body 110, so that the sensor body 110 can be detached from the instrument 14 when not in use.

In some embodiments, the sensor body 110 may include only one of the front portion 200 and the rear portion 300. If only the front portion 200 is included, then the shaft 20 may be affixed to the proximal end 202 of the front portion 200 instead of the proximal end 302 of the rear portion 300. If only the rear portion 300 is included, then the tip 30 may be affixed to the distal end 304 of the rear portion 300 instead of the distal end 204 of the front portion 200.

The terms front, rear, proximal, and distal are used with respect to the sensor assembly 100 to denote the position of the elements described herein relative to the console 12 and the tip 30 as illustrated in FIG. 1. For example, as used throughout the description, a proximal (or rear) end, portion, or section of an element is nearer the console 12 and further from the tip 30 than the distal (or front) end, portion, or section of the element.

The terms front, rear, proximal, and distal are used for clarity, and are not meant to limit the orientation of the sensor body 110. For example, the sensor body 110, or one of the front portion 200 and the rear portion 300, may be oriented with respect to the shaft 20 and the tip 30 in an opposite direction than that illustrated. For example, the end 302 of the rear portion 300 may face the tip 30, the end 204 of the front portion 200 may face the shaft 20, or the positions of the front portion 200 and the rear portion 300 may be interchanged.

In the illustrated example embodiment, the front portion 200 and the rear portion 300 of the sensor body 110 are shown as separate components, with a distal end 304 of the rear portion 300 coupled to a proximal end 202 of the front portion 200. The front portion 200 and the rear portion 300 may be coupled together using, for example, micro screws, adhesives, or by any other suitable means that allows for force and torque transfer from the tip 30 through both the front portion 200 and the rear portion 300 of the sensor body 110. In other embodiments, rather than being separate components, the front portion 200 and the rear portion 300 may be formed integrally as one component.

The material for forming the sensor body 110 may vary depending on the particular application for which the sensor assembly 100 will be used. For example, the material may be selected based on the geometric properties of the sensor body 110, the range of forces, torques, and moments that may be exerted on the sensor body 110 during use, the temperatures to which the sensor body 110 may be subjected during use, and other appropriate considerations.

In some embodiments in which the sensor assembly 100 is used for MIS, the sensor body 110 may be made from a titanium alloy. A suitable titanium alloy may be Ti-6Al-4V due to this material's low young's modulus and high biocompatibility, corrosion resistance, strength, and fatigue resistance. The sensor body 110 may be fabricated from Ti-6Al-4V using micro-electric-discharge machining (micro-EDM), electron beam melting (EBM), laser beam melting (LBM), or by any other method that may provide material characteristics suitable for using the sensor assembly 100 as described herein.

In other embodiments, the sensor body 110 may be made from a polymeric material. Using a polymeric material may allow the sensor body 110 to be used in applications involving magnetic resonance imaging. A suitable polymeric material may be RGD-525 available from Stratasys Inc. (www.stratasys.com) due to this material's relatively high heat deflection temperature (HDT) of 63 to 67° C. at 0.45 MPa. The relatively high HDT of RGD-525 makes it suitable for use in catheter ablation applications during which the sensor body 110 may be exposed to temperatures of upwards of 50° C. The sensor body 110 may be fabricated from RGD-525 using, for example, rapid prototyping.

Referring now to FIGS. 1B and 1C, the sensor body 110 can define a longitudinal axis 111 extending between the opposing ends 204, 302 and through a center 113 of the sensor body 110. For clarity, the sensor body 110 is shown oriented and aligned with a set of orthogonal x, y, and z axes, with the z-axis defined by the axis 111 and defining an axial direction.

As shown in FIGS. 1B and 1C, and as described in more detail below, the sensor assembly 100 includes two groups of strain sensors 400a, 400b coupled to the front portion 200 of the sensor body 110 and positioned circumferentially about the axis 111, and two groups of strain sensors 400c, 400d coupled to the rear portion 300 of the sensor body 110 and positioned circumferentially about the axis 111.

In the illustrated example embodiment, the strain sensors 400a to 400d are conventional resistance type strain sensors, which can indicate strain by a change in resistance of a metal or a semiconductor. However, other types of strain sensors may be used in other embodiments. For example, as will be described with respect to FIGS. 9 to 12, fiber Bragg grating (FBG) type strain sensors may be used, which can indicate strain by a change in resonant wavelengths of FBGs formed on optical fibers.

Using FBG type strain sensors may be suitable where the sensor assembly 100 is to be used in applications involving magnetic resonance imaging, and may also allow for a reduction in the size of the sensor assembly 100. Using FBG type strain sensors may further provide for a lighter sensor assembly relative to sensor assemblies having resistance type strain sensors. Still further, a single optical fiber may transmit signals for multiple FBG type strain sensors, whereas each resistance type strain sensor generally requires a dedicated connection. As a result, relative to resistance type strains sensors, FBG type strain sensors may allow for simpler construction of strain sensor assemblies requiring multiple strain sensors connected in series.

Figure 1D:
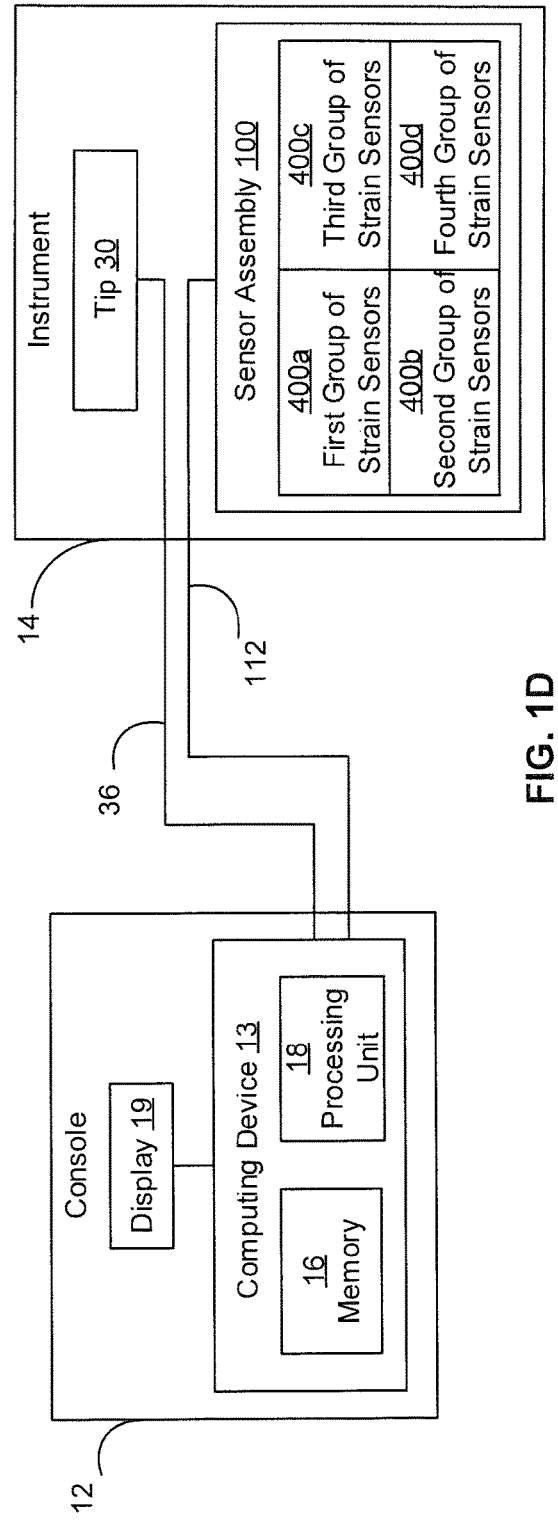
FIG. 1D is a block diagram of the catheter ablation system of FIG. 1A.

Referring now to FIGS. 1C and 1D, in some embodiments, sensor cabling 112 (shown schematically in FIG. 1D) may be coupled to and extend from the strain sensors in the groups 400a to 400d. The sensor cabling 112 may extend from the sensor assembly 100 to the console 12 through a lumen 26 (shown in FIG. 1C) extending longitudinally through the shaft 20. The sensor cabling 112 may transmit to the console 12 respective strain signals from the strain sensors in the groups 400*a* to 400*d*. The cabling 112 may comprise twisted-pair cables if resistance type strain sensors are used, or optical fibers if FBG type strain sensors are used.

In the illustrated example embodiment, the sensor body 110 includes a lumen 116 extending longitudinally through the front portion 200 and the rear portion 300. One or more electrode leads 36 (shown schematically in FIG. 1D), or other system components such as saline tubing, for example, may extend from the console 12 to the tip 30 through the lumen 26 of the shaft 20 and the lumen 116 of the sensor body 110. The electrode leads 36 may be used to transmit various electrical signals such as RF signals to the tip 30 for generating heat at a distal end 34 of the tip 30 to ablate heart tissue during surgery, for example.

In other embodiments for other applications, other components may extend through the lumen 116 of the sensor body 110. The components extending through the lumen 116 may vary depending on the type of instrument being used and the particular application for which the sensor assembly 100 is being used.

Referring now to FIG. 1D, the console 12 can include a computing device 13 having a memory 16 and one or more processing units 18. The computing device 13 can be configured to receive and process signals from the strain sensors in the groups 400*a* to 400*d*. The processing unit 18 can utilize software stored on the memory 16 for receiving and processing the strain signals, and for performing other functions related to operation of the instrument 14. The console 12 may further include, or be communicatively linked to, a display 19 and/or an actuator (not shown) for providing visual and/or haptic feedback of the surgical site and operation of the instrument 14 during surgery.

Figure 2:
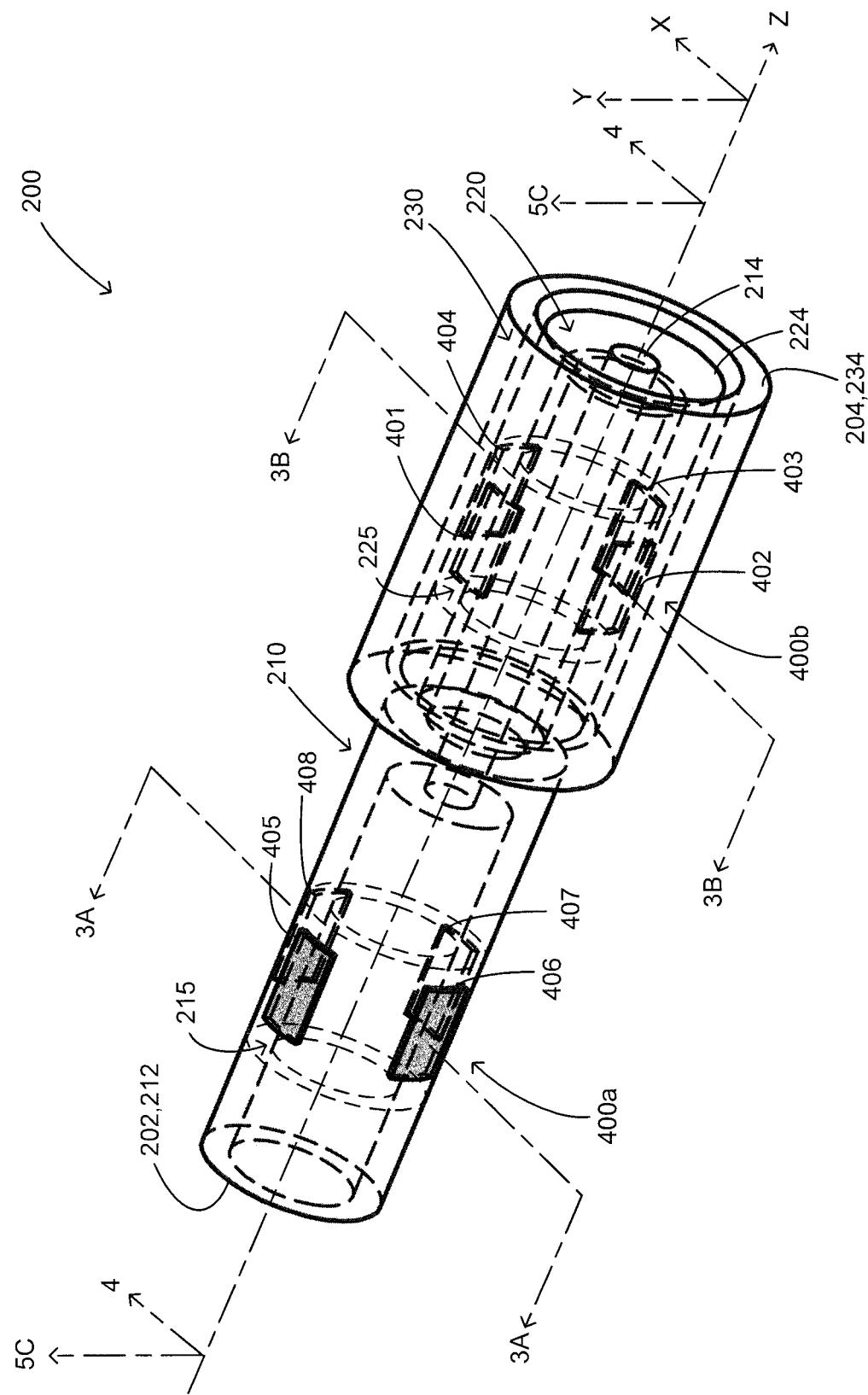
FIG. 2 is a perspective view of a front portion of the sensor assembly of FIG. 1A.
Figure 3A:
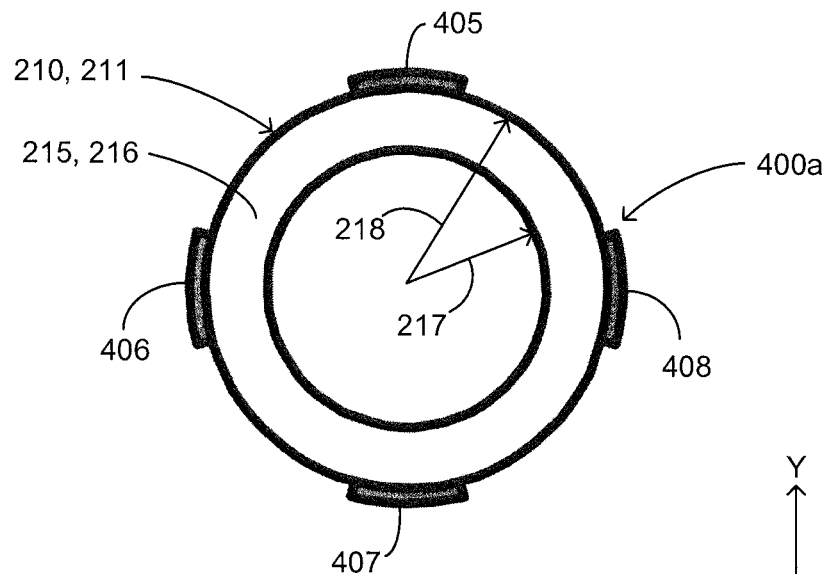
FIG. 3A is a cross section taken along line 3A-3A in FIG. 2.
Figure 3B:
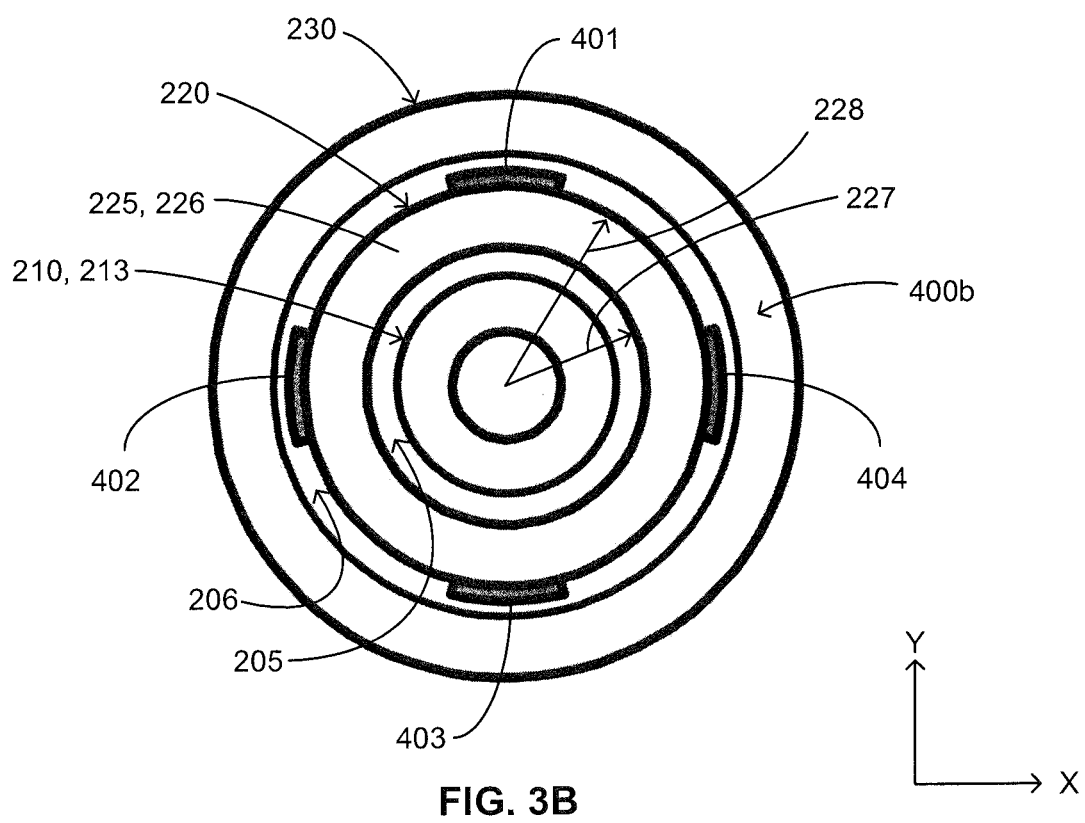
FIG. 3B is a cross section taken along line 3B-3B in FIG. 2.
Figure 4:
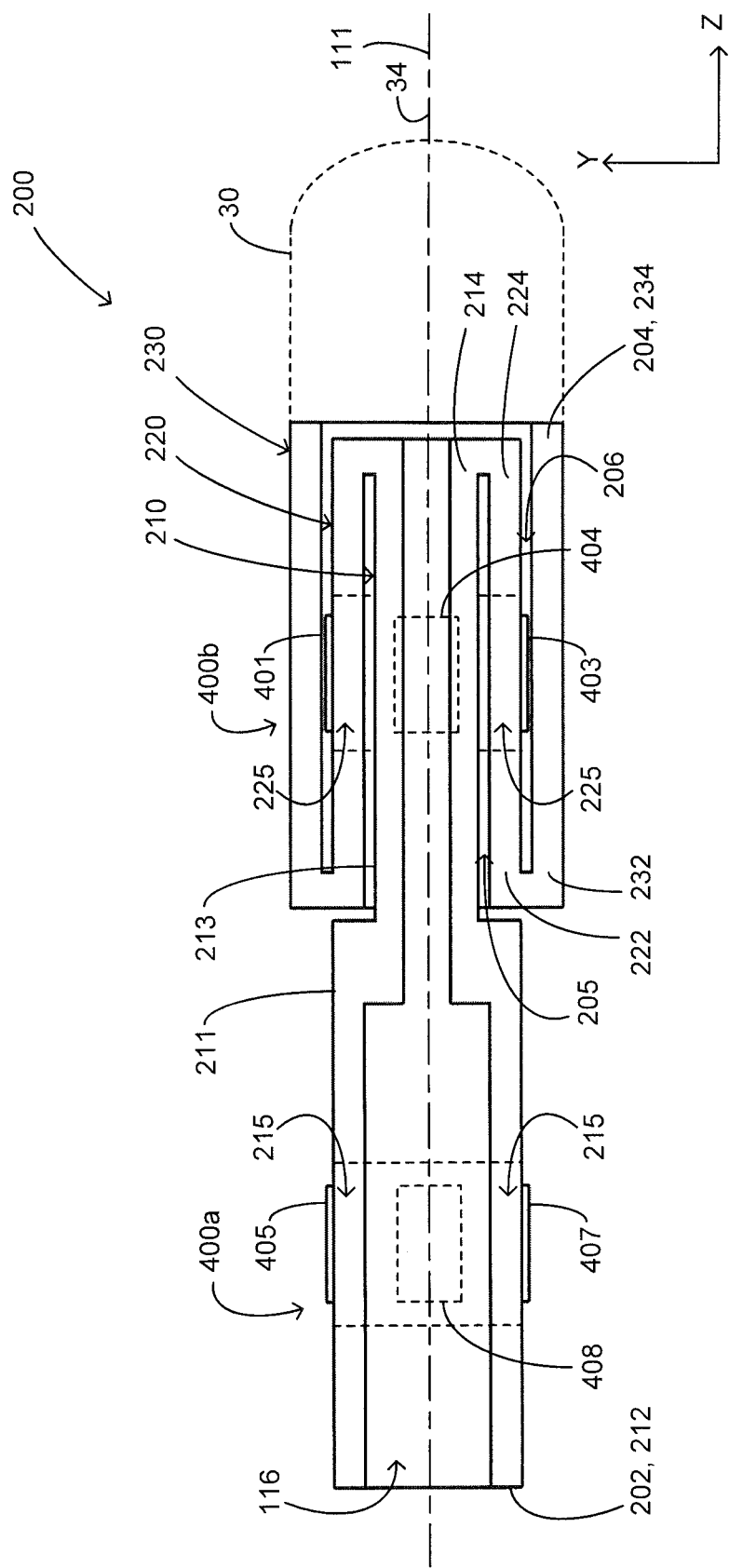
FIG. 4 is a cross section taken along line 4-4 in FIG. 2.

Referring now to FIGS. 2 to 4, the front portion 200 of the sensor body 110 and the groups of strain sensors 400*a*, 400*b* are shown. The front portion 200 and the groups of strain sensors 400*a*, 400*b* can operate to measure axial and lateral forces acting on the tip 30 of the instrument 14.

In the illustrated example embodiment, the front portion 200 includes three axially overlapping first, second, and third tubular members 210, 220, and 230, respectively. The tubular members 210, 220, 230 are oriented concentrically over one another and about the axis 111 of the sensor body 110. In the illustrated example embodiment, each of the tubular members 210, 220, 230 have a substantially circular cross section. In other embodiments, the tubular members 210, 220, 230 may have a substantially square cross section, a substantially elliptical cross section, or any other suitable cross section.

Referring now to FIGS. 2, 3A, and 4, the first member 210 includes a proximal section 211 and a distal section 213 having a diameter less than the diameter of the proximal section 211. The proximal section 211 can extend from a proximal end 212 of the first member 210 to the distal section 213. The distal section 213 can extend from the proximal section 211 to a distal end 214 of the first member 210. In the illustrated example embodiment, the proximal end 212 of the first member 210 defines the proximal end 202 of the front portion 200 of the sensor body 110, and is coupled to the shaft 20 through the rear portion 300 of the sensor body 110.

Referring now to FIGS. 3A and 4, the proximal section 211 can include a first strain sensor mounting region 215. The first region 215 can extend longitudinally along a length of the proximal section 211 and circumferentially about the axis 111, and can be defined by a cross sectional area 216 of the proximal section 211. As shown in FIG. 3A, the cross sectional area 216 can be defined by an inner radius 217 and an outer radius 218 of the proximal section 211 at the region 215.

Referring now to FIG. 4, the second member 220 is affixed at its distal end 224 to the distal end 214 of the first member 210. The second member 220 axially overlaps the distal section 213 of the first member 210, from the distal end 214 up to the proximal section 211 of the first member 210. An annular gap 205 can be provided between the first and second members 210, 220, so that the overlapping portions extending from the affixed distal ends 214, 224 of the first and second members 210, 220 are free to deform relative to one another in the axial direction.

Referring now to FIGS. 3B and 4, the second member 220 can include a second strain sensor mounting region 225. The second region 225 can extend longitudinally along a length of the second member 220 and circumferentially about the axis 111, and can be defined by a cross sectional area 226 of the second member. As shown in FIG. 3B, the cross sectional area 226 can be defined by an inner radius 227 and an outer radius 228 of the second member 220 at the region 225.

Referring now to FIGS. 3A and 3B, the first cross sectional area 216 of the first region 215 can be substantially equal to the second cross sectional 226 area of the second region 225, with the first inner and outer radii 217, 218 of the first region 215 being substantially equal to the second inner and outer radii 227, 228, respectively, of the second region 225. Manufacturing the sensor body 110 so that the first and second regions 215, 225 have substantially equal cross sectional areas and inner and outer radii may allow for simplicity in resolving axial and lateral forces acting at the tip 30.

In other embodiments, the first and second cross sectional areas 216, 226 may be substantially equal, but the first inner and outer radii 217, 218 may be different from the second inner and outer radii 227, 228, respectively.

In other embodiments, the first and second cross sectional areas 216, 226 may be different, with one or both of the first inner and outer radii 217, 218 being different from one or both of the second inner and outer radii 227, 228, respectively.

Referring now to FIG. 4, the second member 220 can be coupled at its proximal end 222 to the tip 30 of the instrument 14 through the third member 230. In the illustrated example embodiment, the third member 230 is affixed at its proximal end 232 to the proximal end 222 of the second member 220. The third member 230 can axially overlap the length of the second member 220, with a distal end 234 of the third member 230 extending past the distal ends 214, 224 of the first and second members 210, 220. In the illustrated example embodiment, the distal end 234 of the third member 230 is affixed to the tip 30 of the instrument 14 and defines the distal end 204 of the front portion 200. An annular gap 206 can be provided between the second and third members 220, 230, so that the overlapping portions extending from the affixed proximal ends 222, 232 of the second and third members 220, 230 are free to deform relative to one another in the axial direction.

In other embodiments, the third member 230 may be omitted, and the proximal end 222 of the second member 220 may be directly or indirectly coupled to the tip 30 of the instrument 14 through other means that allows for force and torque to be transferred form the tip 30 to the second member 220.

In the illustrated example embodiment, the tubular members 210, 220, 230 are formed integrally as one component. In other embodiments, the tubular members 210, 220, 230 may be separate components that are affixed to one another through, for example, micro screws, adhesives, or through any other suitable means that allows for force and torque to be transferred from the tip 30 to each of the members 210, 220, 230.

Referring now to FIGS. 2 to 4, the first group of strain sensors 400a comprises four strain sensors 405, 406, 407, and 408, and the second group of strain sensors 400b comprises an equal number of strain sensors 401, 402, 403, and 404. The first group of strain sensors 400a can be mounted to the proximal section 211 of the first member 210 at the first region 215, and the second group of strain sensors 400b can be mounted to the second member 220 at the second region 225.

In some embodiments, additional or fewer strain sensors may be included in each group 400a, 400b. In some embodiments, each group of strain sensors 400a, 400b may include, for example, 3 strain sensors. In other embodiments in which the sensor assembly 100 is used in applications in which only axial forces act on the tip 30 of the instrument 14 along the axis 111, each group of strain sensors 400a, 400b may include a single strain sensor. To allow for simplicity and increased accuracy in resolving axial or lateral forces independent of steady state temperature variations, the number of strain sensors in the first group 400a can be equal to the number of strain sensors in the second group 400b.

Referring now to FIGS. 3A and 3B, the strain sensors in each of the first and second groups 400a, 400b are spaced equidistantly about the axis 111 and are about 90 degrees apart. In other embodiments in which each group of strain sensors 400a, 400b includes 3 strain sensors, the strain sensors of each group 400a, 400b may be spaced about 120 degrees apart.

As shown in FIGS. 2 to 4, the strain sensors 401, 402, 403, and 404 are oriented at substantially the same angle about the axis 111 as the strain sensors 405, 406, 407, and 408, respectively. Orienting the strain sensors such that each strain sensor of the first group 400a is oriented at substantially the same angle about the axis 111 as a strain sensor of the second group 400b can allow for simplicity in resolving lateral forces acting at the tip 30. As will be described with reference to FIGS. 9 to 11, in examples in which FBG type strain sensors are used, orienting the strain sensors in this manner may also minimize the number of required optical fibers.

Each strain sensor of the first group 400a can be oriented and configured to measure axial strain of the proximal section 211 at the first region 215, and each sensor of the second group 400b can be oriented and configured to measure axial strain of the second member 220 at the second region 225. That is, the primary strain sensing direction of each strain sensor 401, 402, 403, 404, 405, 406, 407, and 408 is oriented parallel to the axis 111 (i.e., the z-axis) of the sensor body 110. The strain sensors 401, 402, 403, 404, 405, 406, 407, 408 can be configured to provide strain signals $\epsilon 1$, $\epsilon 2$, $\epsilon 3$, $\epsilon 4$, $\epsilon 5$, $\epsilon 6$, $\epsilon 7$, $\epsilon 8$, respectively, corresponding to axial strains at the respective first and second regions 215, 225.

As will now be described with reference to FIGS. 5A to 5C, some or all of the strain signals $\epsilon 1$, $\epsilon 2$, $\epsilon 3$, $\epsilon 4$, $\epsilon 5$, $\epsilon 6$, $\epsilon 7$, $\epsilon 8$ may be combined arithmetically to resolve axial and lateral forces acting on the tip 30 of the instrument 14. Furthermore, the locations and relative positions of the strain sensors 401 to 408 allow for the axial and lateral forces to be resolved independent of steady state temperature variations.

Figure 5A:
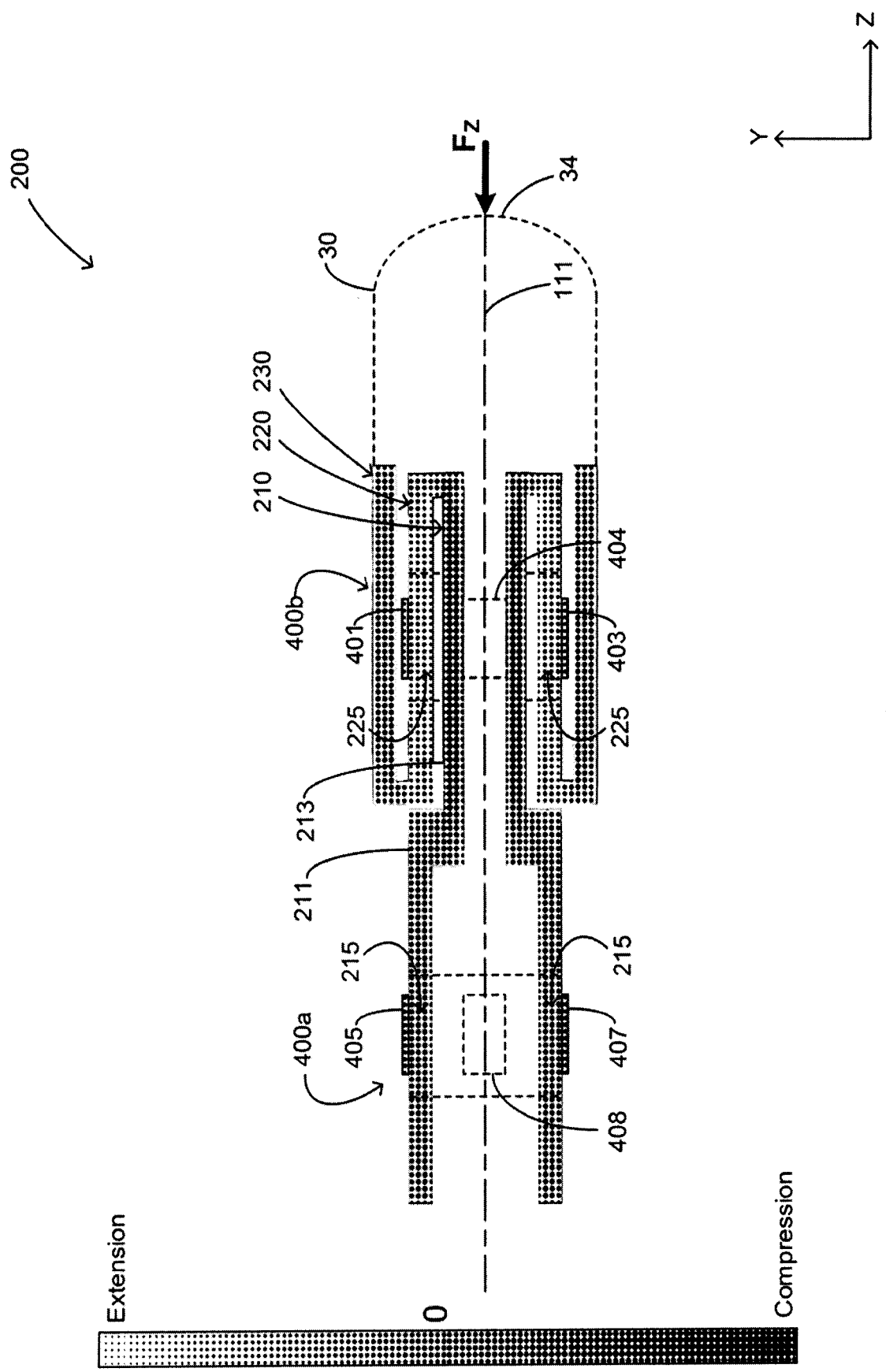
FIG. 5A is a cross section taken along line 4-4 in FIG. 2 showing deformation of the front portion resulting from an axial force.

Referring now to FIG. 5A, the front portion 200 of the sensor body 110 is shown with exaggerated deformation of the tubular members 210, 220, 230 resulting from an axial force Fz acting on the tip 30 of the instrument 14 along the axis 111.

As shown in the illustrated example embodiment, in response to the axial force Fz, the first member 210 experiences axial compression at the first region 215 and the second member 220 experiences axial extension at the second region 225. In other embodiments in which the axial force Fz acts on the tip 30 in an opposite direction, the first region 215 may experience axial extension while the second region 225 experiences axial compression.

In response to the deformation, the strain sensors 405, 406, 407, 408 may provide strain signals $\epsilon 5$, $\epsilon 6$, $\epsilon 7$, $\epsilon 8$, respectively, corresponding to the compressive axial strain resulting from the axial compression of the first region 215. At the same time, the strain sensors 401, 402, 403, 404 may provide strain signals $\epsilon 1$, $\epsilon 2$, $\epsilon 3$, $\epsilon 4$, respectively, corresponding to the tensile axial strain resulting from the axial extension of the second region 225.

As a result of the strain signals $\epsilon 5$, $\epsilon 6$, $\epsilon 7$, $\epsilon 8$ corresponding to compressive axial strains and the strain signals $\epsilon 1$, $\epsilon 2$, $\epsilon 3$, $\epsilon 4$ corresponding to tensile axial strains, the strain signals $\epsilon 1$ to $\epsilon 8$ may be combined in various sums and differences to cancel out common thermal strains resulting from steady state temperature variations. In this way, the axial force Fz can be resolved based on the strain signals $\epsilon 1$ to $\epsilon 8$ independent of steady state temperature variations.

In the illustrated example embodiment, the cross sectional areas 216, 226 of the first and second regions 215, 225 are substantially similar. In this case, the axial force Fz can be resolved based on the equation Fz=$\alpha(\epsilon B - \epsilon A)$, where $\epsilon A$ is the sum of the strain signals provided by the first group of strain sensors 400a; $\epsilon B$ is the sum of the strain signals provided by the second group of strain sensors 400b; and a is a function of the number of respective strain signals provided, and the material characteristics and cross sectional areas 216, 226 of the first and second regions 215, 225.

In the illustrated example embodiment, $\epsilon A$ can equal ($\epsilon 5+\epsilon 6+\epsilon 7+\epsilon 8$); $\epsilon B$ can equal ($\epsilon 1+\epsilon 2+\epsilon 3+\epsilon 4$); and $\alpha$ can equal $$\frac{EA}{n},$$

where E is the modulus of elasticity in the axial direction of the material used for the first and second regions 215, 225, n is the number of respective strain signals provided, and A is the cross sectional area 216 of the first region 215 or the substantially similar cross sectional area 226 of the second region 225. Accordingly, the axial force Fz can be resolved based on the equation $$Fz = \frac{EA}{8}(\epsilon 1 + \epsilon 2 + \epsilon 3 + \epsilon 4 - \epsilon 5 - \epsilon 6 - \epsilon 7 - \epsilon 8).$$

By adding an equal thermal strain to each of the strain signals $\epsilon 1$ to $\epsilon 8$, it can be seen that common thermal strains resulting from steady state temperature variations are cancelled out when resolving the axial force Fz using the above equation. As a result of the orientation and position of the strain sensors 401 to 408, axial strains resulting from lateral forces are also cancelled out when resolving the axial force Fz using the above equation.

In other embodiments, additional or fewer strain signals may be used to resolve the axial force Fz independent of steady state temperature variations. For example, the axial force Fz may be resolved using one strain signal from the first group of strain sensors 400a and one strain signal from the second group of strain sensors 400b. For example, the axial force Fz may be resolved based on the equation $$Fz = \frac{EA}{2}(\epsilon B - \epsilon A),$$

where ($\epsilon B - \epsilon A$) is equal to one of ($\epsilon 1-\epsilon 5$), ($\epsilon 1-\epsilon 7$), ($\epsilon 2-\epsilon 6$), ($\epsilon 2-\epsilon 8$), ($\epsilon 4-\epsilon 8$), etc. Such simplification may remove the ability to distinguish between axial strains resulting from the axial force Fz and those resulting from lateral forces, but may nonetheless be useful in applications in which predominantly axial forces act on the tip 30 along the axis 111.

In other embodiments, the cross sectional areas 216, 226 of the first and second regions 215, 225 may be different. In this case, the axial force Fz can be resolved based on the equation $$\frac{E}{n}(A2(\epsilon B) - A1(\epsilon A)),$$

where E is the modulus of elasticity in the axial direction of the material used for the first and second regions 215, 225; n is the number of respective strain signals provided; A1 is the cross sectional area 216 of the first region 215; A2 is the cross sectional area 226 of the second region 225; $\epsilon A$ is the sum of the strain signals provided by the first group of strain sensors 400a; and $\epsilon B$ is the sum of the strain signals provided by the second group of strain sensors 400b.

Figure 5B:
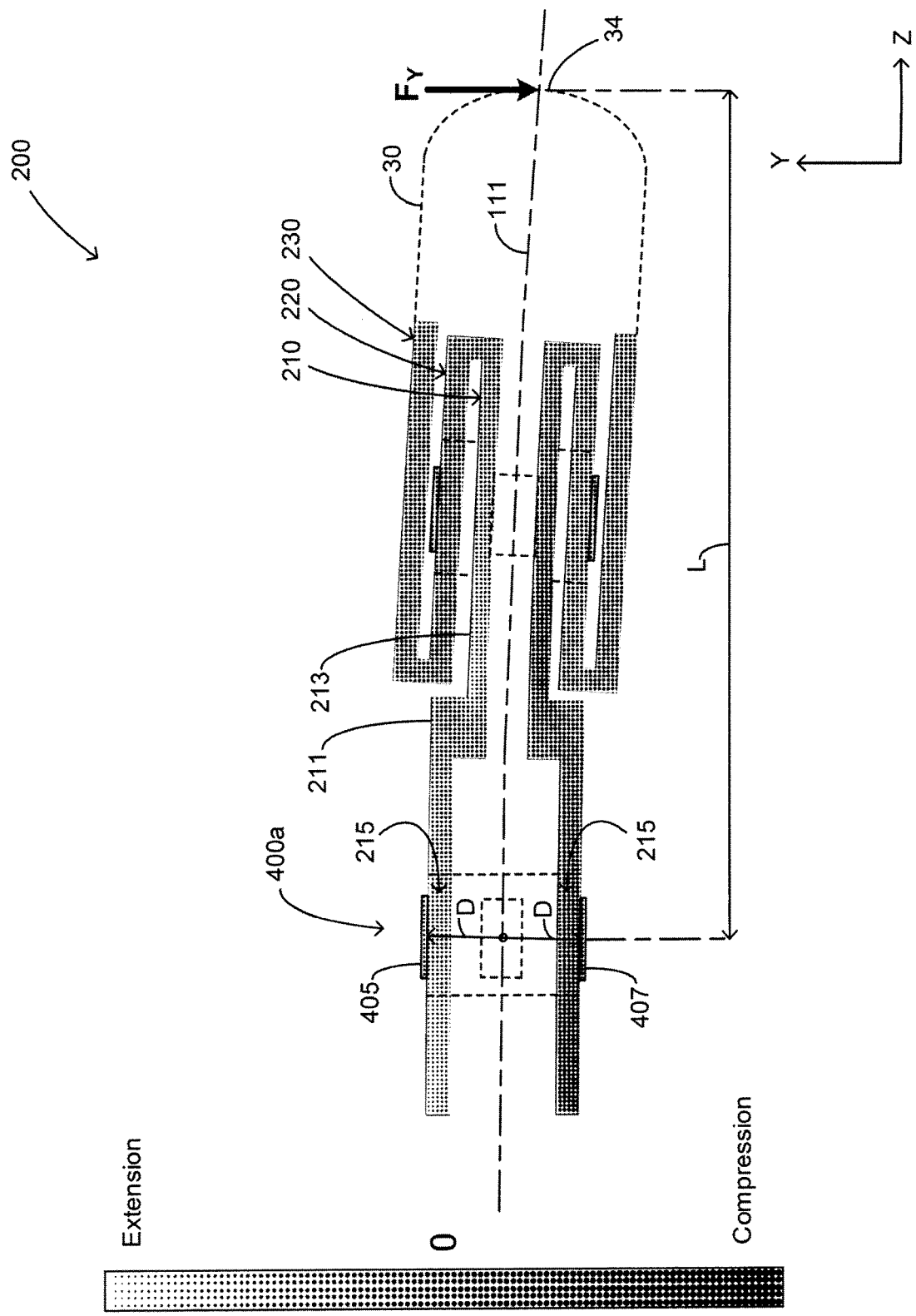
FIG. 5B is a cross section taken along line 4-4 in FIG. 2 showing deformation of the front portion resulting from a lateral force.

Referring now to FIG. 5B, the front portion 200 of the sensor body 110 is shown with exaggerated deformation of the tubular members 210, 220, 230 resulting from a lateral force Fy acting on the tip 30.

As shown in the illustrated example embodiment, in response to the lateral force Fy, the portion of the first region 215 at which the strain sensor 405 is mounted experiences axial extension and the diametrically opposed portion of the first region 215 at which the strain sensor 407 is mounted experiences axial compression. In other embodiments, in which the lateral force Fy acts on the tip 30 in an opposite direction, the portion of the first region 215 at which the strain sensor 405 is mounted may experience axial compression and the portion of the first region 215 at which the strain sensor 407 is mounted may experience axial extension.

In response to the deformation, the strain sensor 405 may provide a strain signal $\epsilon 5$ corresponding to tensile axial strain resulting from the axial extension. At the same time, the strain sensor 407 may provide a strain signal $\epsilon 7$ corresponding to compressive axial strain resulting from the axial compression. As a result of the strain signal $\epsilon 5$ corresponding to tensile axial strain and the strain signal $\epsilon 7$ corresponding to compressive axial strain, the strain signals $\epsilon 5$, $\epsilon 7$ may be combined to cancel out common thermal strains resulting from steady state temperature variations. In this way, the lateral force Fy can be resolved based on the strain signals $\epsilon 5$, $\epsilon 7$ independent of steady state temperature variations.

In the illustrated example embodiment, the lateral force Fy may be resolved based on the equation $$Fy = \frac{\gamma}{2}(\epsilon 5 - \epsilon 7),$$

where $\gamma$ is a function of the geometry and material characteristics of the first region 215; the distance from the axis 111 to the acting plane of each of the strain sensors 405, 407; and the distance from the strain sensors 405, 407 to the distal end 34 of the tip 30 at which the lateral force Fy is acting.

In the illustrated example embodiment, $\gamma$ can equal $$\frac{EI}{DL},$$

where E is the modulus of elasticity in the axial direction of the material of the first region 215; I is the section moment of inertia of the first region 215; D is the distance from the axis 111 to the acting plane of each of the strain sensors 405, 407; and L is the distance from the middle of the strain sensors 405, 407 to the distal end 34 of the tip 30 at which the lateral force Fy is acting. Accordingly, the lateral force Fy can be resolved based on the equation $$Fy = \left(\frac{EI}{2DL}\right)(\epsilon 5 - \epsilon 7).$$

By adding an equal thermal strain to the strain signals $\epsilon 5$, $\epsilon 7$, it can be seen that common thermal strains resulting from steady state temperature variations are cancelled out when resolving the lateral force Fy using the above equation. As a result of the orientation and position of the strain sensors 405, 407, axial strains resulting from an axial force are also cancelled out when resolving the lateral force Fy using the above equation.

Based on the lateral force Fy, the bending moment Mx acting on the instrument 14 about the x-axis may also be resolved. For example, to measure the bending moment Mx at a point of interest along the axis 111, the resolved lateral force Fy can be multiplied by a distance from the point of interest to the distal end 34 of the tip 30 at which the lateral force Fy is acting.

Figure 5C:
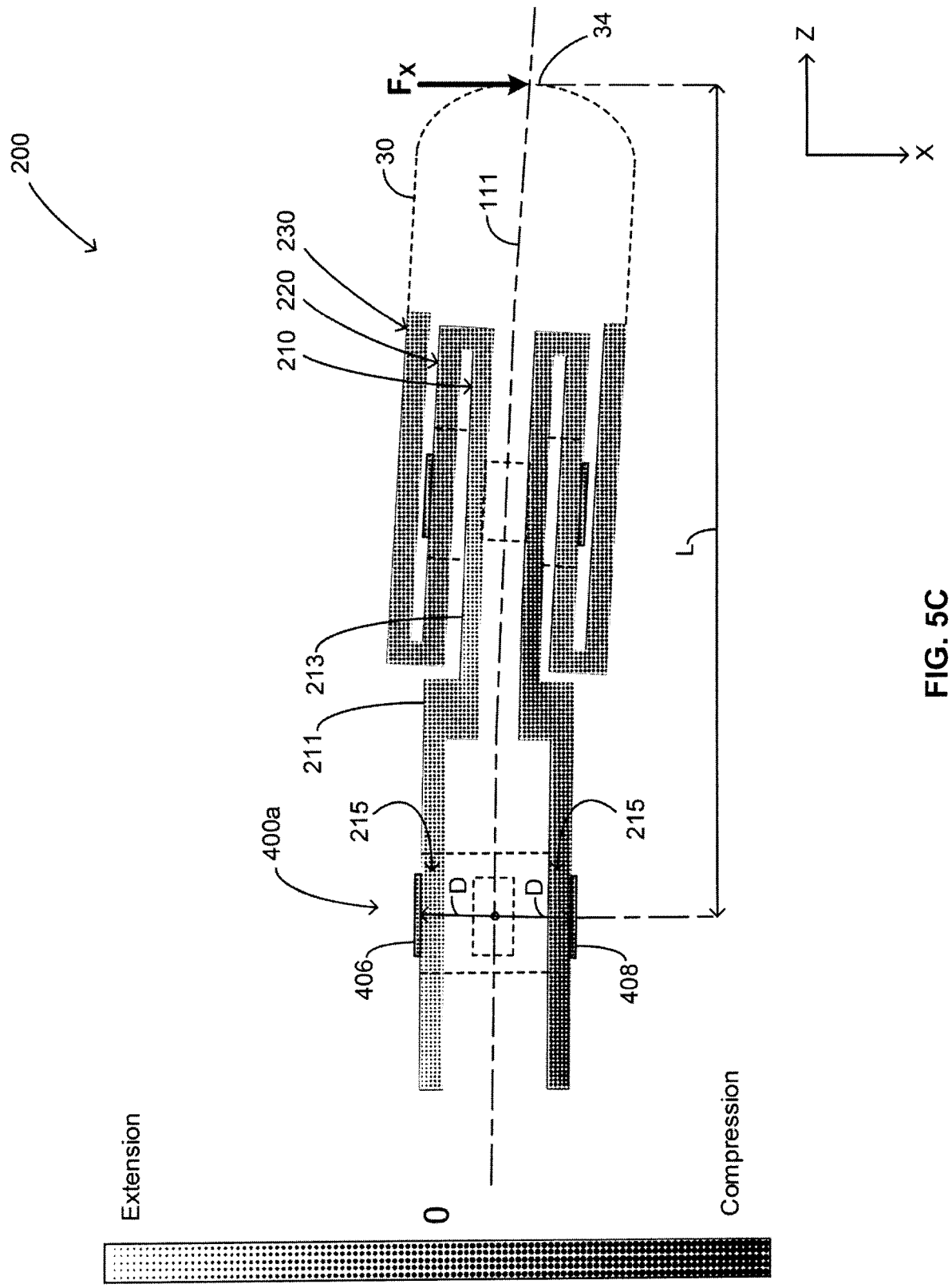
FIG. 5C is a cross section taken along line 5C-5C in FIG. 2 showing deformation of the front portion resulting from another lateral force.

Referring now to FIG. 5C, the front portion 200 of the sensor body 110 is shown with exaggerated deformation of the tubular members 210, 220, 230 resulting from a lateral force Fx acting on the tip 30.

As shown in the illustrated example embodiment, in response to the lateral force Fx, the portion of the first region 215 at which the strain sensor 406 is mounted experiences axial extension and the diametrically opposed portion of the first region 215 at which the strain sensor 408 is mounted experiences axial compression. In other embodiments in which the lateral force Fx acts on the tip 30 in an opposite direction, the portion of the first region 215 at which the strain sensor 406 is mounted may experience axial compression and the portion of the first region 215 at which the strain sensor 408 is mounted may experience axial extension.

In response to the deformation, the strain sensor 406 may provide a strain signal $\epsilon 6$ corresponding to tensile axial strain resulting from the axial extension. At the same time, the strain sensor 408 may provide a strain signal $\epsilon 8$ corresponding to compressive axial strain resulting from the axial compression. As a result of the strain signal ϵ6 corresponding to tensile axial strain and the strain signal ϵ8 corresponding to compressive axial strain, the strain signals ϵ6, ϵ8 may be combined to cancel out common thermal strains resulting from steady state temperature variations. In this way, the lateral force Fx can be resolved based on the strain signals ϵ6, ϵ8 independent of steady state temperature variations.

In the illustrated example embodiment, the lateral force Fx can be resolved based on the equation $$Fx = \frac{\chi}{2}(\epsilon 6 - \epsilon 8),$$

where $\chi$ is a function of the geometry and material characteristics of the first region 215, the distance from the axis 111 to the acting plane of the strain sensors 406, 408, and the distance from the strain sensors 406, 408 to the distal end 34 of the tip 30 at which the lateral force Fx is acting.

In the illustrated example embodiment, $\chi$ can equal $$\frac{EI}{DL},$$

where E is the modulus of elasticity in the axial direction of the material of the first region 215; I is the section moment of inertia of the first region 215; D is the distance from the axis 111 to the acting plane of the strain sensors 406, 408; and L is the distance from the strain sensors 406, 408 to the distal end 34 of the tip 30 at which the lateral force Fx is acting. Accordingly, the lateral force Fx can be resolved based on the equation $$Fx = \left(\frac{EI}{2DL}\right)(\epsilon 6 - \epsilon 8).$$

By adding an equal thermal strain to the strain signals ϵ6, ϵ8, it can be seen that common thermal strains resulting from steady state temperature variations are cancelled out when resolving the lateral force Fx using the above equation. As a result of the orientation and position of the strain sensors 406, 408, axial strains resulting from an axial force are also cancelled out when resolving the lateral force Fx using the above equation.

Based on the lateral force Fx, the bending moment My acting on the instrument 14 about the y-axis may also be resolved. For example, to measure the bending moment My at a point of interest along the axis 111, the resolved lateral force Fx can be multiplied by a distance from the point of interest to the distal end 34 of the tip 30 at which the lateral force Fx is acting.

Figure 6:
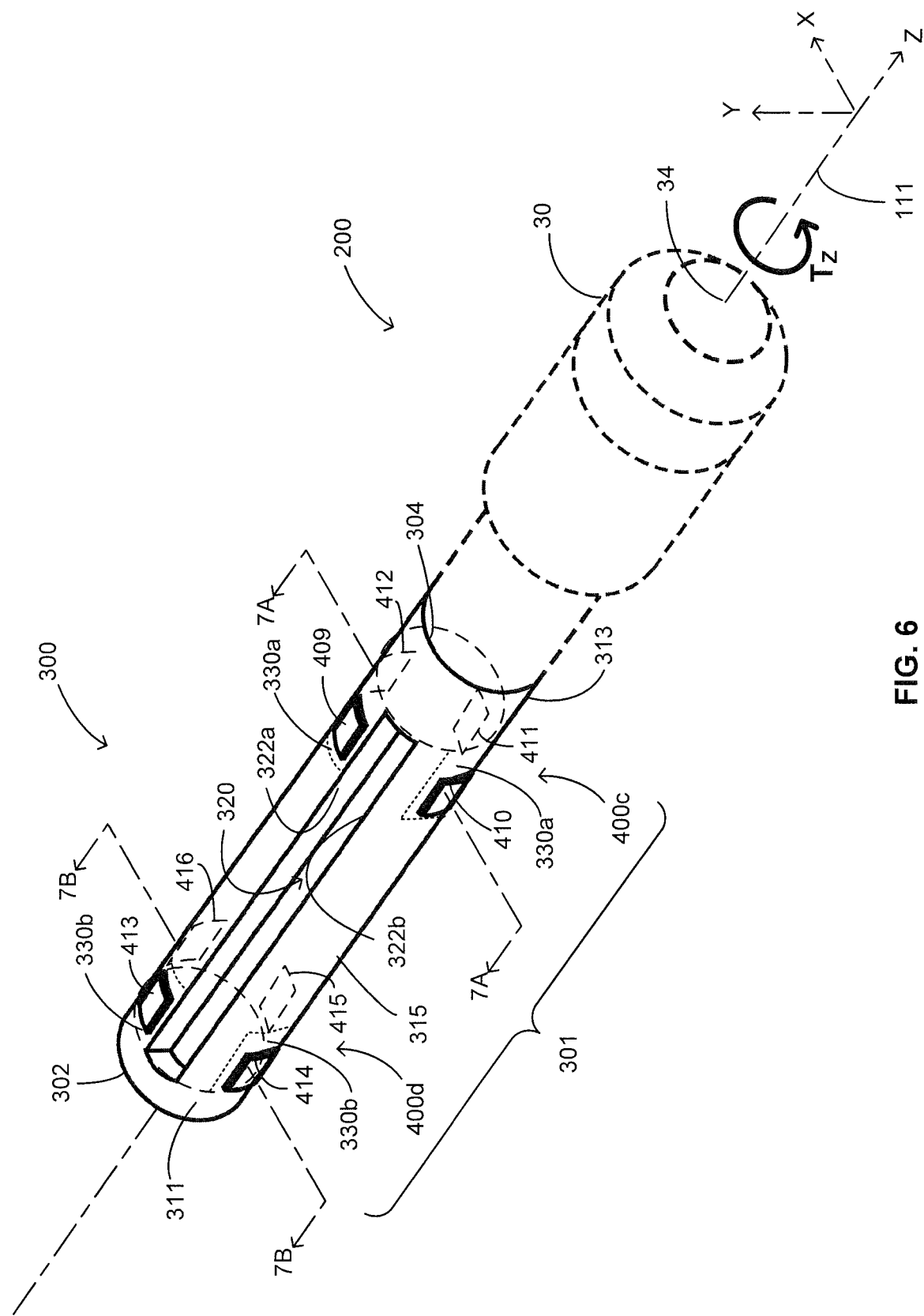
FIG. 6 is a perspective view of the rear portion of the sensor assembly of FIG. 1.
Figure 7A:
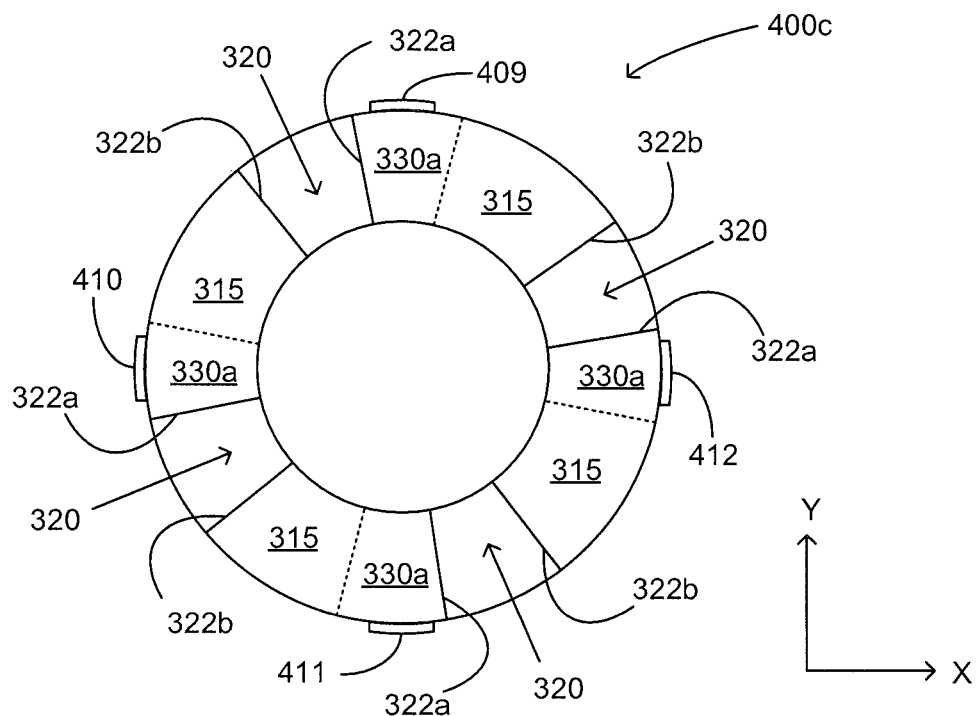
FIG. 7A is a cross section taken along line 7A-7A in FIG. 6.
Figure 7B:
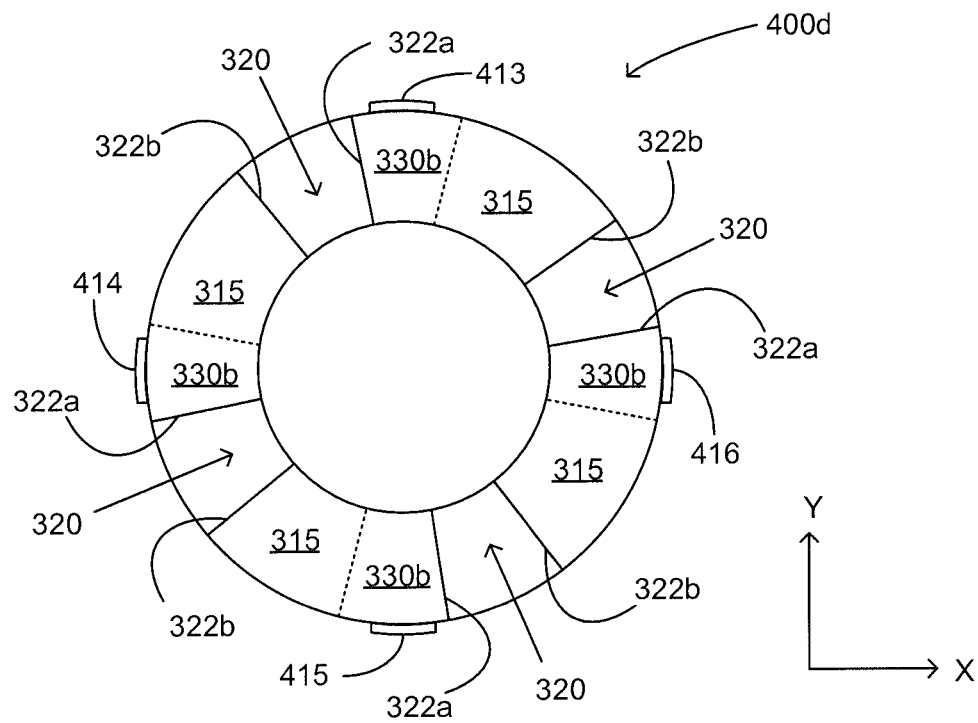
FIG. 7B is a cross section taken along line 7B-7B in FIG. 6.

Referring now to FIGS. 6, 7A, and 7B, the rear portion 300 of the sensor body 110 and the groups of strain sensors 400c, 400d are shown. The rear portion 300 and the groups of strain sensors 400c, 400d can operate to measure axial torque acting on the tip 30 of the instrument 14 about the axis 111.

In the illustrated example embodiment, the rear portion 300 includes a substantially tubular body 301 oriented concentrically about the axis 111 and having the proximal end 302 and a distal end 304. As noted above, the proximal end 302 may be affixed to the shaft 20 of the instrument 14. The distal end 304 may be affixed to the front portion 200 of the sensor body 110 and coupled to the tip 30 of the instrument 14 through the front portion 200.

In the illustrated example embodiment, the body 301 includes a proximal portion 311 extending inwardly from the proximal end 302, a distal portion 313 extending inwardly from the distal end 304, and a central side wall 315 extending about the axis 111 between the proximal portion 311 and the distal portion 313.

In the illustrated example embodiment, the body 301 further includes four elongated slits 320 extending parallel to and spaced equidistantly about the axis 111. Each slit 320 extends through the central side wall 315 to the lumen 116 of the sensor body 110 and can be defined by respective opposing first and second longitudinal side faces 322a, 322b. The first and second side faces 322a, 322b extend between the proximal portion 311 and the distal portion 313 of the body 301.

Although the slits 320 are shown having a generally rectangular shape, in other embodiments, the slits 320 may have a different shape, such as an elongated elliptical shape. Further, in other embodiments, the body 301 may include a different number of slits 320 such as, for example, two or three slits 320. In other embodiments, as opposed to extending parallel to the axis 111, the slits 320 may be arranged in a spiral configuration about the axis 111.

In the illustrated example embodiment, the central side wall 315 includes four first strain sensor mounting regions 330a and four second strain sensor mounting regions 330b. The location of the first and second regions 330a, 330b can correspond to locations on the body 301 that experience opposing axial strains in response to an axial torque acting on the tip 30 about the axis 111.

Figure 8:
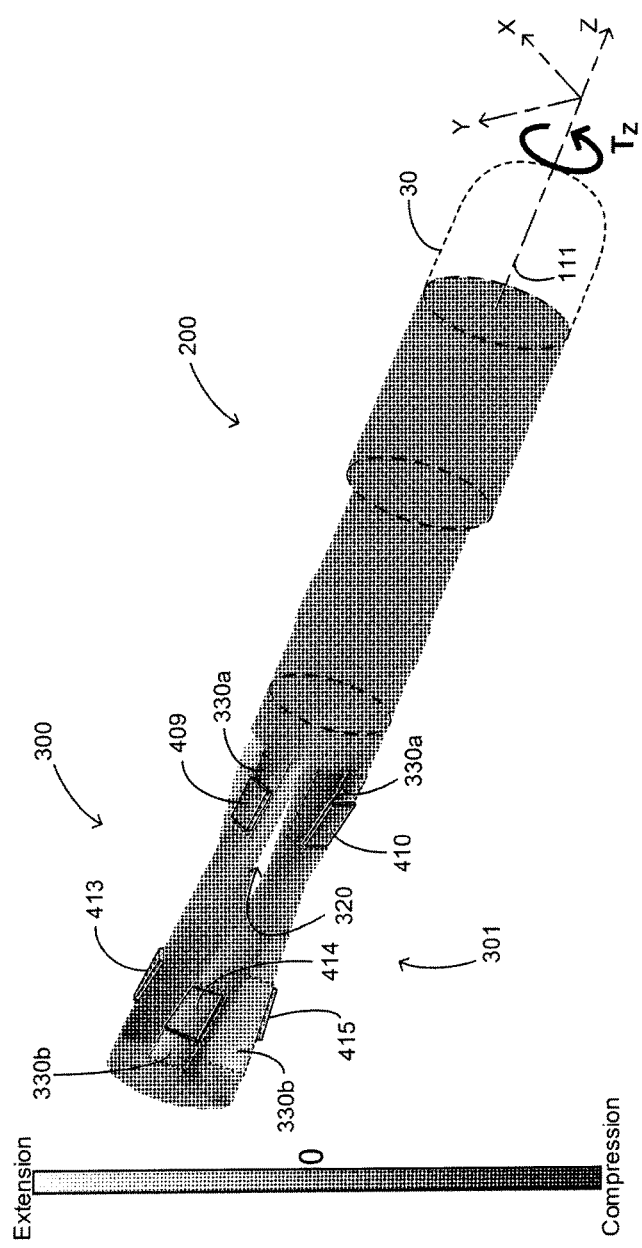
FIG. 8 is a perspective view of the rear portion of FIG. 6 showing deformation of the rear portion resulting from an axial torque.

For example, as shown in FIG. 8, each first region 330a can correspond to a portion of the body 301 that experiences axial compression in response to an axial torque acting on the tip 30 about the axis 111. In this case, each second region 330b can correspond to a portion of the body 301 that experiences axial extension in response to the axial torque.

In FIGS. 6 to 8, in the illustrated example embodiment, the first and second regions 330a, 330b are located on the central side wall 315 near longitudinally opposing vertices of the slit 320. Specifically, each first region 330a is located near the distal portion 313 of the body 301 and a respective first side face 322a of a respective slit 320. Each second region 330b is located near the proximal portion 311 of the body 301 and a respective first side face 322a of a respective slit 320. Each of the first and second regions 330a, 330b extend from respective first side faces 322a through a portion of the central side wall 315 toward the midway point between the first side face 322a and a second side face 322b of a neighboring slit 320.

In other embodiments the location of the first and second regions 330a, 330b may vary. For example, the first and second regions 330a, 330b may instead be located near circumferentially opposing vertices of the slits 320. For example, each first region 330a may be located as described above, but each second region 330b may be located on the central side wall 315 near the distal portion 313 of the body 301 and a respective second side face 322b. In other embodiments, the first and second regions 330a, 330b may be located on the central side wall 315 near the proximal portion 311 of the body 301 and near opposite longitudinal side faces 322a, 322b. The number of first regions 330a and the number of second regions 330b can correspond to the number of slits 320 in the body 301. For example, in other embodiments in which the body includes two slits 320, the central side wall 315 may include two first regions 330a and two second regions 330b located as described above.

Similarly, the number of strain sensors in each of the third group 400c and the fourth group 400d may also correspond to the number of slits 320 in the body 301. In the illustrated example embodiment, the third group of strain sensors 400c comprises four strain sensors 409, 410, 411, and 412, and the fourth group of strain sensors 400d comprises an equal number of strain sensors 413, 414, 415, and 416. In some embodiments, additional or fewer strain sensors may be included in each group 400c, 400d. For example, in some embodiments in which three slits 320 are provided, each group of strain sensors 400c, 400d may include 3 strain sensors.

In other embodiments in which the sensor assembly 100 is used in applications in which only an axial torque acts on the tip 30 of the instrument 14 about the axis 111, each group of strain sensors 400c, 400d may include a single strain sensor. In such examples, the body 301 may include a single slit 320.

In the illustrated example embodiment, each of the strain sensors 409, 410, 411, and 412 is mounted to a respective first region 330a, and each of the strain sensors 413, 414, 415, 416 is mounted to a respective second region 330b.

Referring now to FIGS. 7A and 7B, the strain sensors in each of the groups 400c, 400d are spaced equidistantly about the axis 111 and 90 degrees apart. In other embodiments in which the body 301 includes three slits 320, each group of strain sensors 400c, 400d may include 3 strain sensors, with the slits 320 and the strain sensors in each group 400c, 400d spaced 120 degrees apart.

As shown in FIGS. 6, 7A, and 7B, the strain sensors 409, 410, 411, 412 are oriented at substantially the same angle about the axis 111 as the strain sensors 413, 414, 415, 416, respectively. Orienting the strain sensors in this manner may allow for simplicity in resolving axial torque acting on the tip 30. As will be described with reference to FIGS. 9 to 11, in embodiments in which FBG type strain sensors are used, orienting the strain sensors in this manner may also minimize the number of required optical fibers.

Each strain sensor of the third group 400c can be oriented and configured to measure axial strain at a respective first region 330a, and each sensor of the fourth group 400d can be oriented and configured to measure axial strain at a respective second region 330b. That is, the primary strain sensing direction of each strain sensor 409, 410, 411, 412, 413, 414, 415, 416 is oriented parallel to the axis 111 (z-axis) of the sensor body 110. The strain sensors 409, 410, 411, 412, 413, 414, 415, 416 can be configured to provide strain signals $\epsilon9$, $\epsilon10$, $\epsilon11$, $\epsilon12$, $\epsilon13$, $\epsilon14$, $\epsilon15$, $\epsilon16$, respectively, corresponding to axial strains at the respective first and second regions 330a, 330b.

As will now be described with reference to FIG. 8, some or all of the strain signals $\epsilon9$, $\epsilon10$, $\epsilon11$, $\epsilon12$, $\epsilon13$, $\epsilon14$, $\epsilon15$, $\epsilon16$ may be combined arithmetically to resolve axial torque acting on the tip 30 of the instrument 14. The axial torque may be resolved independent of steady state temperature variations.

Referring now to FIG. 8, the rear portion 300 of the sensor body 110 is shown with exaggerated deformation resulting from an axial torque Tz acting on the tip 30 of the instrument 14 about the axis 111.

As shown in the illustrated example embodiment, as a result of the body 301 having the slits 320, in response to the axial torque Tz acting on the tip 30, each first region 330a experiences axial compression and each second region 330b experiences axial extension. In other embodiments in which the axial torque Tz acts on the tip 30 of the instrument 14 in an opposite direction, each first region 330a may experience axial extension while each second region 330b may experience axial compression.

In response to the deformation, the strain sensors 409, 410, 411, 412 may provide strain signals $\epsilon9$, $\epsilon10$, $\epsilon11$, $\epsilon12$, respectively, corresponding to compressive axial strains resulting from the axial compression at the respective first regions 330a. At the same time, the strain sensors 413, 414, 415, 416 may provide strain signals $\epsilon13$, $\epsilon14$, $\epsilon15$, $\epsilon16$, respectively, corresponding to tensile axial strains resulting from the axial extension at the respective second regions 330b.

As a result of the strain signals $\epsilon9$, $\epsilon10$, $\epsilon11$, $\epsilon12$ corresponding to compressive axial strains and the strain signals $\epsilon13$, $\epsilon14$, $\epsilon15$, $\epsilon16$ corresponding to tensile axial strains, the strain signals $\epsilon9$ to $\epsilon16$ may be combined in various sums and differences to cancel out common thermal strains resulting from steady state temperature variations. In this way, the axial torque Tz can be resolved based on the strain signals $\epsilon9$ to $\epsilon16$ independent of steady state temperature variations.

In some embodiments, the axial torque Tz can be resolved based on the equation $Tz=\tau(\epsilon D-\epsilon C)$, where $\epsilon C$ is the sum of the strain signals provided by the third group of strain sensors 400c; $\epsilon D$ is the sum of the strain signals provided by the fourth group of strain sensors 400d; and is a function of the number of respective strain signals provided and the geometry and material characteristics of the body 301.

Due to the relatively complicated geometry of the body 301 resulting from the slits 320, $\tau$ can be determined experimentally through a calibration process, or through computer simulation using finite element analysis. For example, $\tau$ can be determined by analyzing the relationship between a known axial torque Tz acting on the body 301 and the axial strains experienced by the body 301 at the respective first and second regions 330a, 330b in response to being subjected to the known axial torque Tz.

In the illustrated example embodiment, EC can equal ($\epsilon9+\epsilon10+\epsilon11+\epsilon12$) and ED can equal ($\epsilon13+\epsilon14+\epsilon15+\epsilon16$). Accordingly, the axial torque can be resolved based on the equation $Tz=\tau(\epsilon13+\epsilon14+\epsilon15+\epsilon16-\epsilon9-\epsilon10-\epsilon11-\epsilon12)$.

By adding an equal thermal strain to each of the strain signals $\epsilon9$ to $\epsilon16$, it can be seen that common thermal strains resulting from steady state temperature variations are cancelled out when resolving the axial torque Tz using the above equation. As a result of the orientation and position of the strain sensors 409 to 416, axial strains resulting from axial and lateral forces are also cancelled out when resolving the axial torque Tz using the above equation.

In other embodiments, additional or fewer strain signals may be used to resolve the axial torque $T_z$. For example, the axial torque Tz may be resolved using one strain signal from the third group of strain sensors 400c and one strain signal from the fourth group of strain sensors 400d. For example, the axial torque Tz may be resolved based on the equation $Tz=\tau(\epsilon D-\epsilon C)$, where ($\epsilon D-\epsilon C$) is equal to one of ($\epsilon13-\epsilon9$), ($\epsilon13-\epsilon11$), ($\epsilon14-\epsilon10$), ($\epsilon14-\epsilon12$), ($\epsilon15-\epsilon11$), etc. Such simplification may remove the ability to distinguish between axial strains resulting from the axial torque Tz and those resulting from lateral forces, but may nonetheless be useful in applications in which predominantly axial torque acts on the tip 30.

Referring back to FIG. 1D, during use of the system 10, the strain signals $\epsilon1$ to $\epsilon16$ may be provided to the console 12. In some embodiments, the system 10 may be calibrated prior to use. The calibration may involve applying known axial and lateral forces and axial torques to the tip 30 of the instrument 14. Based on the corresponding strain signals ϵ1 to ϵ16 received from the strain sensors 401 to 416 during calibration, scaling or amplification factors may be determined for one or more of the strain signals ϵ1 to ϵ16, and correction factors and offsets can be determined and applied to the previously-noted equations (Fz=α(ϵB−ϵA), $$Fy = \frac{\gamma}{2}(\epsilon 5 - \epsilon 7), Fx = \frac{\chi}{2}(\epsilon 6 - \epsilon 8),$$

and Tz=τ(ϵD−ϵC)). The equations and associated protocols for determining Fz, Fy, Fx, and Tz, as well as the corresponding calibration data may be stored in the memory 16 of the computing device 13, or an external database communicatively linked to the computing device 13.

Once calibrated, the console 12 may operate to receive the strain signals ϵ1 to ϵ16 during use of the instrument 14. The processing unit 18 may process the strain signals ϵ1 to ϵ16 according to the equations, protocols, and calibration data stored in the memory 16 to determine some or all of the forces Fx, Fy, Fz and the torque Tz.

The determined forces Fx, Fy, Fz and torque Tz may then be transmitted to a user of the system 10. In some embodiments, the determined forces Fx, Fy, Fz and torque Tz may be provided to the user as part of a graphical user interface displayed on the display 19. In some embodiments, haptic signals that correspond to at least one of the determined forces Fx, Fy, Fz and torque Tz may be transmitted to the operator of the instrument. In some embodiments, these haptic signals may be used to impart vibrations, forces, and/or motions to the user's hands. In some embodiments, these haptic signals may be amplified in intensity compared to the determined forces Fx, Fy, Fz and torque Tz.

It will be appreciated that in some embodiments, the computing device 13 and its processing unit 18 may comprise digital components such as a laptop or desktop computer having a central processing unit and memory. In other embodiments, the computing device 13 and its processing unit 18 may comprise analog components. For example, the computing device 13 and the processing unit 18 may be a number of electronic components arranged in summing and difference configurations (such as summing amplifiers and differential amplifiers) for determining the forces Fx, Fy, Fz, and torque Tz based on the strain signals ϵ1 to ϵ16. The electronic components may be configured with amplification factors corresponding to the coefficients and calibration data for determining the forces Fx, Fy, Fz and torque Tz based on the above noted equations. In other embodiments, the computing device 13 and the processing unit 18 may comprise electronic circuitry such as, but not limited to, application specific integrated circuits or Field Programmable Gate arrays.

Referring now to FIGS. 9 to 11D, another example sensor assembly 500 for use with the system 10 is shown. Apart from using FBG type strain sensors 601 to 616 in place of the resistance type strain sensors 401 to 416, respectively, the assembly 500 is generally similar to the assembly 100 described above. Accordingly, similar components are designated with the same reference numerals, and such components will not be described in detail for brevity.

An FBG strain sensor comprises a longitudinal periodic variation of the index of refraction in a short length of the core of an optical fiber. When the optical fiber is in an unstrained state, the FBG strain sensor reflects a central wavelength of light corresponding to the index of refraction and the spacing of the periodic variation. The remaining wavelengths of light pass through the FBG strain sensor. The central wavelength of the reflected light is referred to as a Bragg wavelength.

Compression and/or extension of the optical fiber can alter the periodic variation of the index of refraction of the FBG strain sensor, resulting in a shift in the Bragg wavelength. The shift in the Bragg wavelength is proportional to the strain experienced by the FBG strain sensor. Thus, the strain at the location of the FBG strain sensor can be determined by measuring the shift in the Bragg wavelength of the FBG strain sensor.

A single optical fiber can include multiple FBG strain sensors. Each FBG strain sensor can correspond to a distinct initial Bragg wavelength when in an unstrained state and operate along a distinct wavelength spectrum. The Bragg wavelength of each FBG strain sensor can be identified using, for example, wavelength division multiplexing. Thus, the strain at the location of each FBG strain sensor can be determined by measuring the shift in the respective Bragg wavelengths of each FBG strain sensor.

Figure 9:
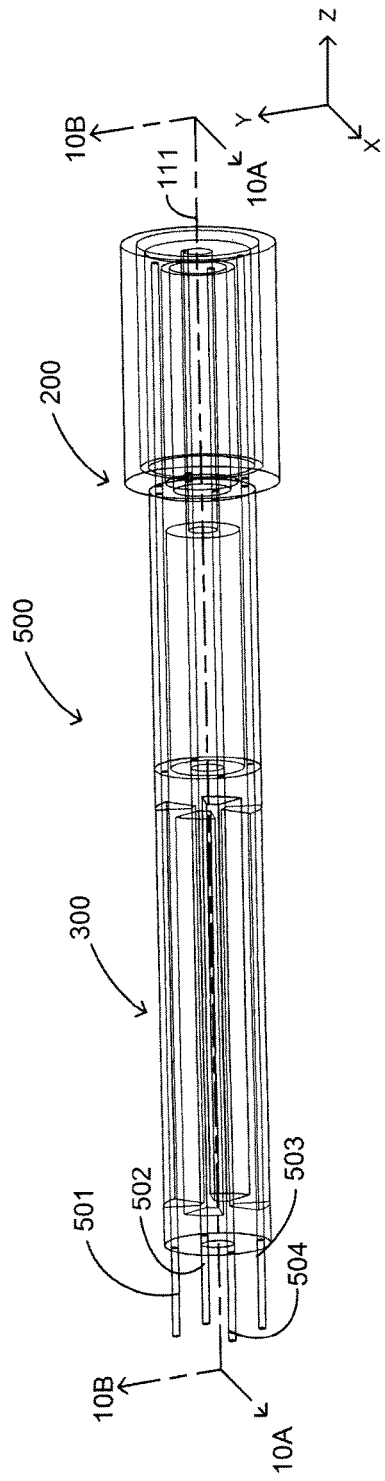
FIG. 9 is a perspective view of another example embodiment of a sensor assembly.
Figure 10A:
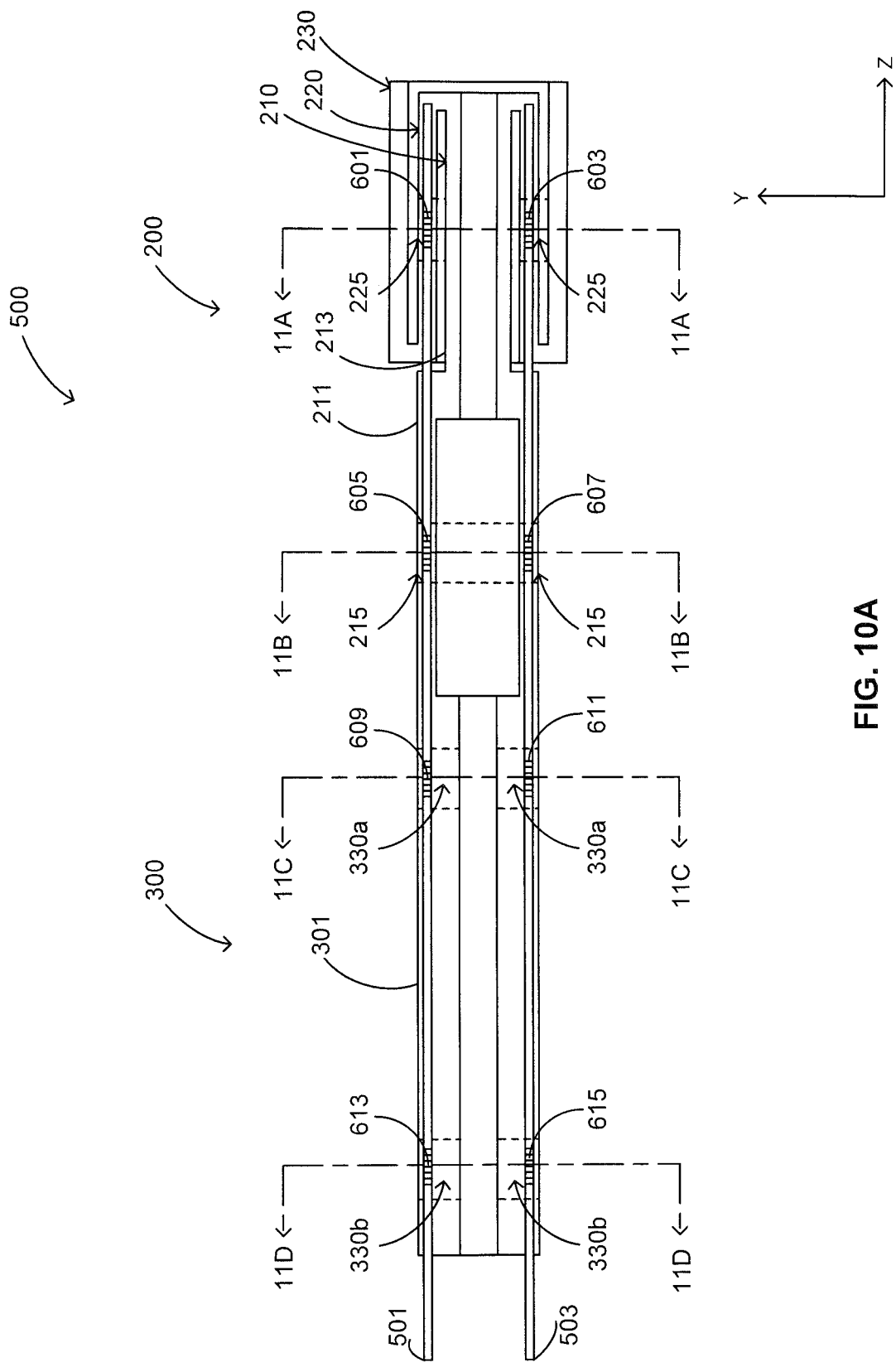
FIG. 10A is a cross section taken along line 10A-10A in FIG. 9.
Figure 10B:
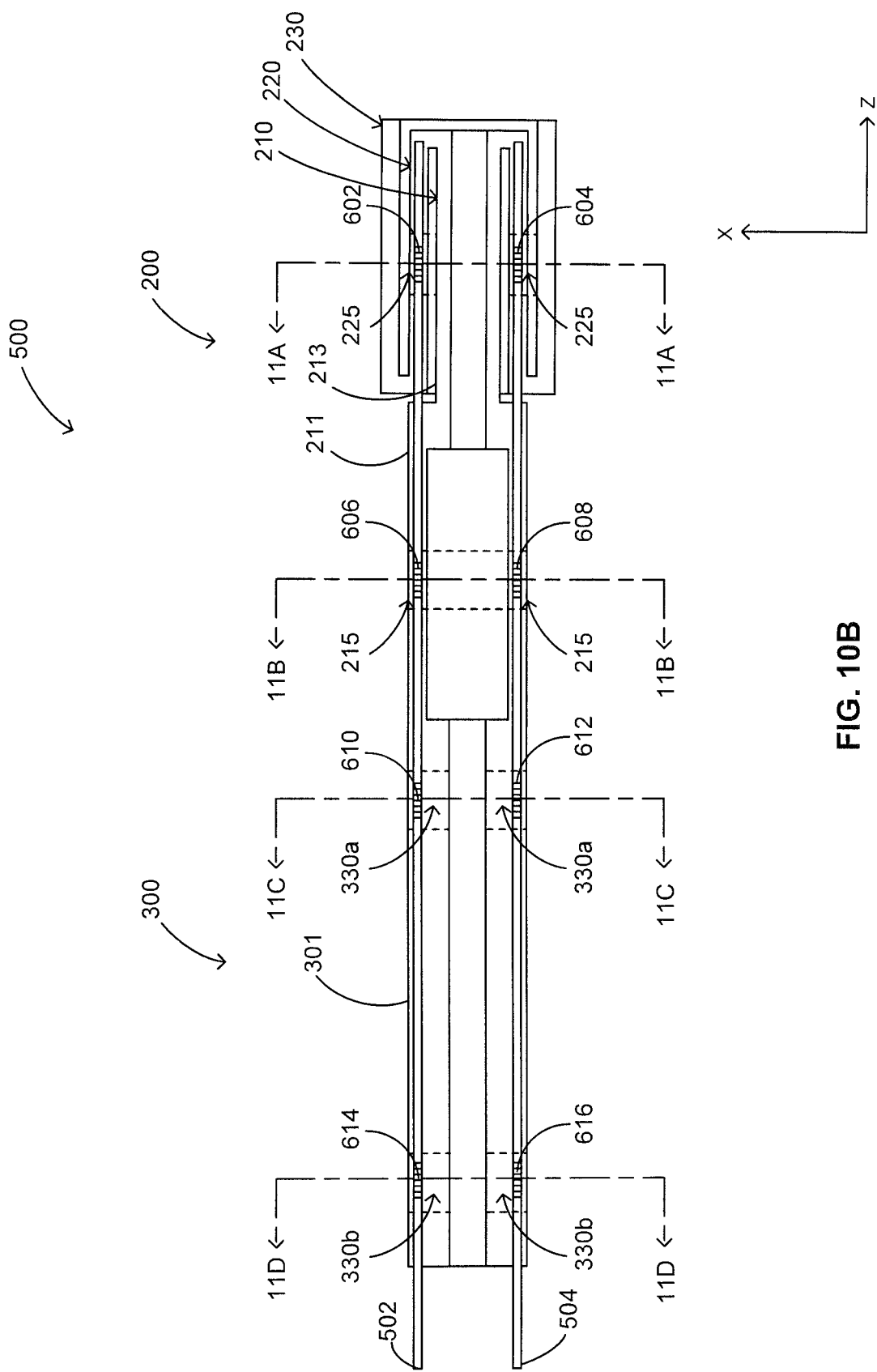
FIG. 10B is a cross section taken along line 10B-10B in FIG. 9.
Figure 11A:
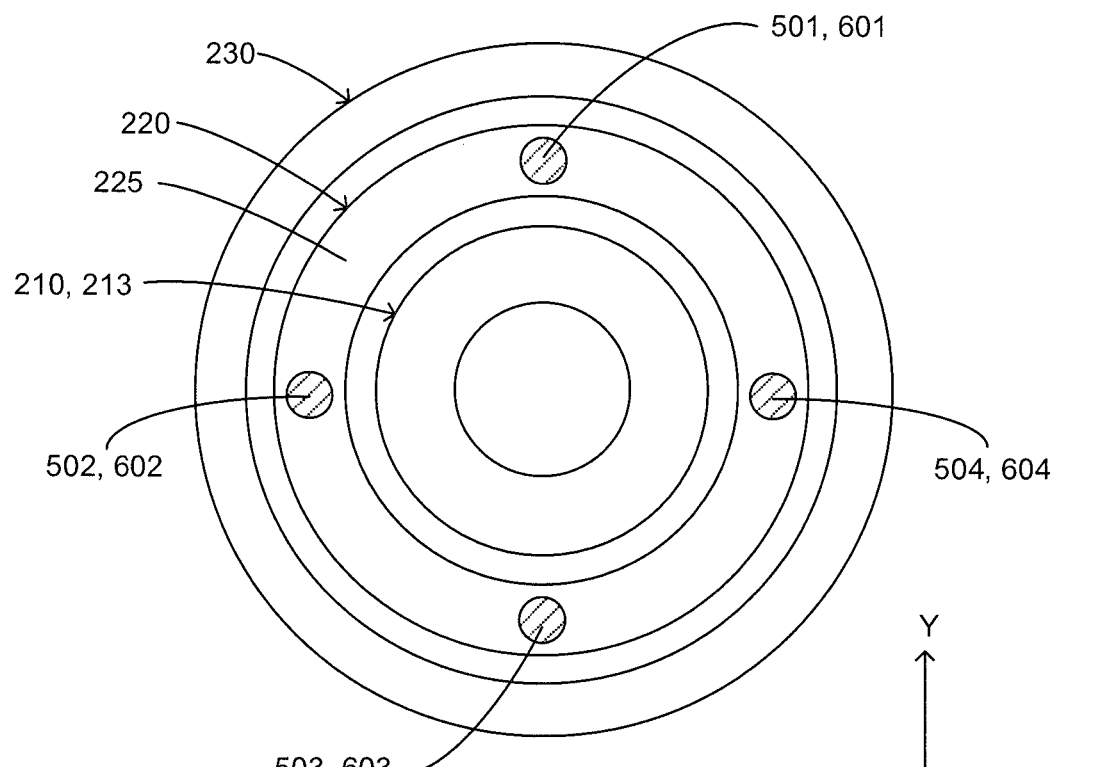
FIG. 11A is a cross section taken along line 11A-11A in FIGS. 10A and 10B.
Figure 11B:
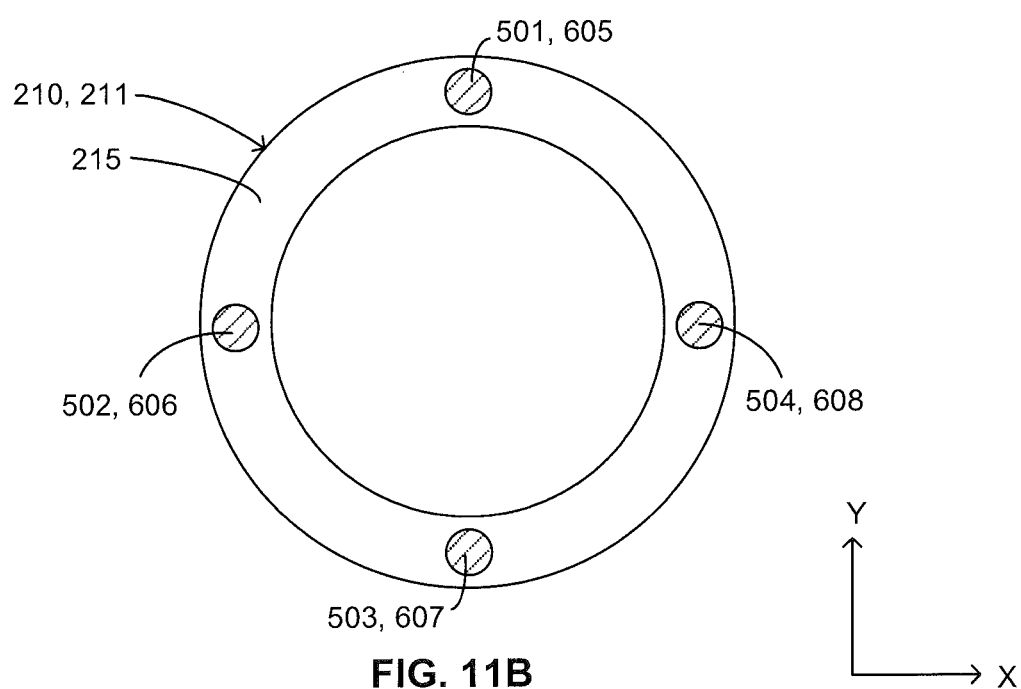
FIG. 11B is a cross section taken along line 11B-11B in FIGS. 10A and 10B.
Figure 11C:
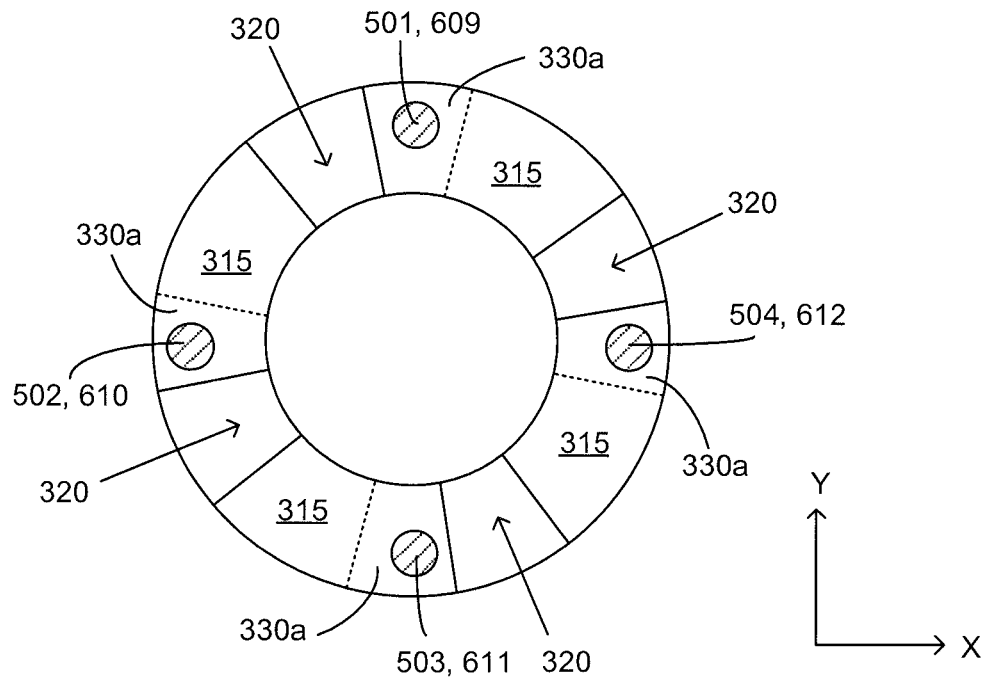
FIG. 11C is a cross section taken along line 11C-11C in FIGS. 10A and 10B.
Figure 11D:
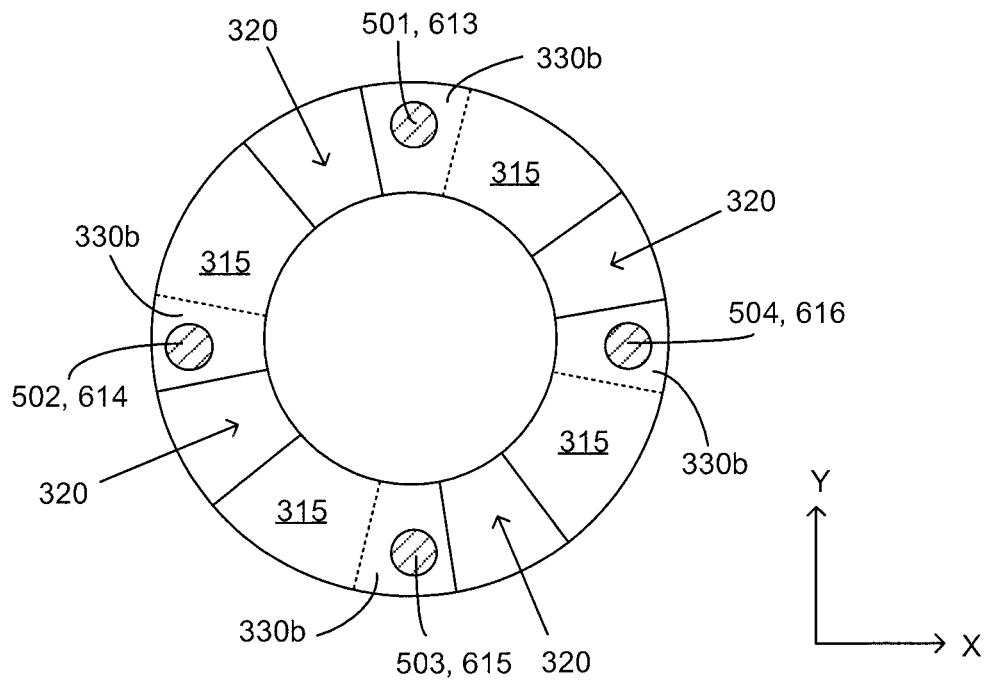
FIG. 11D is a cross section taken along line 11D-11D in FIGS. 10A and 10B.

As shown in FIGS. 9, 10A, and 10B the sensor assembly 500 includes four optical fibers 501, 502, 503, and 504 extending through the front portion 200 and the rear portion 300 of the sensor body 110. Each optical fiber 501 to 504 is spaced equidistantly about and oriented parallel to the axis 111 of the sensor body 110.

Referring now to FIGS. 10A to 11D, in the illustrated example embodiment, each optical fiber includes four FBG strain sensors formed in spaced apart sections along the length of the optical fiber. Specifically, in the illustrated example embodiment, the optical fiber 501 includes FBG strain sensors 601, 605, 609, 613; the optical fiber 502 includes FBG strain sensors 602, 606, 610, 614; the optical fiber 503 includes FBG strain sensors 603, 607, 611, 615; and the optical fiber 504 includes FBG strain sensors 604, 608, 612, 616. The FBG strain sensors on a single optical fiber can each correspond to a distinct Bragg wavelength and operate in a distinct wavelength spectrum.

The FBG strain sensors 601 to 616 are embedded in the body 110 at the same respective regions 215, 225, 330a, and 330b as described with respect to the strain sensors 401 to 416, respectively. For instance, the FBG strain sensors 601 to 604 are embedded and configured to sense axial strains of the second member 220 at the second region 225; the FBG strain sensors 605 to 609 are embedded and configured to sense axial strains of the proximal section 211 of the first member 210 at the first region 215; the FBG strain sensors 609 to 613 are embedded and configured to sense axial strains at the respective first regions 330a in the central side wall 315 of the body 301; and the FBG strain sensors 613 to 616 are embedded and configured to sense axial strains at respective second regions 330b in the central side wall 315 of the body 301.

Figure 12:
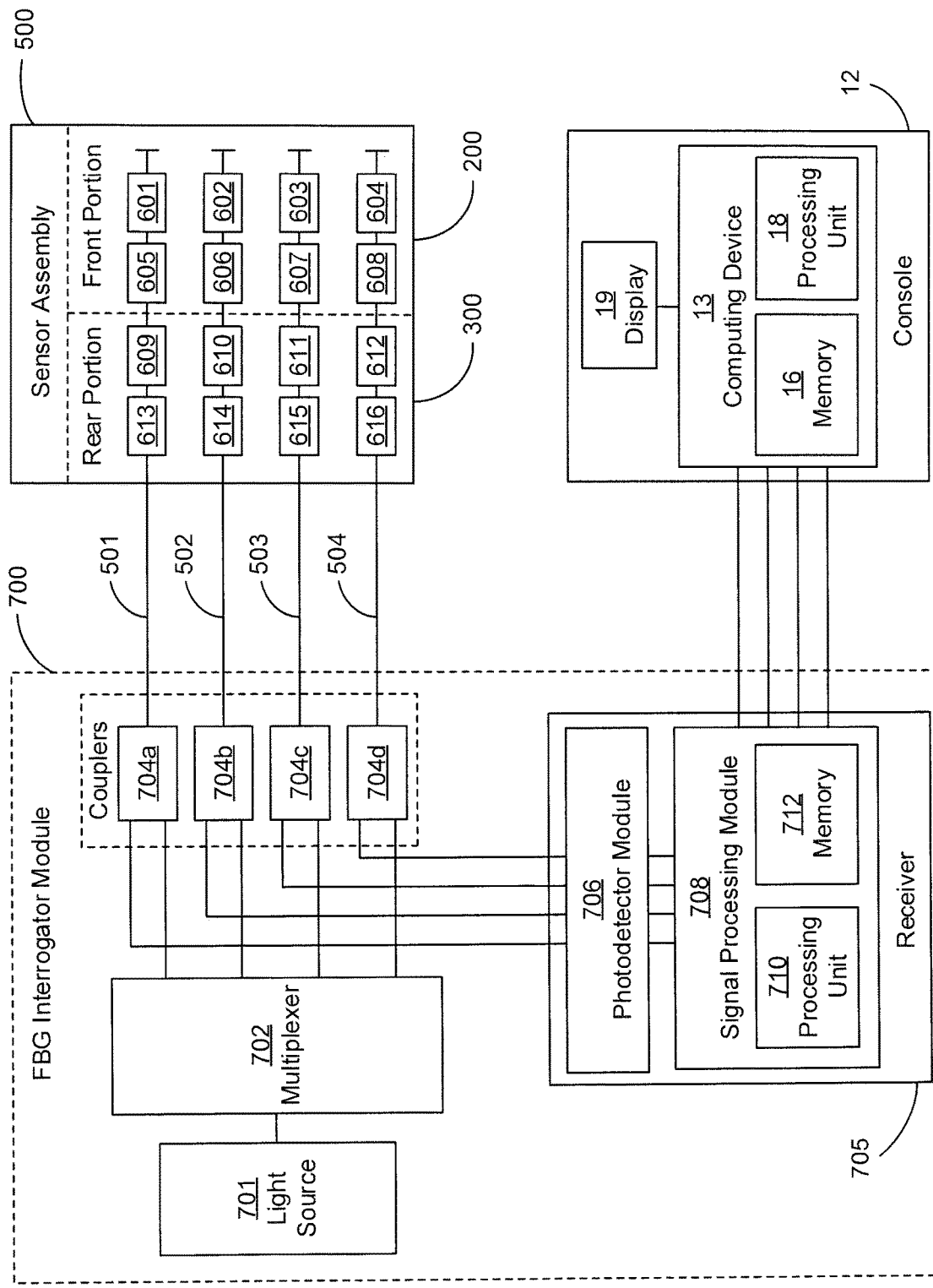
FIG. 12 is a block diagram of an example embodiment of a fiber Bragg grating interrogator module.

Referring now to FIG. 12, a simplified block diagram of an example embodiment of an FBG interrogator module 700 is shown. In embodiments in which the sensor assembly 500 is used, the interrogator module 700 may be used to interrogate the FBG strain sensors 601 to 616, to determine the respective strain signals ϵ1 to ϵ16 corresponding to axial strains at the respective regions 215, 225, 330a, 330b.

In the illustrated example embodiment, the interrogator module 700 is provided as a component that is communicatively linked to the console 12. In other embodiments, some or all of the components of the interrogator module 700 may be provided as part of the console 12.

In the illustrated example embodiment, the interrogator module 700 includes a light source 701 and a receiver 705, each coupled to the optical fibers 501 to 504. A multiplexer 702 can be coupled between the light source 701 and the optical fibers 501 to 504. Light emitted from the light source 701 can be routed through the multiplexer 702 to each of the optical fibers 501 to 504 to interrogate the FBG strain sensors 601 to 616. Light reflected by each of the FBG strain sensors 601 to 616 may be returned from the optical fibers 501 to 504 and routed through respective couplers 704a to 704d to the receiver 705.

The receiver 705 can comprise a photodetector module 706 and a signal processing module 708. The photodetector module 706 can operate to convert the reflected light into wavelength signals indicating the Bragg wavelength of each of the FBG strain sensors 601 to 616. The photodetector module 706 can provide the wavelength signals to the signal processing module 708.

The signal processing module 708 can comprise one or more processing units 710 and memory 712. The processing unit 710 can operate to process the wavelength signals provided by the photodetector module 706 to determine the present Bragg wavelength of each of the FBG strain sensors 601 to 616. The processing unit 710 can then utilize processing logic to calculate the shift in the respective Bragg wavelengths of the FBG strain sensor 601 to 616.

The shift can be calculated based on a comparison of the present Bragg wavelength to the initial Bragg wavelength measured when the strain sensors 601 to 616 are in an unstrained state. Data indicating the initial Bragg wavelength can be stored in the memory 712. Based on processing logic and the shift in the respective Bragg wavelengths of the FBG strain sensors 601 to 616, the signal processor 708 can generate the respective strain signals $\epsilon 1$ to $\epsilon 16$.

The signal processing module 708 can transmit the strain signals $\epsilon 1$ to $\epsilon 16$ to the console 12 for processing. The computing device 13 can process the strain signals $\epsilon 1$ to $\epsilon 16$ to determine the axial and lateral forces and axial torques acting at the tip 30. The computing device 13 can process the strain signals $\epsilon 1$ to $\epsilon 16$ in a similar manner as outlined above with respect to the strain sensors 401 to 416. In some embodiments, one or more of the determined forces Fx, Fy, Fz and torque Tz may be provided to the user as part of a graphical user interface displayed on the display 19. In other embodiments, haptic signals that correspond to at least one of the determined forces Fx, Fy, Fz and torque Tz may be transmitted to the operator of the instrument. In some embodiments, these haptic signals may be vibrational. In some embodiments, these haptic signals may be amplified in intensity compared to the calculated forces Fx, Fy, Fz and torque Tz.

In the illustrated example embodiments described above, the sensor assemblies 100, 500 are shown affixed to a catheter ablation instrument 14 having an electrode tip 30. As noted above, however, the sensor assemblies 100, 500 may be used with other types of MIS surgical instruments.

For example, referring to FIG. 13, the sensor assembly 500 is shown affixed to an MIS sawing instrument 814. The instrument 814 can include a shaft 820 and a tip 830 having a circular saw 838. In other examples, the sensor assembly 100 may be used with the MIS instrument 814. The sensor assemblies 100, 500 may be affixed to the shaft 820 and the tip 830 of the instrument 814 in the same manner as described above with respect to the shaft 20 and the tip 30 of the catheter ablation instrument 14.

Referring to FIG. 14, the sensor assembly 500 is shown affixed to an MIS cutting instrument 914. The MIS instrument 914 can include a shaft 920 and a tip 930 having scissors 938. In other examples, the sensor assembly 100 may be used with the MIS instrument 914. The sensor assemblies 100, 500 may be affixed to the shaft 920 and the tip 930 of the instrument 914 in the same manner as described above with respect to the shaft 20 and the tip 30 of the catheter ablation instrument 14.

In other example embodiments, the sensor assemblies 100, 500 may be affixed to an MIS instrument in a different manner. For example, referring to FIG. 15, the sensor assembly 500 is shown as an add-on sensor for a catheter ablation instrument 1014. In the illustrated example embodiment, the sensor assembly 500 can be temporarily affixed to the instrument 1014 such that the sensor assembly 500 can be detached from the instrument 1014 when not in use. In other examples, the sensor assembly 100 may be used with the instrument 1014.

In the illustrated example embodiment, the shaft 1020 of the instrument 1014 extends into the proximal end 302 of the sensor body 110 and through the lumen 116 of the sensor body 110, and the tip 1030 extends out of the distal end 204 of the sensor body 110. A number of micro screws 1040 may extend through the sensor body 110 to hold the shaft 1020 in place within the lumen 116. The micro screws 1040 may partially screw into the shaft 1020, or may press against the shaft 1020 to hold the shaft 1020 securely in place within the lumen 116. The tip 1030 of the instrument 1014 may be secured to the sensor body 110 through a set of micro clamps 1050. The micro clamps 1050 may extend from the distal end 234 of the third member 230 of the sensor body 110 and inwardly toward the lumen 116. The micro clamps may firmly press against the distal end 1024 of the shaft 1020 or the proximal end 1032 of the tip 1030 to hold the tip 1030 in place, such that any forces or torques acting on the tip 1030 are transferred through the sensor body 110. It will be understood that the number of micro screws 1040 and micro clamps 1050 may vary depending on, for example, the dimensions and application of the sensor assembly 500.

Figure 16:
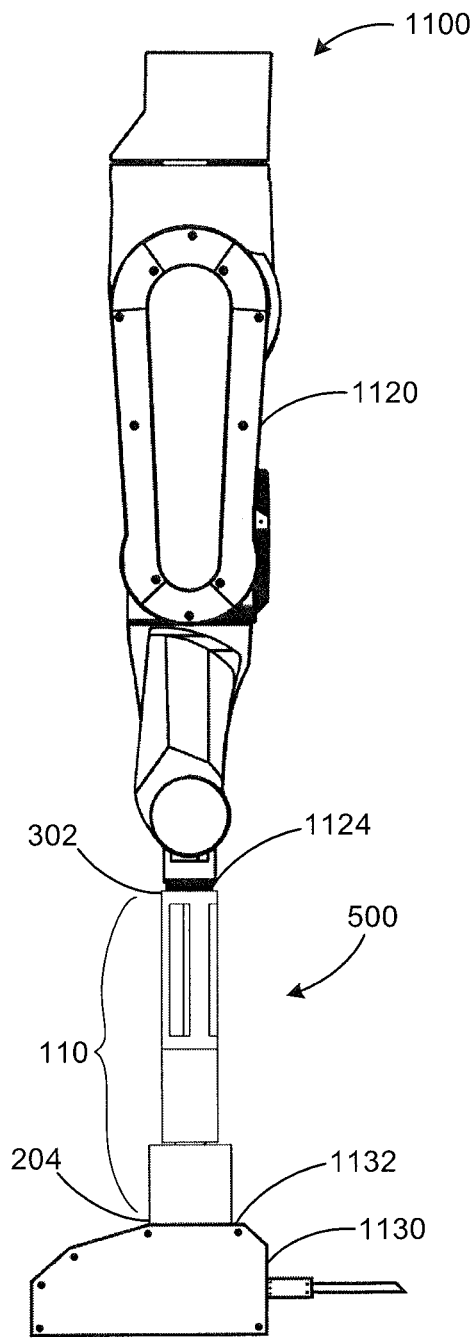
FIG. 16 is a side view of the sensor assembly of FIG. 9 attached to a robotic arm.

As noted above, the sensor assemblies 100, 500 may also be used in applications other than MIS. For example, referring to FIG. 16, the sensor assembly 500 is shown affixed to a robotic arm 1100 having a body 1120 and an end effector 1130. In other examples, the sensor assembly 100 may be affixed to the robotic arm 1100.

In the illustrated example embodiment, a distal end 1124 of the robotic arm body 1120 is affixed to the proximal end 302 of the sensor body 110, and a proximal end 1132 of the end effector 1130 is affixed to the distal end 204 of the sensor body 110. The body 1120 and the end effector 1130 of the robotic arm 1100 can be affixed to the sensor body 110 using, for example, screws, springs, clamps, swelling materials, adhesives, or through any other suitable means that allows for forces and torques acting on the end effector 1130 to be transferred through the sensor body 110.

Electrical leads (not shown) may extend from the body 1120 of the arm 1100 to the end effector 1130 through the lumen 116 of the sensor body 110. The electrical leads may be used to transmit various control signals for controlling the end effector 1130. Other components may also extend through the lumen 116 depending on the type of end effector 1130 being used and the particular application for which the robotic arm 1100 and the sensor assembly 500 (or 100) are being used.

Referring now to FIGS. 17A to 19D, a large scale prototype of the sensor assembly 100 was constructed to measure and investigate relative strains resulting from forces and torques acting on the prototype sensor assembly. The prototype sensor assembly was constructed to include the resistance type strain sensors 401, 403, 405, 407, 409, 411, 413, and 415 positioned as shown in and described with respect to FIGS. 2 to 8. Weights were used to apply various forces and torques to the prototype sensor assembly. The forces and torques applied to the prototype sensor assembly included axial forces Fz, lateral forces Fy, and axial torques Tz as shown in FIGS. 5A, 5B, and 8, respectively.

FIGS. 17A to 19D illustrate graphs showing experimental strain data as a function of the various forces and torques applied to the prototype sensor assembly. Each experiment was repeated seven times. The mean value for each resulting strain is shown with the respective standard deviation.

Figure 17A:
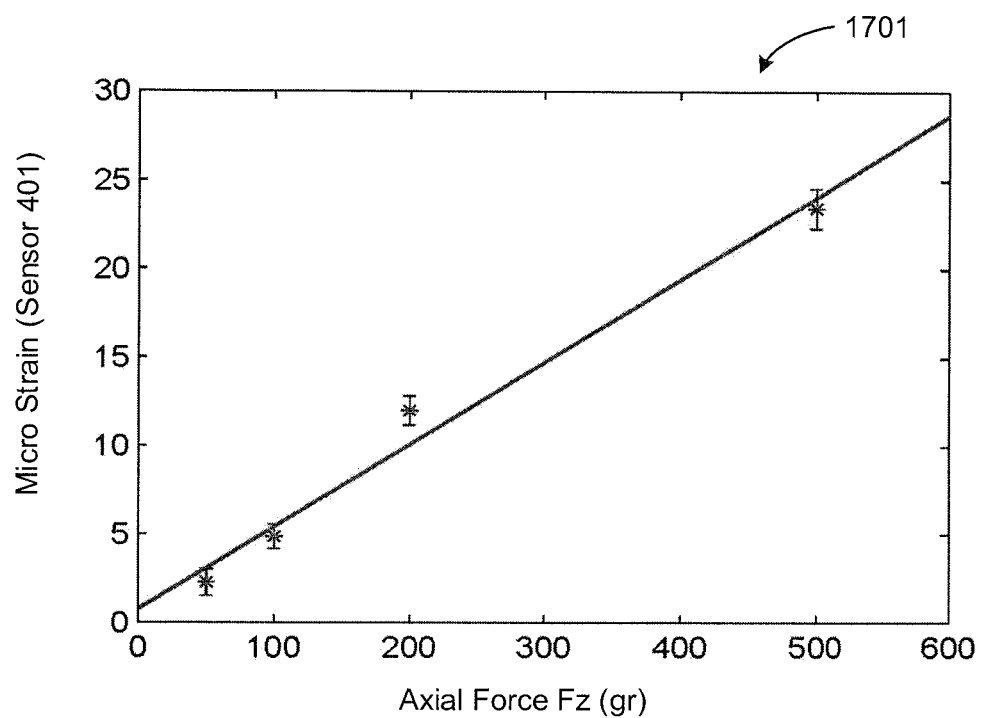
FIGS. 17A and 17B illustrate graphs showing experimental strain data as a function of axial forces acting on a prototype sensor assembly.
Figure 17B:
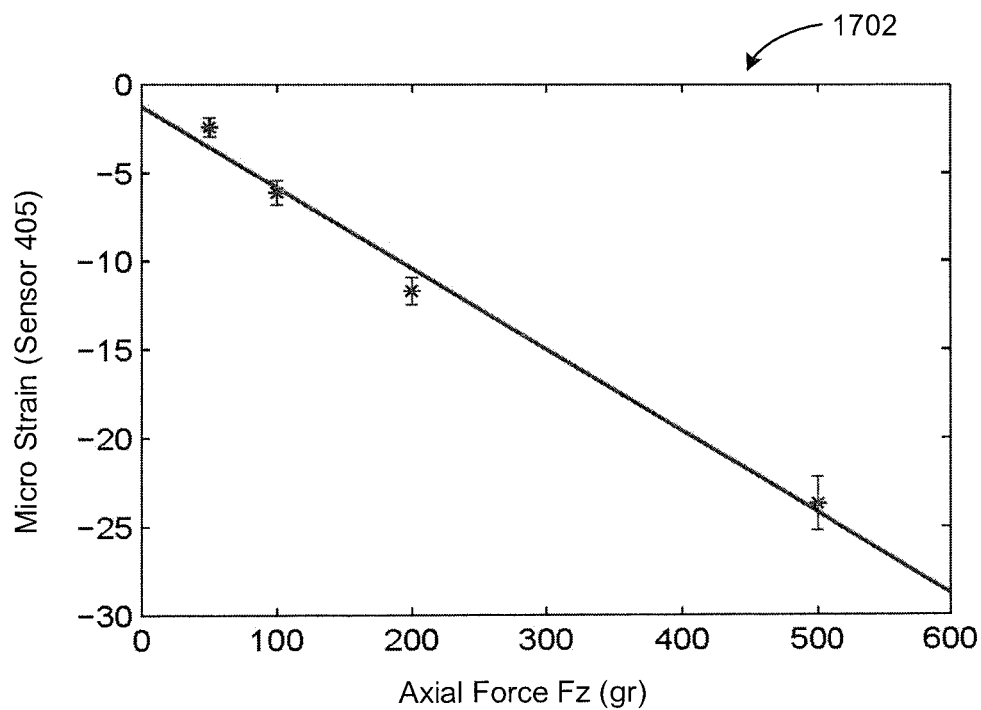

FIGS. 17A and 17B illustrate graphs showing experimental strain data as a function of the various axial forces Fz applied to the prototype sensor assembly. The graph 1701 of FIG. 17A shows the strains experienced by strain sensor 401 as a function of the various axial forces Fz. The graph 1702 of FIG. 17B shows the strains experienced by the strain sensor 405 as a function of the various axial forces Fz.

As can be seen from the graphs 1701 and 1702, in response to the various axial forces Fz, the strain sensor 401 experienced tensile axial strain while the strain sensor 405 experienced compressive axial strain having an absolute value approximately equal to the tensile axial strain experienced by the strain sensor 401. By adding an equal thermal strain to each of the strains experienced by the strain sensors 401, 405, it can be seen that common thermal strains can be cancelled out by combining the two strains.

Figure 18A:
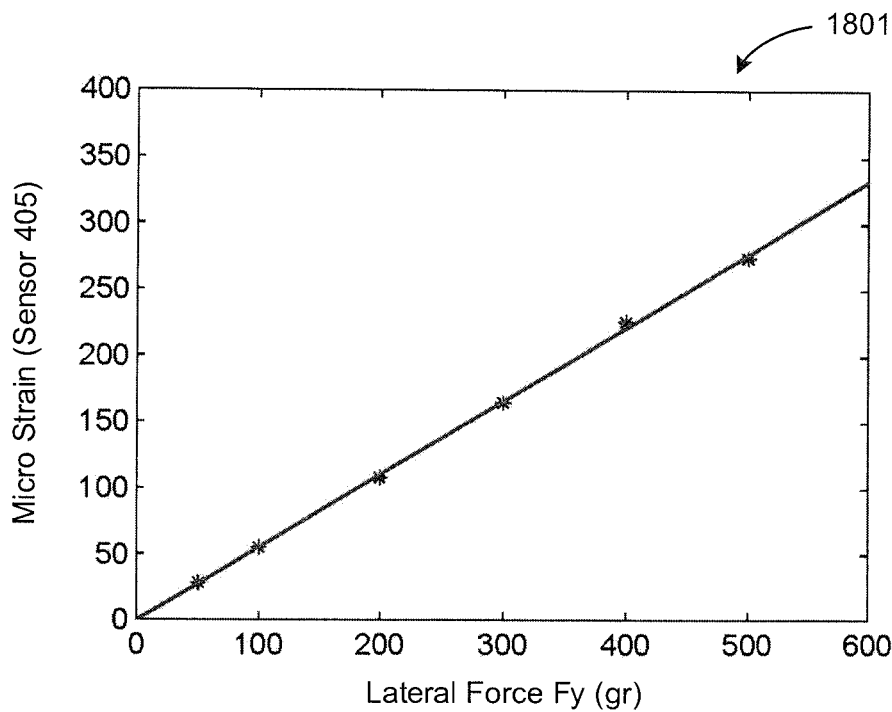
FIGS. 18A and 18B illustrate graphs showing experimental strain data as a function of lateral forces acting on the prototype sensor assembly.
Figure 18B:
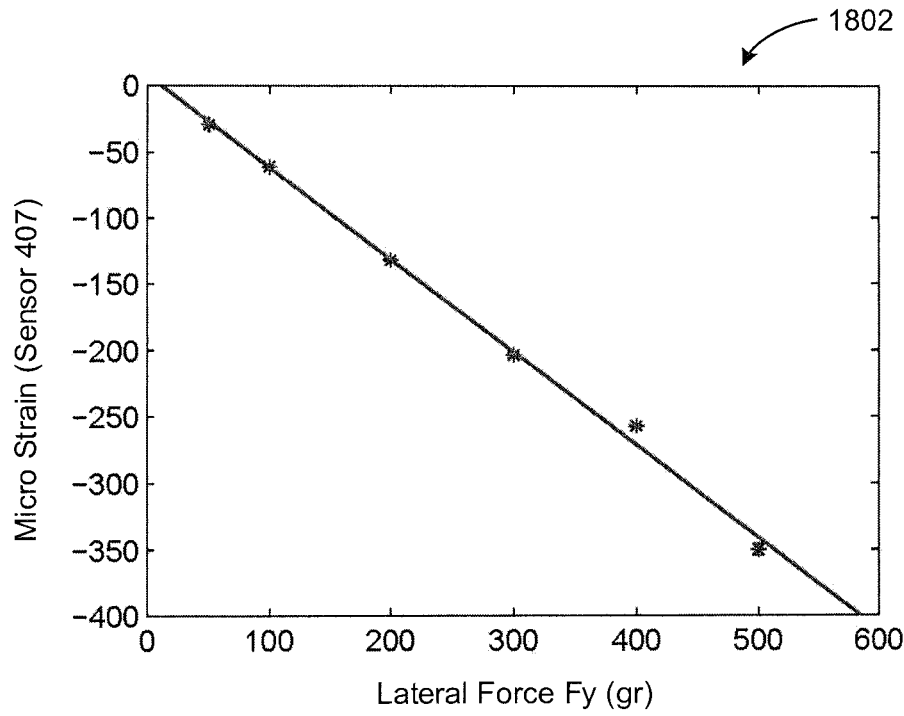

FIGS. 18A and 18B illustrate graphs showing experimental strain data as a function of the various lateral forces Fy applied to the prototype sensor assembly. The graph 1801 of FIG. 18A shows the strains experienced by strain sensor 405 as a function of the various lateral forces Fy. The graph 1802 of FIG. 18B shows the strains experienced by the strain sensor 407 as a function of the various lateral forces Fy.

As can be seen from the graphs 1801 and 1802, in response to the various lateral forces Fy, the strain sensor 405 experienced tensile axial strain while the strain sensor 407 experienced compressive axial strain having an absolute value approximately equal to the tensile axial strain experienced by the strain sensor 405. By adding an equal thermal strain to each of the strains experienced by the strain sensors 405, 407, it can be seen that common thermal strains can be cancelled out by combining the two strains.

Figure 19A:
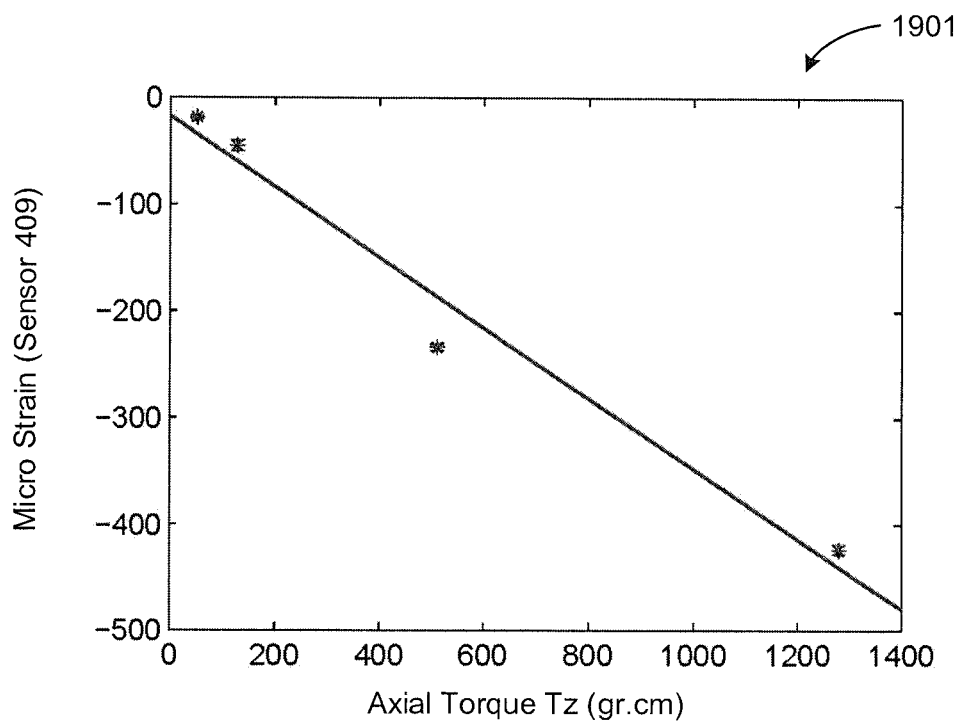
FIGS. 19A, 19B, 19C, and 19D illustrate graphs showing experimental strain data as a function of axial torques acting on the prototype sensor assembly.
Figure 19B:
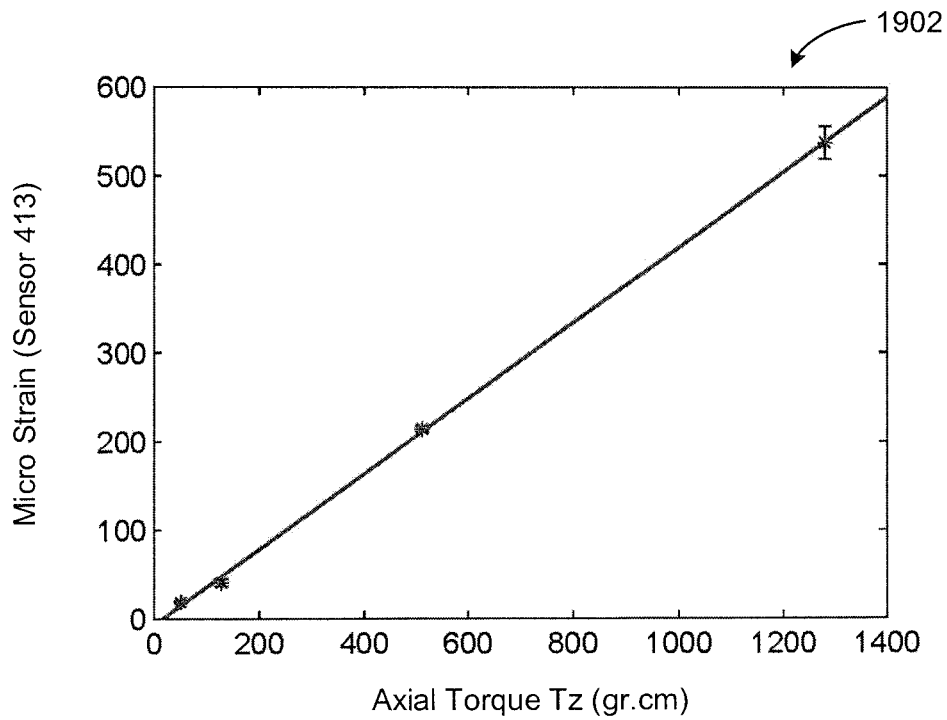
Figure 19C:
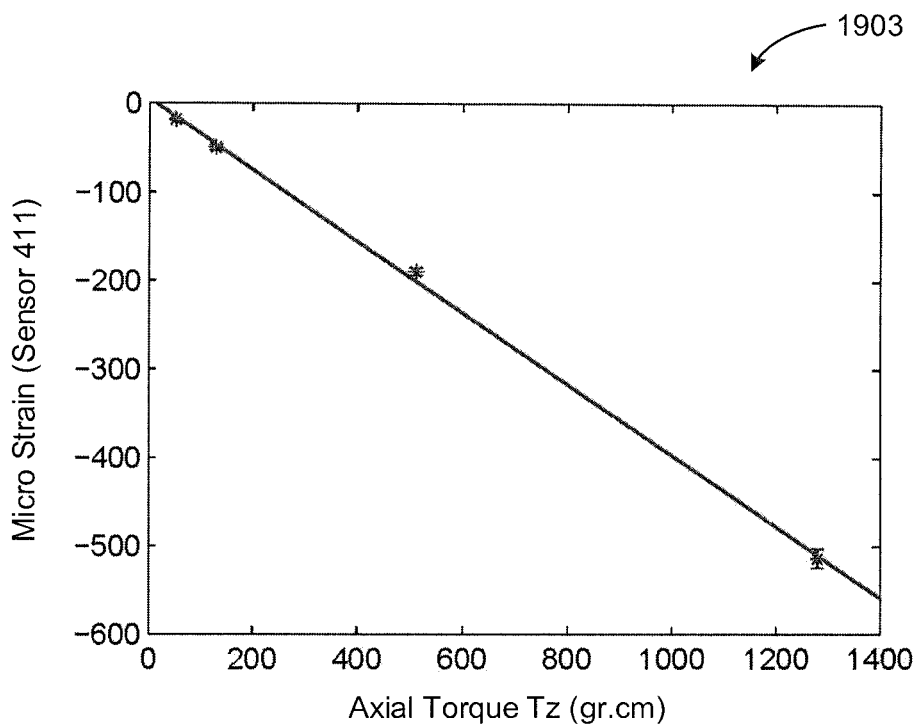
Figure 19D:
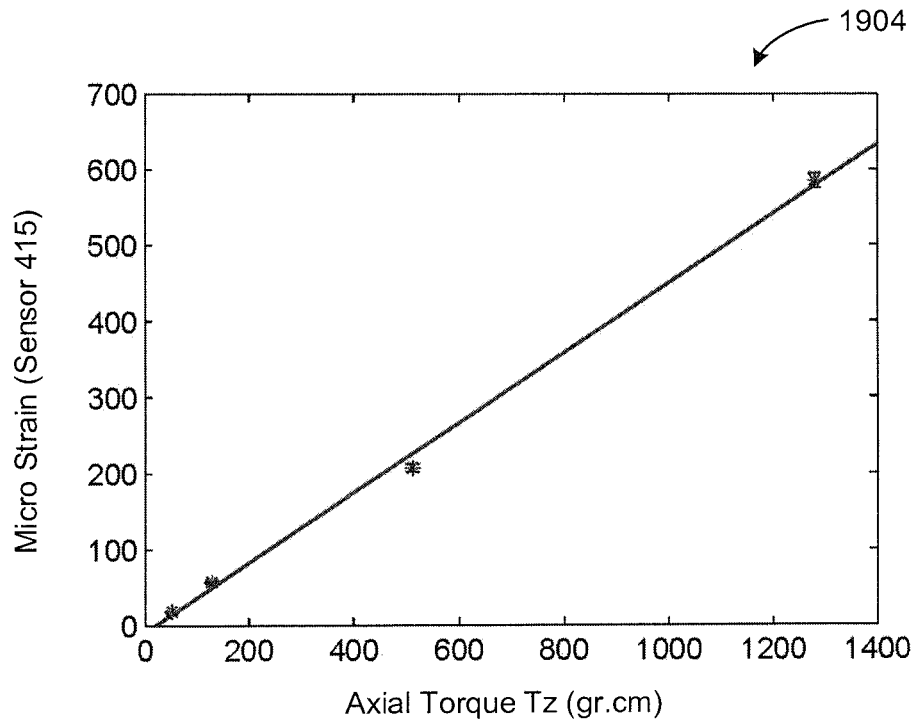

FIGS. 19A to 19D illustrate graphs showing experimental strain data as a function of the various axial torques Tz applied to the prototype sensor assembly. The graph 1901 of FIG. 19A shows the strains experienced by strain sensor 409 as a function of the various axial torques Tz. The graph 1902 of FIG. 19B shows the strains experienced by the strain sensor 413 as a function of the various axial torques Tz. The graph 1903 of FIG. 19C shows the strains experienced by the strain sensor 411 as a function of the various axial torques Tz. The graph 1904 of FIG. 19D shows the strains experienced by the strain sensor 415 as a function of the various axial torques Tz.

As can be seen from the graphs 1901 to 1904, in response to the various axial torques Tz, the strain sensors 409, 411 experienced compressive axial strain while the strain sensors 413, 415 experienced tensile axial strain having an absolute value approximately equal to the compressive axial strain experienced by the strain sensors 409, 411. By adding an equal thermal strain to each of the strains experienced by the strain sensors 409, 411, 413, 415, it can be seen that common thermal strains can be cancelled out by combining the four strains.

The experimental strain data illustrated in FIGS. 17A to 19D includes a reasonable amount of experimental error. The experimental error likely resulted from fabricating the prototype sensor assembly in multiple parts using a relatively low resolution 3D printer, and using adhesives to adhere the parts together. Another source of the experimental error may include defects in attaching the resistance type strain gauges to the body of the prototype sensor assembly. Integral and more precise construction of the sensor assembly may assist in reducing error.

Test Results: Micro-Scale Temperature Insensitive Force/Torque Sensor

Figure 20:
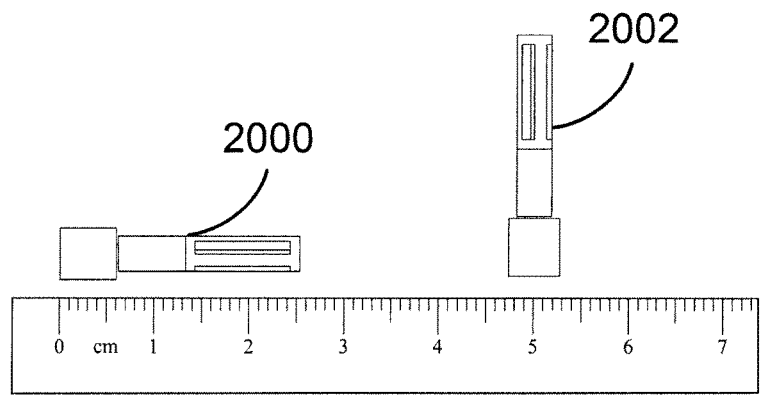
FIG. 20 is an image of example embodiments of micro-scale fabricated sensing structures in accordance with the teachings herein.

Referring now to FIG. 20, shown therein are example embodiments of a micro-scale fabricated sensing structures 2000 and 2002 in accordance with the teachings herein. This micro-scale sensing structures 2000 and 2002 have been fabricated for use in cardiac ablation surgery. Accordingly, dimensions of the sensing structure are optimized for cardiac ablation catheters and for the range of the force which is applied to the tip of cardiac catheters during ablation surgery. For example, the length of the sensing structures 2000 and 2002 may be about 25.4 mm, the outer diameter of the sensing structures 2000 and 2002 in the distal end of the front portion may be about 5.5 mm and the outer diameter of the sensing structures 2000 and 2002 in the proximal end of the rear portion may be about 3.5 mm. The applied force to the tip of cardiac ablation catheters during the ablation surgery is between 0.1N to 0.4N. However, the sensing structures 2000 and 2002 may have different dimensions and be able to measure different amounts of forces and torques for different applications.

Figure 21:
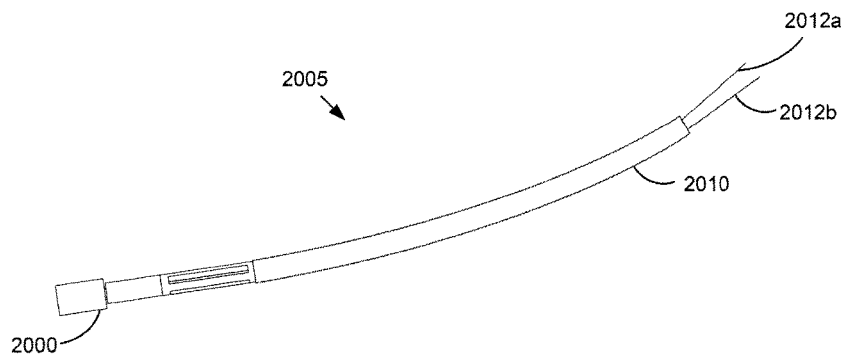
FIG. 21 is an image of an example embodiment of a micro-scale force/torque sensor with assembled optical fibers and attached sheath in accordance with the teachings herein.

Referring now to FIG. 21, shown therein is an example embodiment of a micro-scale force/torque sensor 2005 comprising the micro-scale sensing structure 2000, optical fibers 2012a and 2012b and an attached sheath 2010 in accordance with the teachings herein. Two optical fibers 2012a and 2012b were assembled onto the sensing structure 2000. Each optical fiber 2012a and 2012b includes 4 FBGs as sensing elements in order to measure the generated strains in the sensing structure due to any applied axial forces (Fz), lateral forces (Fy) and applied torques (Tz). Referring to FIG. 10A the optical fibers 2012a and 2012b correspond to optical fiber 501 with FBGs 601, 605, 609 and 613, and optical fiber 503 with FBGs 603, 607, 611 and 615, respectively. In order to support the sensing structure 2000 and also to cover the optical fibers 2012a and 2012b, a catheter sheath 2010 was attached to the proximal end (similar to element 302 in FIG. 1B) of the sensing structure 2000.

Figure 22:
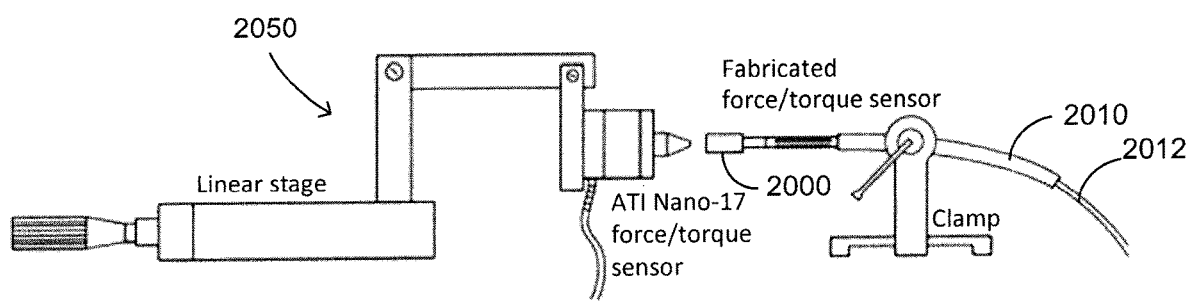
FIG. 22 is a side view of an experimental setup for applying axial force to the force/torque sensor of FIG. 21.
Figure 23:
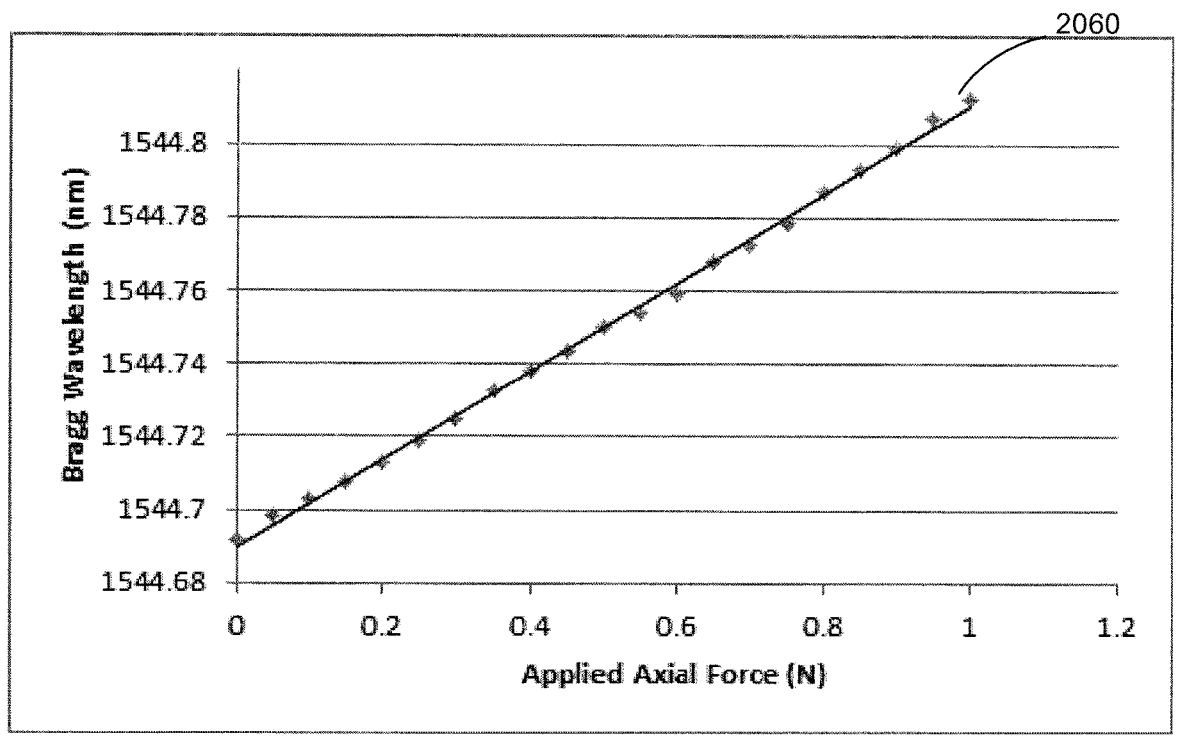
FIG. 23 is a plot showing experimental results of Bragg wavelength versus applied axial force for FBG 601 of the force/torque sensor of FIG. 21.
Figure 24:
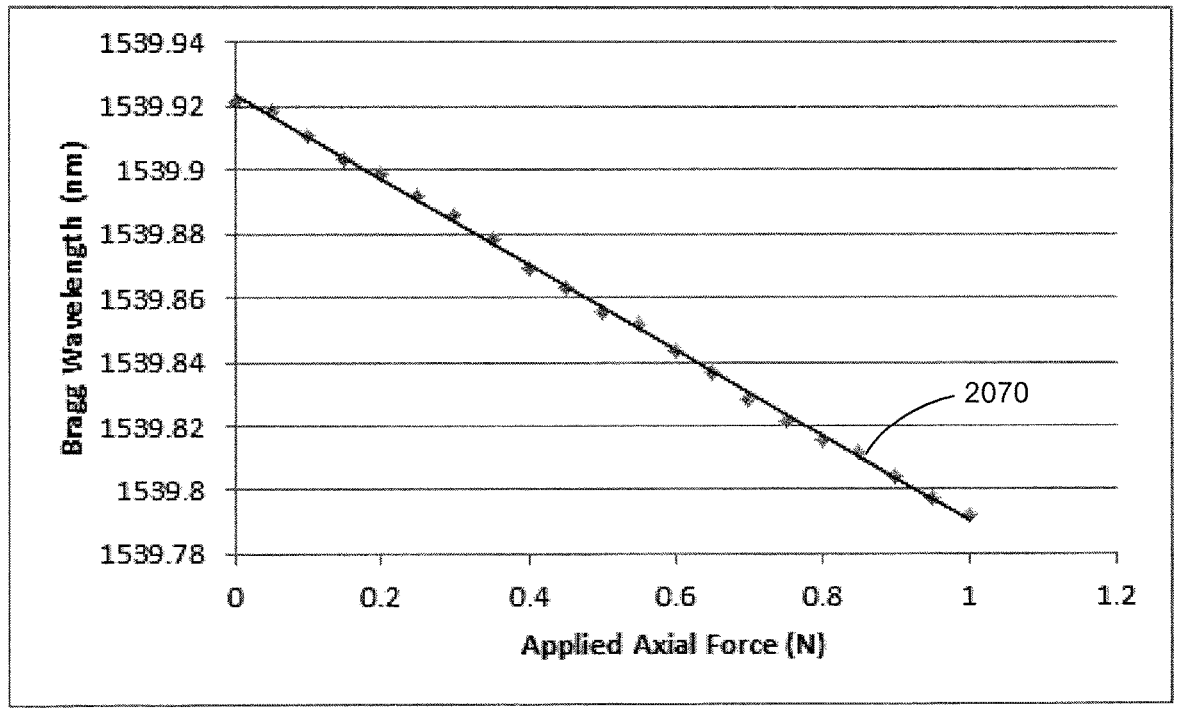
FIG. 24 is a plot showing experimental results of Bragg wavelength versus applied axial force for FBG 605 of the force/torque sensor of FIG. 21.
Figure 25:
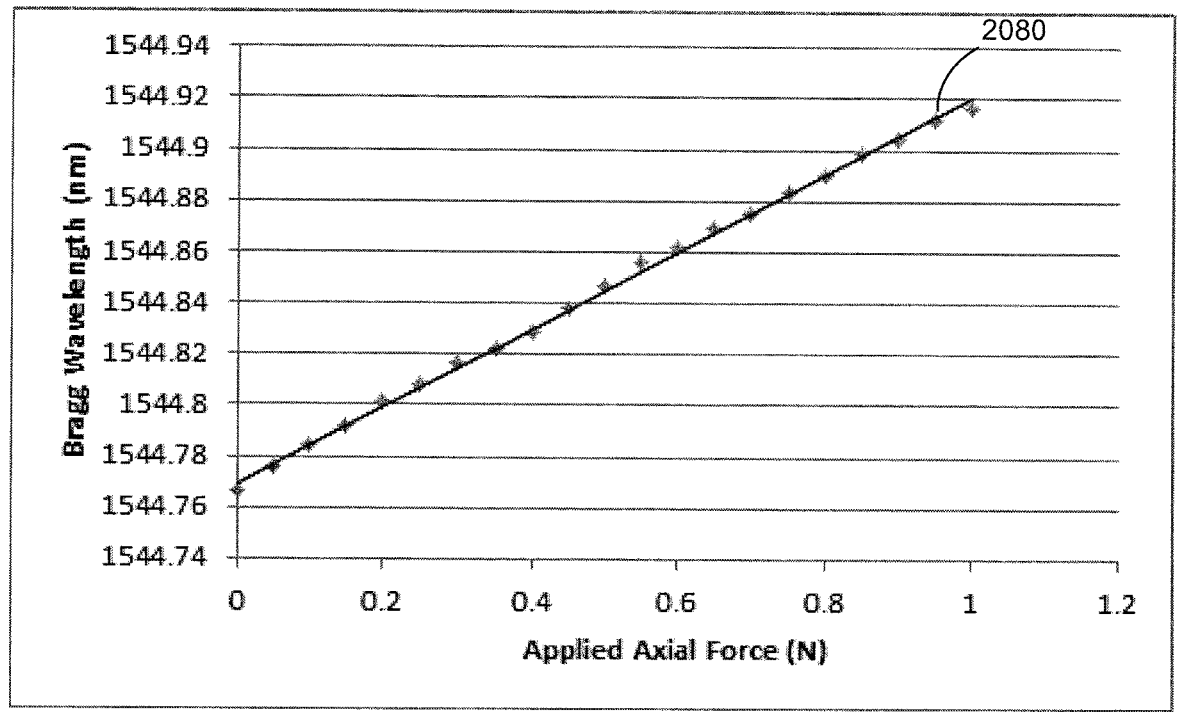
FIG. 25 is a plot showing experimental results of Bragg wavelength versus applied axial force for FBG 603 of the force/torque sensor of FIG. 21.
Figure 26:
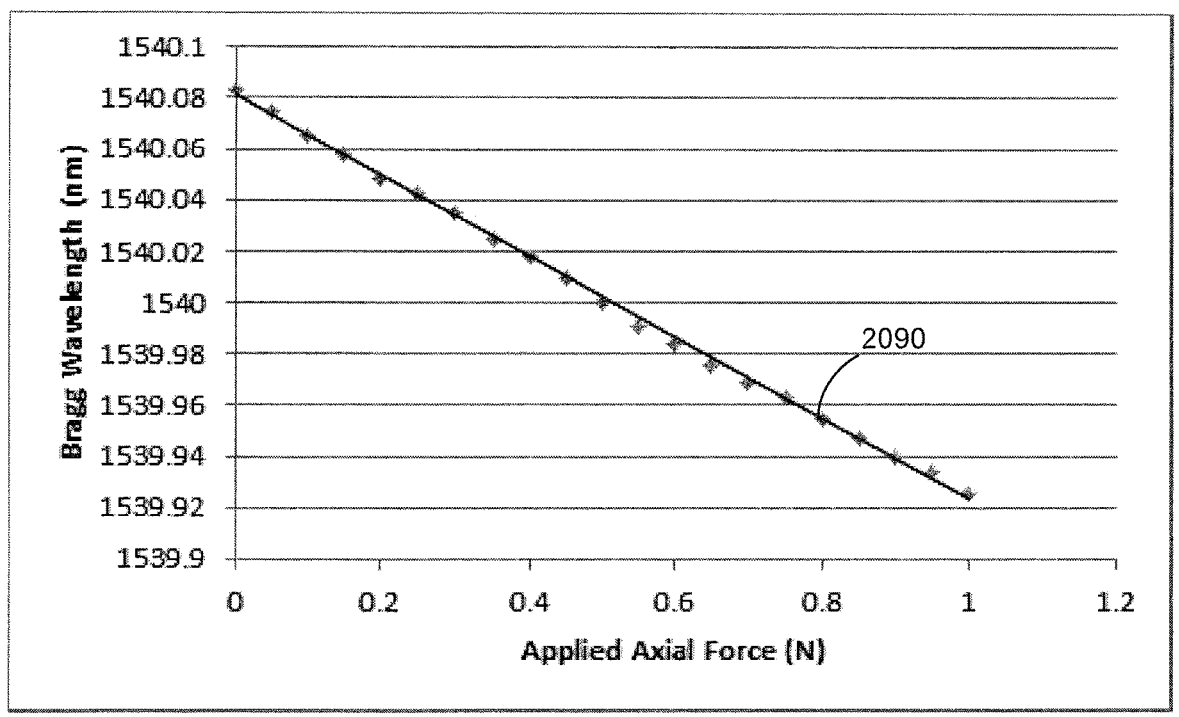
FIG. 26 is a plot showing experimental results of Bragg wavelength versus applied axial force for FBG 607 of the force/torque sensor of FIG. 21.

Referring now to FIG. 22, shown therein is a side view of an experimental setup 2050 for applying axial force to the force/torque sensor 2005. In order to apply axial forces to the tip of the sensor, the ATI Nano-17 standard force/torque sensor was attached to a linear stage. The fabricated sensor 2005 was held with a clamp and axial forces were applied by the ATI Nano-17 force/torque sensor to the fabricated sensor 2005. The axial force was applied to the fabricated sensor with steps of 0.05N.

For the experimental setup 2050, the Bragg wavelength shifts of the FBGs were measured with an Ibsen Photonics I-MON 512 E spectrometer. For all experiments, each measurement was repeated five times and the mean value was calculated as the final result. FIGS. 23-26 show the experimental results 2060, 2070, 2080 and 2090 for the Bragg wavelength shifts of FBG 601, FBG 605, FBG 603 and FBG 607, respectively. These results 2060, 2070, 2080 and 2090 show that FBG 601 and FBG 603 are extended due to the applied axial forces while the FBG 605 and FBG 607 are compressed.

Figure 27:
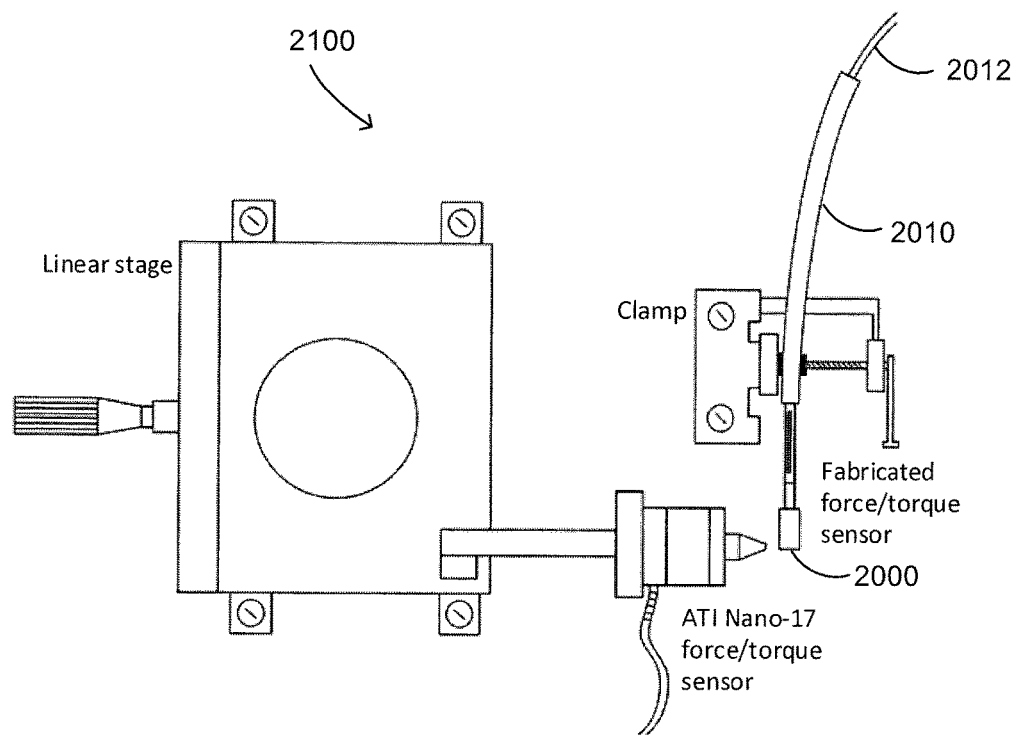
FIG. 27 is a top view of an experimental setup for applying lateral force to the force/torque sensor of FIG. 21.
Figure 28:
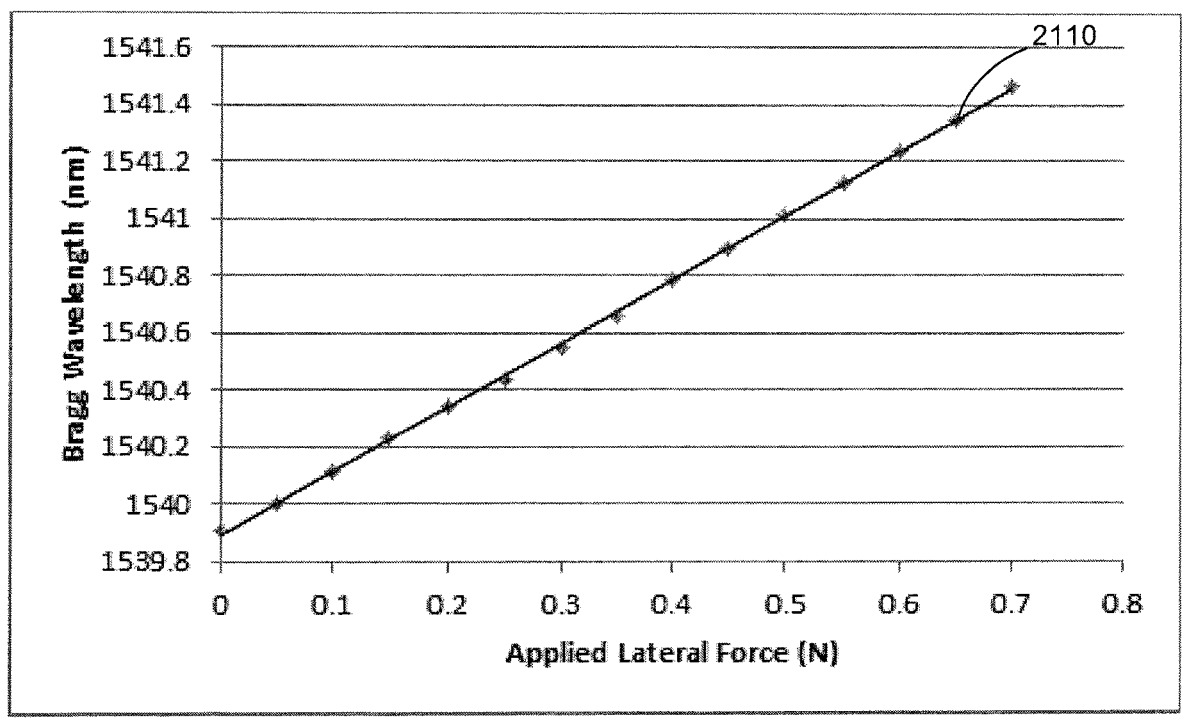
FIG. 28 is a plot showing experimental results of Bragg wavelength versus applied lateral force for FBG 605 of the force/torque sensor of FIG. 21.
Figure 29:
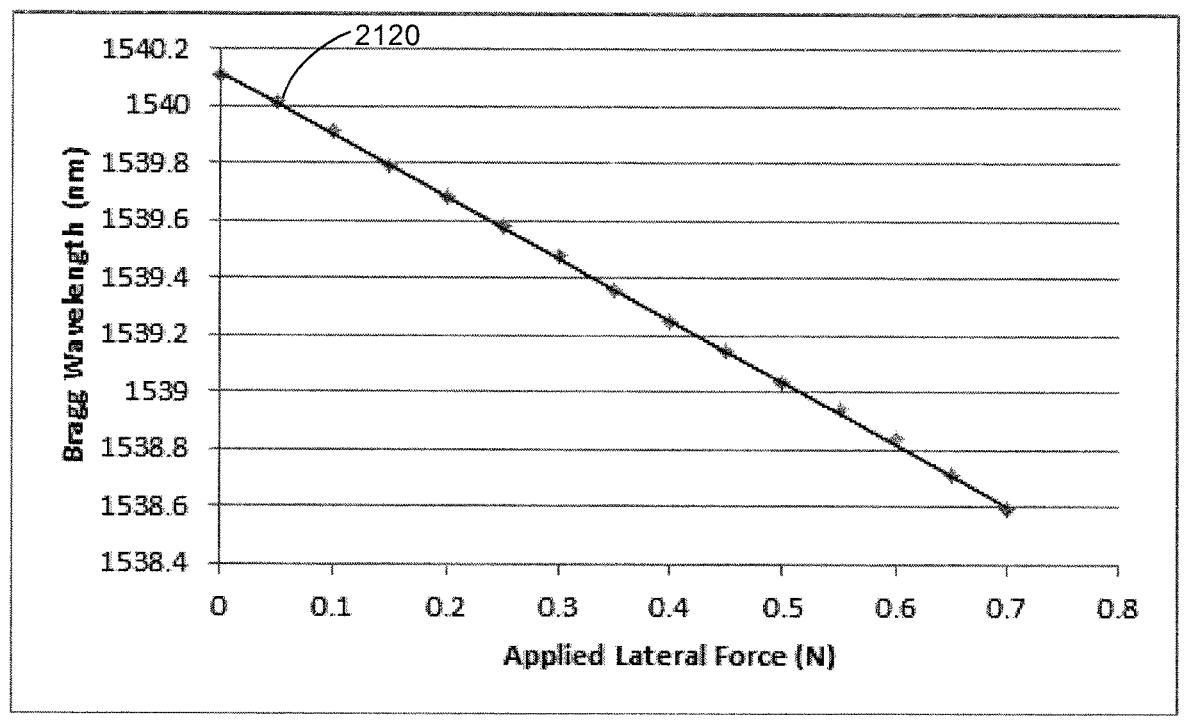
FIG. 29 is a plot showing experimental results of Bragg wavelength versus applied lateral force for FBG 607 of the force/torque sensor of FIG. 21.

Referring now to FIG. 27, shown therein is a top view of an experimental setup 2100 for applying lateral forces to the tip of the force/torque sensor 2005. The lateral forces were applied in steps of 0.05N during the experiment. FIGS. 28-29 show the Bragg wavelength shifts of FBG 605 and FBG 607, respectively. The applied lateral force was in the negative direction of the Y axis (i.e. the Y-axis is shown in FIG. 10A) similar to what is shown in FIG. 5B. These results 2110 and 2120 show that due to the applied lateral forces, the FBG 605 and FBG 607 are extended and compressed, respectively.

Figure 30:
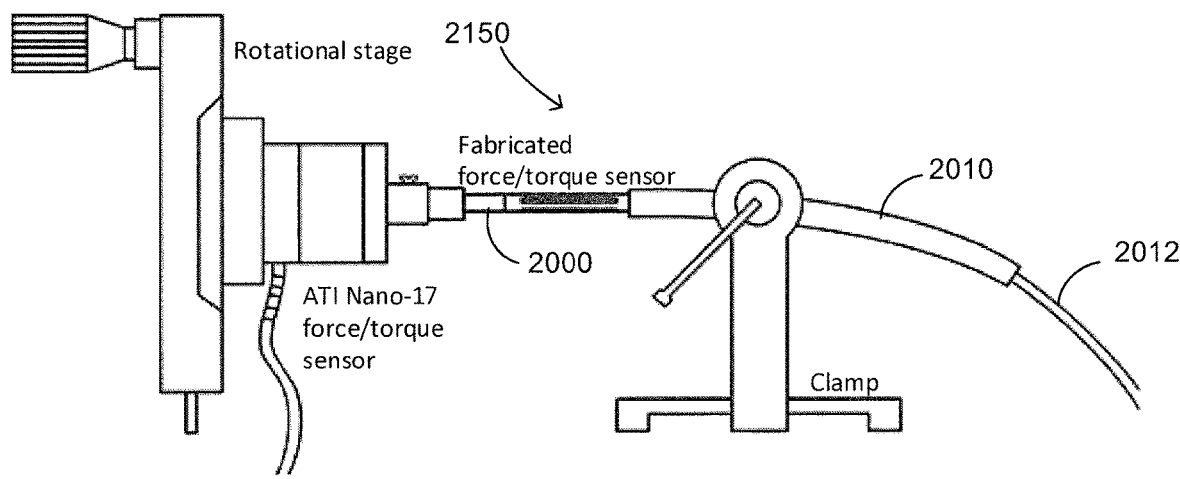
FIG. 30 is a side view of an experimental setup for applying axial torque to the force/torque sensor of FIG. 21.
Figure 31:
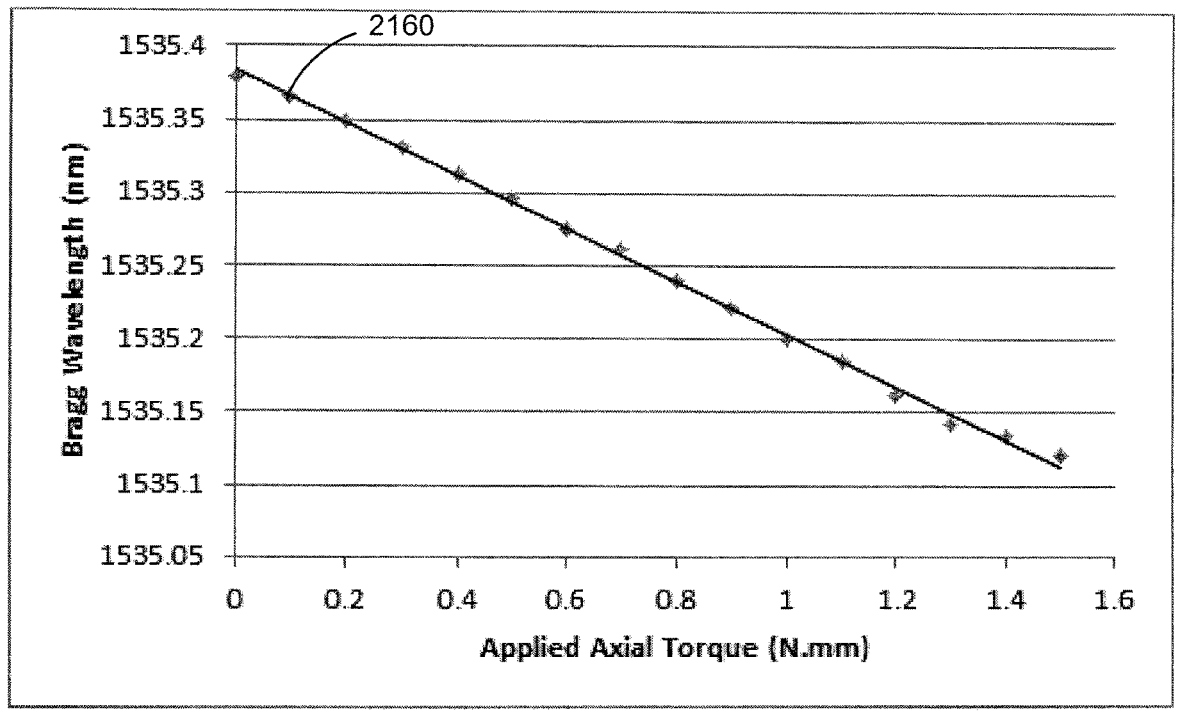
FIG. 31 is a plot showing experimental results of Bragg wavelength versus applied axial torque for FBG 609 of the force/torque sensor of FIG. 21.
Figure 32:
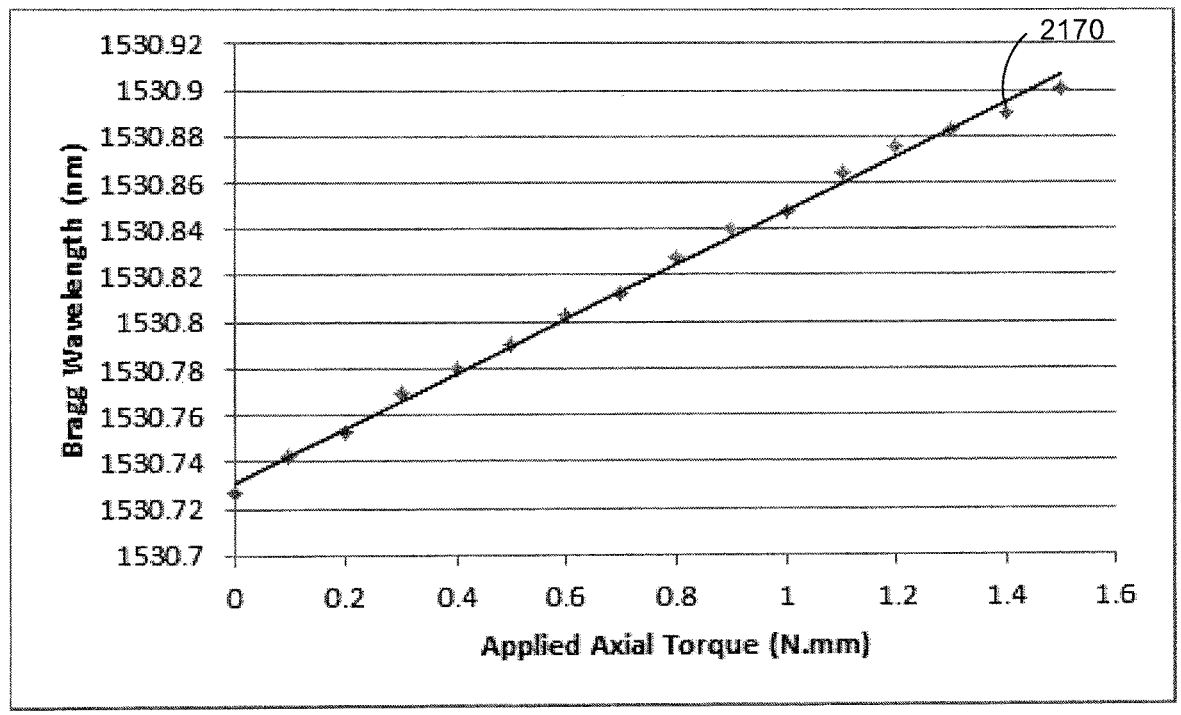
FIG. 32 is a plot showing experimental results of Bragg wavelength versus applied axial torque for FBG 613 of the force/torque sensor of FIG. 21.

Referring now to FIG. 30, shown therein is a side view of an experimental setup 2150 for applying axial torque to the force/torque sensor 2005. In order to apply the axial torque (i.e. twist) to the fabricated sensor 2005, the tip of the sensor 2005 was gripped with an ATI Nano-17 force/torque sensor. While the sheath 2010 of the fabricated sensor 2005 was held with a clamp, the ATI force/torque sensor was rotated along the Z axis with a rotational stage to generate axial torque in the fabricated sensor 2005. The torque was applied to the fabricated sensor 2005 with steps of 0.1N·mm. The experimental results for FBG 609 and FBG 613 are shown in FIGS. 31-32, respectively. The results 2160 and 2170 show that the FBG 609 is compressed due to the applied axial torque while the FBG 613 is extended.

Figure 33:
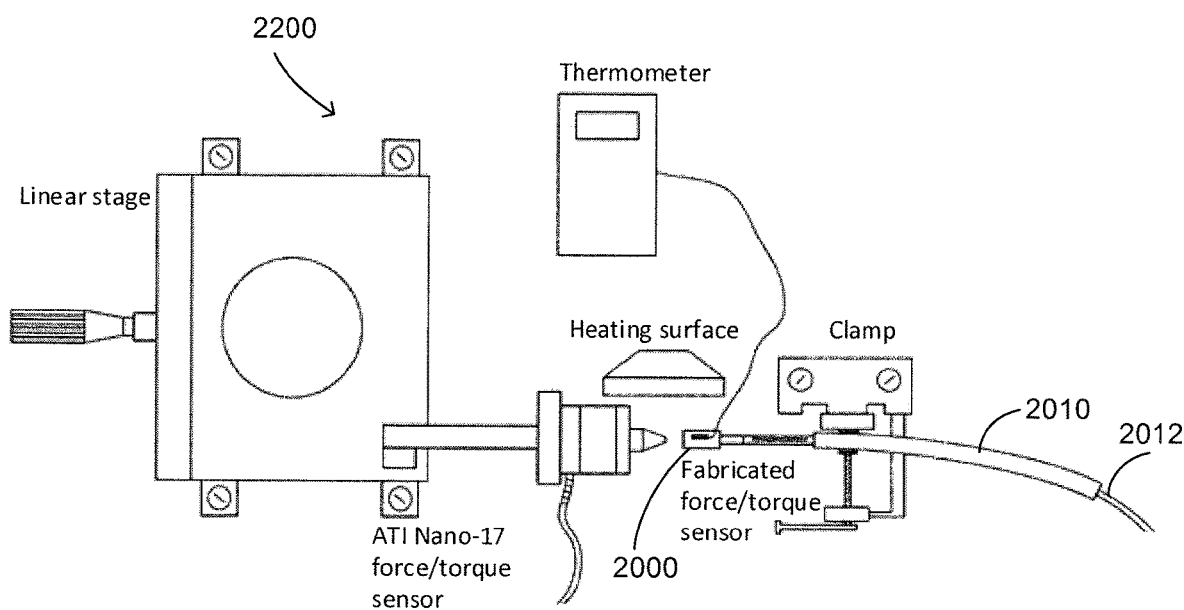
FIG. 33 is a top view of an experimental setup for changing the temperature around the force/torque sensor of FIG. 21.
Figure 34:
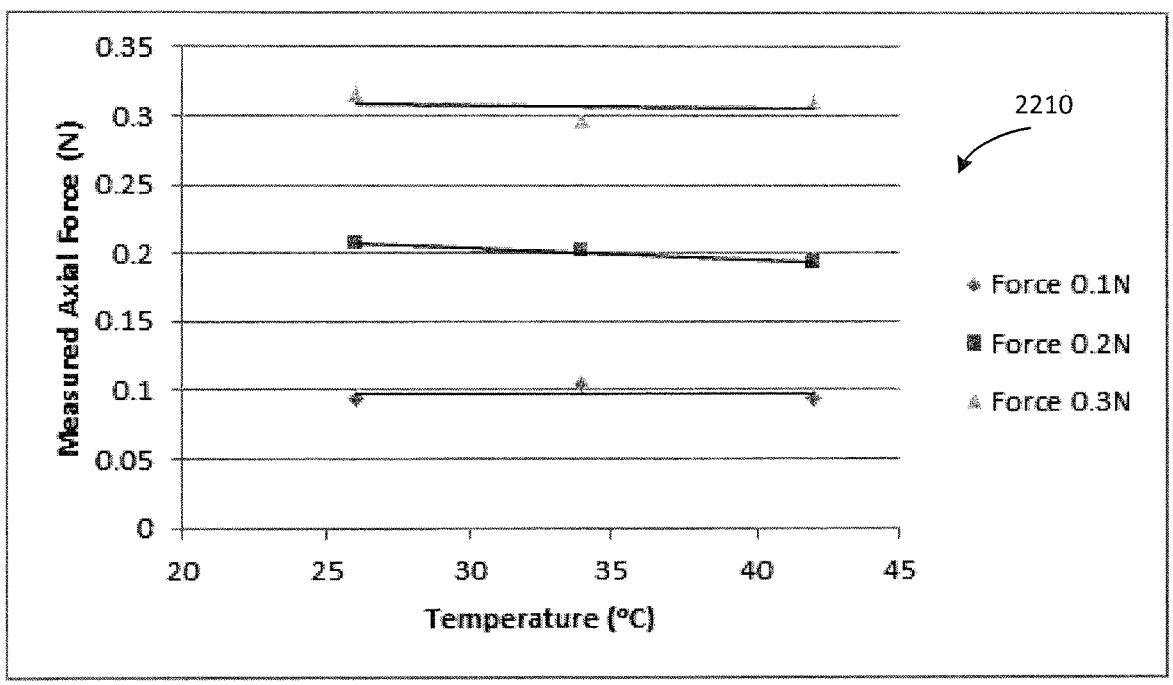
FIG. 34 is a plot showing experimental results of measured axial forces at different temperatures for the force/torque sensor of FIG. 21.
Figure 35:
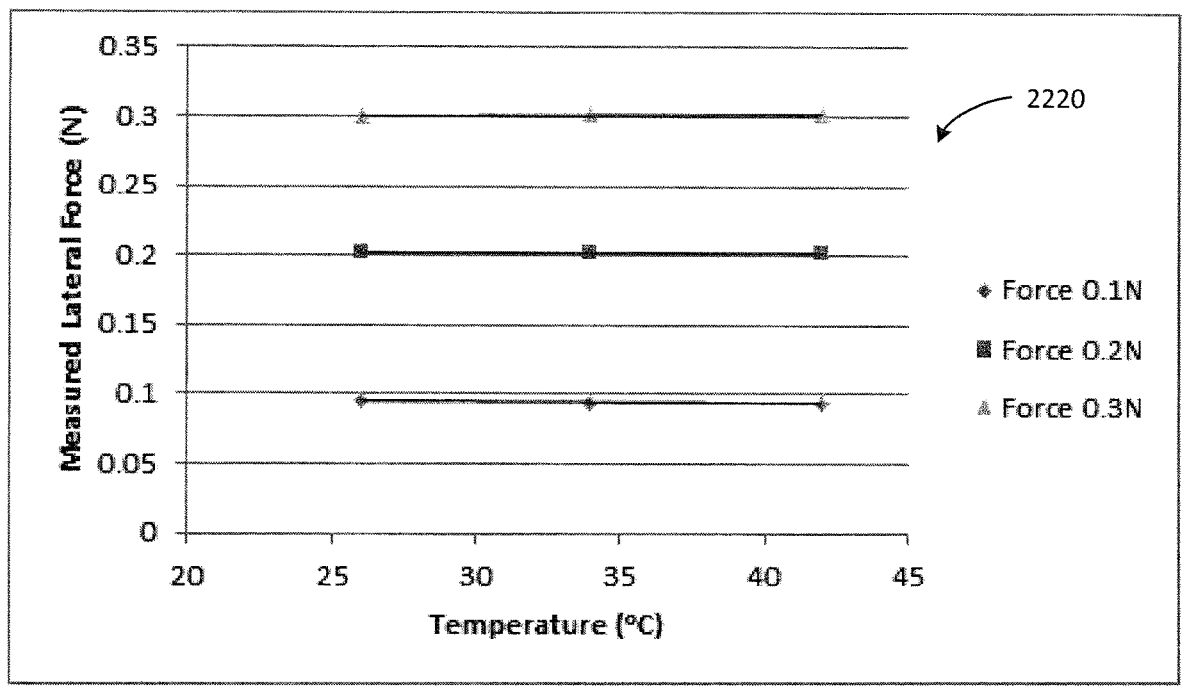
FIG. 35 is a plot showing experimental results of measured lateral forces at different temperatures for the force/torque sensor of FIG. 21.
Figure 36:
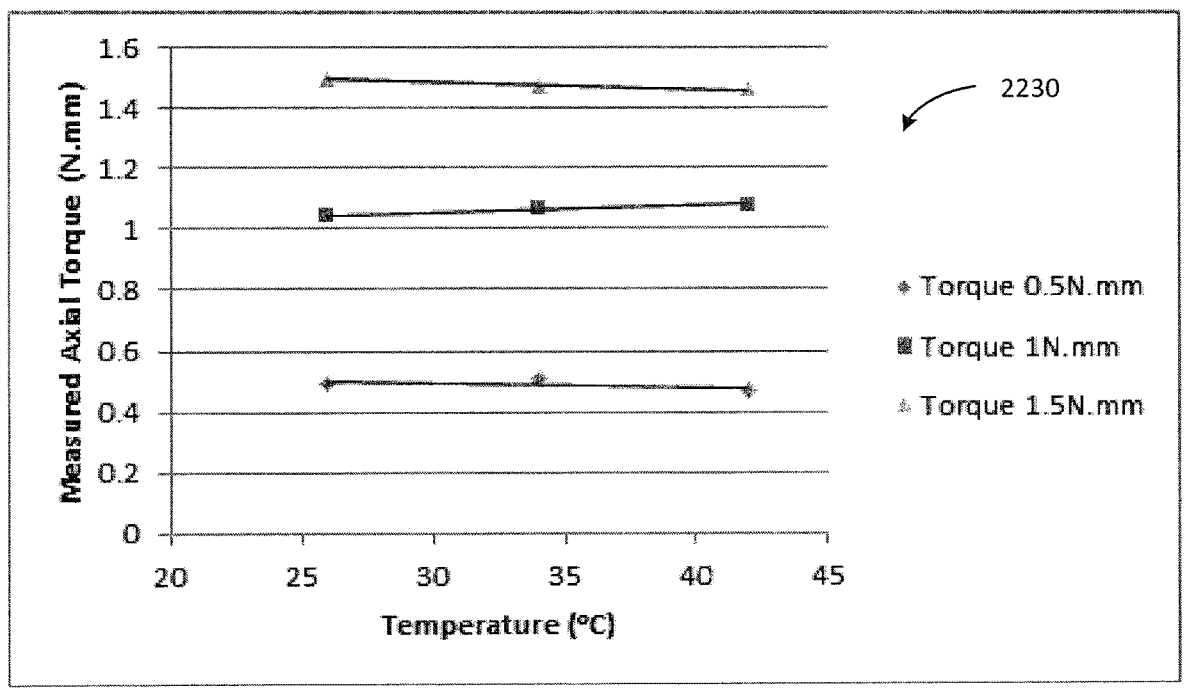
FIG. 36 is a plot showing experimental results of measured axial torques at different temperatures for the force/torque sensor of FIG. 21.

The obtained experimental results (FIGS. 23-26, 28-29 and 31-32) show that the axial and lateral forces as well as the torques applied to the fabricated sensor 2005 can be determined using differential measurements in order to cancel out the temperature effects. For verifying this characteristic of the fabricated sensor 2005, the temperature around the sensing structure 2000 was increased with a heating surface which was located close to the tip of the fabricated sensor 2005. The temperature around the tip of the sensing structure 2000 was measured with a thermometer. FIG. 33 shows a top view of the experimental setup 2200. The results 2210, 2220 and 2230, which are presented in FIGS. 34-36, show that the differential measurements of applied axial force, applied lateral force and applied axial torque made with the fabricated force/torque sensor 2005 based on shifts of the various FBGs are temperature insensitive. Since the lateral torques are mainly generated due to lateral forces applied to the tip of the sensor, the lateral torques (Tx and Ty) can be extracted using measured lateral forces (Fx and Fy).

It should be noted that a reasonable amount of errors were encountered in the experimental results presented in this section and these errors were mainly due to observational errors.

It will be appreciated that at least a portion of the various example embodiments described herein may be implemented in hardware, software, or a combination of both hardware and software. The software generally comprises one or more computer programs that are executed on programmable computers each comprising at least one processor (e.g., a microprocessor), a data storage system (including volatile and non-volatile memory or storage elements), at least one input device, and at least one output device. For any software components, program code is applied to input data to perform the functions described herein and generate output information. The output information is applied to one or more output devices, in known fashion.

Each software component or program may be implemented in a high level procedural or object oriented programming or scripting language to communicate with a computer system. However, the programs can be implemented in assembly or machine language, if desired. In any case, the language may be a compiled or interpreted language. Each such computer program is preferably stored on a storage media or a device (e.g., read-only memory) readable by a general or special purpose programmable computer, for configuring and operating the computer when the storage media or device is read by the computer to perform the one or more of the processes described herein. Accordingly, the subject system may also incorporate a computer-readable storage medium, configured with a computer program, where the storage medium so configured causes a computer to operate in a specific and predefined manner to perform the functions described herein.

Furthermore, the programs are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, or magnetic and electronic storage media, for example, or in transitory forms such as, but not limited to, wireline transmissions, satellite transmissions, internet transmission or downloading, or digital and analog signals, for example. The computer useable instructions may also be in various forms, including compiled and non-compiled code.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments described herein, the general scope of which is defined in the appended claims.

The invention claimed is:

1. A sensor assembly for an instrument having a shaft and a tip, the sensor assembly comprising:
 a sensor body for coupling to the instrument such that the shaft and the tip of the instrument extend from respective opposing ends of the sensor body, the sensor body having:
  a central longitudinal axis extending between the opposing ends;
  first and second regions extending about the central longitudinal axis; and
  first and second axially overlapping tubular members being affixed to one another at respective distal ends and being free to deform relative to one another along the central longitudinal axis, the first and second tubular members having proximal ends for coupling the sensor body to a respective one of the tip and the shaft of the instrument, and the first tubular member comprising the first region of the sensor body and the second tubular member comprising the second region of the sensor body,
 a first strain sensor coupled to the first region and configured to measure axial strain of the first region; and
 a second strain sensor coupled to the second region and configured to measure axial strain of the second region,
 wherein, when the sensor body is coupled to the shaft and the tip and is in use, each of the first and second regions of the sensor body experiences an opposite one of a tensile axial strain and a compressive axial strain in response to an axial force acting on the tip of the instrument along the central longitudinal axis.

2. The sensor assembly of claim 1, wherein the second tubular member axially overlaps the first tubular member, and the sensor body further comprises a third tubular member for coupling the proximal end of the second tubular member to the respective opposite one of the tip and the shaft of the instrument, wherein the third tubular member has a proximal end affixed to the proximal end of the second tubular member, axially overlaps the second tubular member, and is free to deform relative to the second tubular member along the central longitudinal axis of the sensor body.

3. The sensor assembly of claim 1, wherein the first tubular member comprises a proximal section and a distal section disposed between proximal and distal ends of the first tubular member, the proximal section of the first tubular member comprises the first region and the second tubular member axially overlaps the distal section of the first tubular member.

4. The sensor assembly of claim 1, wherein the first tubular member has a first cross sectional area in the first region and the second tubular member has a second cross sectional area in the second region, wherein the first cross sectional area is substantially equal to the second cross sectional area.

5. The sensor assembly of claim 4, wherein the first cross sectional area is defined by a first inner radius and a first outer radius, and the second cross sectional area is defined by a second inner radius substantially equal to the first inner radius and a second outer radius substantially equal to the first outer radius.

6. The sensor assembly of claim 1, wherein the first strain sensor comprises a first fiber Bragg grating on a first section of an optical fiber and the second strain sensor comprises a second fiber Bragg grating on a second section of the optical fiber.

7. The sensor assembly of claim 1 further comprising:
a first plurality of strain sensors including the first strain sensor, the first plurality of strain sensors coupled to the first region and spaced equidistantly about the central longitudinal axis of the sensor body, the first plurality of strain sensors being configured to measure axial strain of the first region; and
a second plurality of strain sensors including the second strain sensor, the second plurality of strain sensors coupled to the second region and spaced equidistantly about the central longitudinal axis of the sensor body, the second plurality of strain sensors being configured to measure axial strain of the second region.

8. The sensor assembly of claim 7, wherein each of the first and second plurality of strain sensors includes an equal number of strain sensors.

9. The sensor assembly of claim 8, wherein each of the first and second plurality of strain sensors includes 4 strain sensors.

10. The sensor assembly of claim 1, wherein the first and second strain sensors are oriented about the central longitudinal axis at a same angle.

11. The sensor assembly of claim 1, wherein the first and second strain sensors are configured to:
generate first and second strain signals, respectively, the first and second strain signals corresponding to the axial strain of the first region and the axial strain of the second region, respectively, and
provide the first and second strain signals to a processing unit for determining the axial force based on a combination of the first and second strain signals, the axial force being invariant to steady state temperature variations.

12. The sensor assembly of claim 1, wherein the instrument is a minimally invasive surgical instrument.

13. The sensor assembly of claim 1, wherein the sensor assembly further comprises an additional portion including:
a second sensor body having a proximal end and a distal end for coupling to the shaft and the tip of the instrument, respectively, the second sensor body defining a central longitudinal axis extending therethrough between the proximal and distal ends and having a third region and a fourth region,
a third strain sensor coupled to the third region and configured to measure axial strain of the third region; and
a fourth strain sensor coupled to the fourth region and configured to measure axial strain of the fourth region,
wherein, when the sensor body is coupled to the shaft and the tip and is in use, each of the third and fourth regions of the sensor body experiences an opposite one of a tensile axial strain and a compressive axial strain in response to an axial torque acting on the tip of the instrument about the axis, and
wherein the sensor assembly is configured to measure signals indicative of at least one of an axial force and an axial torque acting on the tip of the instrument during use.

14. A sensor assembly for an instrument having a shaft and a tip, the sensor assembly comprising:
a sensor body that is tubular having a proximal end and a distal end for coupling to the shaft and the tip of the instrument, respectively, the sensor body defining a central longitudinal axis extending therethrough between the proximal and distal ends and having a first region and a second region, the sensor body comprising:
a proximal portion extending inwardly from the proximal end of the sensor body a distal portion extending inwardly from the distal end of the sensor body;
a central side wall extending about the central longitudinal axis between the proximal portion and the distal portion, the central side wall comprising the first and second regions; and
a first slit extending through the central side wall and between the proximal portion and the distal portion;
a first strain sensor coupled to the first region and configured to measure axial strain of the first region;
a second strain sensor coupled to the second region and configured to measure axial strain of the second region,
wherein, when the sensor body is coupled to the shaft and the tip and is in use, each of the first and second regions of the sensor body experiences an opposite one of a tensile axial strain and a compressive axial strain in response to an axial torque acting on the tip of the instrument about the axis.

15. The sensor assembly of claim 14, wherein the first slit is defined by first and second opposing longitudinal side faces extending between the proximal portion and the distal portion of the sensor body, and the first region and the second region are located near the first longitudinal side face of the slit.

16. The sensor assembly of claim 14, wherein the first region is located near the proximal portion of the sensor body and the second region is located near the distal portion of the sensor body.

17. The sensor assembly of claim 14, wherein the first slit is defined by first and second opposing longitudinal side faces extending between the proximal portion and the distal portion of the sensor body, and the first region is located near the first longitudinal side face of the slit and the second region is located near the second longitudinal side face of the slit.

18. The sensor assembly of claim 14, wherein the first region and the second region are located near the distal portion of the sensor body.

19. The sensor assembly of claim 14, wherein the first region and the second region are located near the proximal portion of the sensor body.

20. The sensor assembly of claim 14, wherein the sensor body further comprises a second slit extending through the central side wall and between the proximal portion and the distal portion of the sensor body.

21. The sensor assembly of claim 20, wherein the first and second slits are spaced equidistantly about the central longitudinal axis of the sensor body.

22. The sensor assembly of claim 14, further comprising:
a plurality of slits including the first slit, each of the slits being spaced equidistantly about the central longitudinal axis of the sensor body, and extending through the central side wall and between the proximal portion and the distal portion of the sensor body;
a first plurality of strain sensors including the first strain sensor, each strain sensor of the first plurality of strain sensors being coupled to and configured to measure axial strain of a respective first region of the sensor body; and
a second plurality of strain sensors including the second strain sensor, each strain sensor of the second plurality of strain sensors being coupled to and configured to measure axial strain of a respective second region of the sensor body,
wherein, when the sensor body is coupled to the shaft and the tip and is in use, each of the respective first regions experiences one of a compressive axial strain and a tensile axial strain while each of the respective second regions experiences the other one of a compressive axial strain and a tensile axial strain in response to the torque acting on the tip of the instrument about the central longitudinal axis.

23. The sensor assembly of claim 22, wherein each slit is defined by first and second opposing longitudinal side faces extending between the proximal portion and the distal portion of the sensor body, and each first region and each second region is located near a respective first longitudinal side face of a respective slit.

24. The sensor assembly of claim 22, wherein each first region is located near the proximal portion of the sensor body and each second region is located near the distal portion of the sensor body.

25. The sensor assembly of claim 22, wherein each slit is defined by first and second opposing longitudinal side faces extending between the proximal portion and the distal portion of the sensor body, and each first region is located near a respective first longitudinal side face of a respective slit and each second region is located near a respective second longitudinal side face of a respective slit.

26. The sensor assembly of claim 22, wherein each first region and each second region is located near the distal portion of the sensor body.

27. The sensor assembly of claim 22, wherein each first region and each second region is located near the proximal portion of the sensor body.

28. The sensor assembly of claim 22, wherein each of the first plurality of strain sensors and the second plurality of strain sensors includes an equal number of strain sensors.

29. The sensor assembly of claim 28, wherein the number of strain sensors in each of the first and second plurality of strain sensors is equal to a number of slits in the plurality of slits.

30. The sensor assembly of claim 29, wherein the number of slits in the plurality of slits and the number of strain sensors in each of the first and second plurality of strain sensors is 4.

31. The sensor assembly of claim 22, wherein the strain sensors in each of the first and second plurality of strain sensors are spaced equidistantly about the central longitudinal axis.

32. The sensor assembly of claim 22, wherein each slit extends substantially parallel to the central longitudinal axis of the sensor body.

33. The sensor assembly of claim 14, wherein the first strain sensor and the second strain sensor are oriented about the central longitudinal axis at a same angle.

34. The sensor assembly of claim 14, wherein the first and second strain sensors are configured to:
generate first and second strain signals, respectively, the first and second strain signals corresponding to the axial strain of the first region and the axial strain of the second region, respectively, and
provide the first and second strain signals to a processing unit for determining the axial torque based on a combination of the first and second strain signals, the axial torque being invariant to steady state temperature variations.

35. The sensor assembly of claim 14, wherein the first strain sensor comprises a first fiber Bragg grating on a first section of an optical fiber and the second strain sensor comprises a second fiber Bragg grating on a second section of the optical fiber.

36. The sensor assembly of claim 14, wherein the instrument is a minimally invasive surgical instrument.

37. A method of sensing an axial force acting on a tip of an instrument having a sensor body of a sensor assembly coupled to a shaft and the tip of the instrument, the method comprising:
receiving at a processing unit a first set of strain signals corresponding to axial strain of a first region of the sensor body resulting from the axial force, the axial strain of the first region corresponding to one of (1) tensile axial strain and (2) compressive axial strain;
receiving at the processing unit a second set of strain signals corresponding to axial strain of a second region of the sensor body resulting from the axial force, the axial strain of the second region corresponding to the other one of (1) tensile axial strain and (2) compressive axial strain;
determining the axial force based on a combination of the first set of strain signals and the second set of strain signals using the processing unit, the axial force being invariant to steady state temperature variations, wherein the axial force is calculated by $F_z = \alpha(\epsilon_B - \epsilon_A)$, where $\alpha$ is a function of a geometry and material characteristics of the sensor body at the first and second regions and a number of respective strain signals in the first and second set of strain signals, $\epsilon_A$ is one of more strain signals from the first set of strain signals, and $\epsilon_B$ is one or more strain signals from the second set of strain signals; and
transmitting a signal corresponding to the determined axial force to a user.

38. The method of claim 37, wherein $\epsilon_A$ and $\epsilon_B$ include an equal number of strain signals.

39. The method of claim 38, wherein:
there are 4 strain sensors at the first region and 4 strain sensors at the second region;
the first region is defined by a first cross sectional area of the body and the second region is defined by a second cross sectional area of the body substantially equal to the first cross sectional area;
α is equal to $$\frac{EA}{8},$$

wherein E is a modulus of elasticity in an axial direction of a material of the first and second regions and A is one of the first cross sectional area and the second cross sectional area;
$\epsilon_A$ is equal to $\epsilon_5+\epsilon_6+\epsilon_7+\epsilon_8$, wherein $\epsilon_5$, $\epsilon_6$, $\epsilon_7$, $\epsilon_8$ are respective strain signals of the first set of strain signals; and
$\epsilon_B$ is equal to $\epsilon_1+\epsilon_2+\epsilon_3+\epsilon_4$, wherein $\epsilon_1$, $\epsilon_2$, $\epsilon_3$, $\epsilon_4$ are respective strain signals of the second set of strain signals.

40. The method of claim 37, further comprising providing a graphical display of the determined axial force to the user.

41. The method of claim 37, further comprising providing haptic feedback corresponding to the determined axial force to the user.

42. The method of claim 37, wherein the sensor assembly comprises:
the sensor body for coupling to the instrument such that the shaft and the tip of the instrument extend from respective opposing ends of the sensor body, the sensor body having:
a central longitudinal axis extending between the opposing ends; and
first and second regions extending about the central longitudinal axis;
a first strain sensor coupled to the first region and configured to measure axial strain of the first region; and
a second strain sensor coupled to the second region and configured to measure axial strain of the second region,
wherein, when the sensor body is coupled to the shaft and the tip and is in use, each of the first and second regions of the sensor body experiences an opposite one of a tensile axial strain and a compressive axial strain in response to an axial force acting on the tip of the instrument along the central longitudinal axis.

43. A method of sensing an axial torque acting on a tip of an instrument having a sensor body of a sensor assembly coupled to a shaft and the tip of the instrument, the method comprising:
receiving at a processing unit a first set of strain signals corresponding to axial strain of one or more first regions of the body resulting from the axial torque, the axial strain of the one or more first regions corresponding to one of (1) tensile axial strain and (2) compressive axial strain;
receiving at the processing unit a second set of strain signals corresponding to axial strain of a corresponding number of second regions of the body resulting from the axial torque, the axial strain of the corresponding number of second regions corresponding to the other one of (1) tensile axial strain and (2) compressive axial strain;
determining the axial torque based on a combination of the first set of strain signals and the second set of strain signals using the processing unit, wherein the determined axial torque is invariant to steady state temperature variations, and wherein the axial torque is calculated by $T_z=\tau(\epsilon_D-\epsilon_C)$, where $\tau$ is a function of a geometry and material characteristics of the body at the one or more first and second regions and a number of strain signals in the first and second set of strain signals, $\epsilon_C$ is one or more strain signals from the first set of strain signals, and $\epsilon_D$ is one or more strain signals from the second set of strain signals; and
transmitting a signal corresponding to the determined axial torque to a user.

44. The method of claim 43, wherein $\epsilon_C$ and $\epsilon_D$ include an equal number of strain signals.

45. The method of claim 44, wherein there are 4 strain sensors at the one or more first regions and 4 strain sensors at the one or more second regions and:
$\epsilon_C$ is equal to $\epsilon_9+\epsilon_{10}+\epsilon_{11}+\epsilon_{12}$, wherein $\epsilon_9$, $\epsilon_{10}$, $\epsilon_{11}$, $\epsilon_{12}$ are respective strain signals of the first set of strain signals; and
$\epsilon_D$ is equal to $\epsilon_{13}+\epsilon_{14}+\epsilon_{15}+\epsilon_{16}$, wherein $\epsilon_{13}$, $\epsilon_{14}$, $\epsilon_{15}$, $\epsilon_{16}$ are respective strain signals of the second set of strain signals.

46. The method of claim 42, further comprising providing a graphical display of the determined axial torque to the user.

47. The method of claim 42, further comprising providing haptic feedback corresponding to the determined axial torque to the user.

* * * * *

UNITED STATES PATENT AND TRADEMARK OFFICE
CERTIFICATE OF CORRECTION

PATENT NO. : 10,564,057 B2
APPLICATION NO. : 15/560804
DATED : February 18, 2020
INVENTOR(S) : Janabi-Sharifi et al.

It is certified that error appears in the above-identified patent and that said Letters Patent is hereby corrected as shown below:

In the Claims

Claim 37, Column 34, Line 60, "...one of more..." should read -- one or more --.

Claim 45, Column 36, Line 37, "...+$\xi_{12}$ ..." should read -- +$\epsilon_{12}$ --.

Signed and Sealed this
First Day of September, 2020

Andrei Iancu
*Director of the United States Patent and Trademark Office*